United States Patent
Missling et al.

(10) Patent No.: US 11,498,908 B2
(45) Date of Patent: Nov. 15, 2022

(54) A2-73 CRYSTALLINE POLYMORPH COMPOSITIONS OF MATTER AND METHODS OF USE THEREOF

(71) Applicant: ANAVEX LIFE SCIENCES CORP., New York, NY (US)

(72) Inventors: Christopher U. Missling, New York, NY (US); Alani Selvey, New York, NY (US)

(73) Assignee: ANAVEX LIFE SCIENCES CORP., New York, NY (US)

(*) Notice: Subject to any disclaimer, the term of this patent is extended or adjusted under 35 U.S.C. 154(b) by 106 days.

(21) Appl. No.: 17/046,929

(22) PCT Filed: Apr. 12, 2019

(86) PCT No.: PCT/US2019/027369
§ 371 (c)(1),
(2) Date: Oct. 12, 2020

(87) PCT Pub. No.: WO2019/200345
PCT Pub. Date: Oct. 17, 2019

(65) Prior Publication Data
US 2021/0115004 A1    Apr. 22, 2021

Related U.S. Application Data

(60) Provisional application No. 62/656,435, filed on Apr. 12, 2018.

(51) Int. Cl.
| | | |
|---|---|---|
| *C07D 307/14* | (2006.01) | |
| *A61P 25/28* | (2006.01) | |
| *A61K 9/28* | (2006.01) | |
| *A61K 9/70* | (2006.01) | |

(52) U.S. Cl.
CPC .............. *C07D 307/14* (2013.01); *A61K 9/28* (2013.01); *A61K 9/7023* (2013.01); *A61P 25/28* (2018.01); *C07B 2200/13* (2013.01)

(58) Field of Classification Search
None
See application file for complete search history.

(56) References Cited

U.S. PATENT DOCUMENTS

2017/0360798 A1    12/2017    Vamvakides et al.

FOREIGN PATENT DOCUMENTS

| WO | 20140159814 A1 | 10/2014 | | |
|---|---|---|---|---|
| WO | 20170013498 A1 | 1/2017 | | |
| WO | WO 2017/013498 | * 1/2017 | ........... | C07D 307/14 |
| WO | 20170132127 A1 | 8/2017 | | |
| WO | 20180231216 A1 | 12/2018 | | |
| WO | 2019108653 A1 | 6/2019 | | |

OTHER PUBLICATIONS

Saal C "Pharmaceutical salts: a summary on doses of salt formers from the Orange Book" Eur J Pharm Sci, Jul. 16, 2013;49(4):614-23. doi: 10.1016/j.ejps.2013.05.026. Epub Jun. 5, 2013.
Extended European Search Report dated May 21, 2021 in corresponding European Patent Application 19785595.0, 11 pages.
International Search Report and Written Opinion dated Jul. 25, 2019 in corresponding International Patent Application No. PCT/US2019/027369.

* cited by examiner

*Primary Examiner* — Craig D Ricci
(74) *Attorney, Agent, or Firm* — Tara A. Nealey; Rong Yang; Polsinelli PC

(57) ABSTRACT

The present disclosure provides crystalline forms of tetrahydro-N,N-dimethyl-2,2-diphenyl-3-furanmethanamine (A2-73), in freebase or salt forms. Also described are pharmaceutical formulations and dosage forms comprising the disclosed crystal forms, and methods of using crystalline A2-73 in dosage forms for neuroprotection including treatment of neurodegenerative and other diseases.

29 Claims, 41 Drawing Sheets

XRPD Patterns of Anavex2-73 Crystalline Forms 1 – VIII

Single-crystal Derived Form III XRPD Pattern vs. Example of Isolated Bulk Form III XRPD Pattern Single-crystal Derived Form VIII XRPD Pattern vs Example of Isolated Bulk Form VIII XRPD Pattern

FIG. 35C
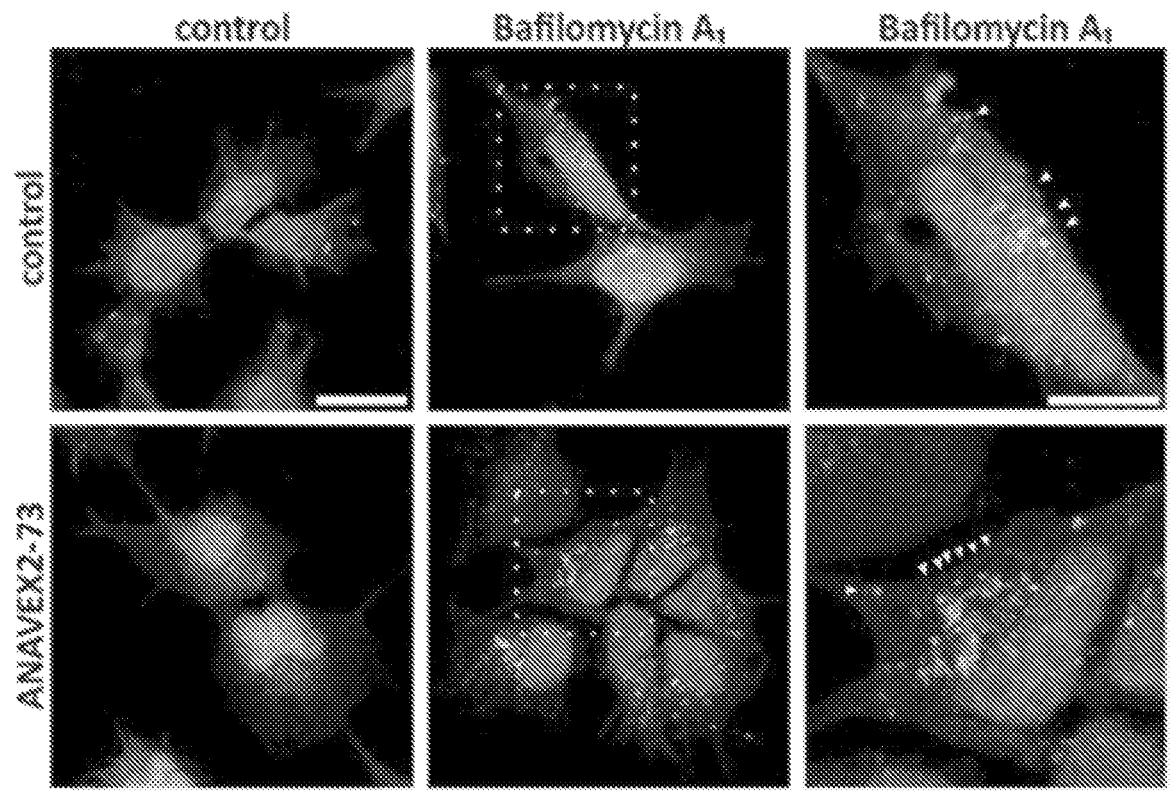
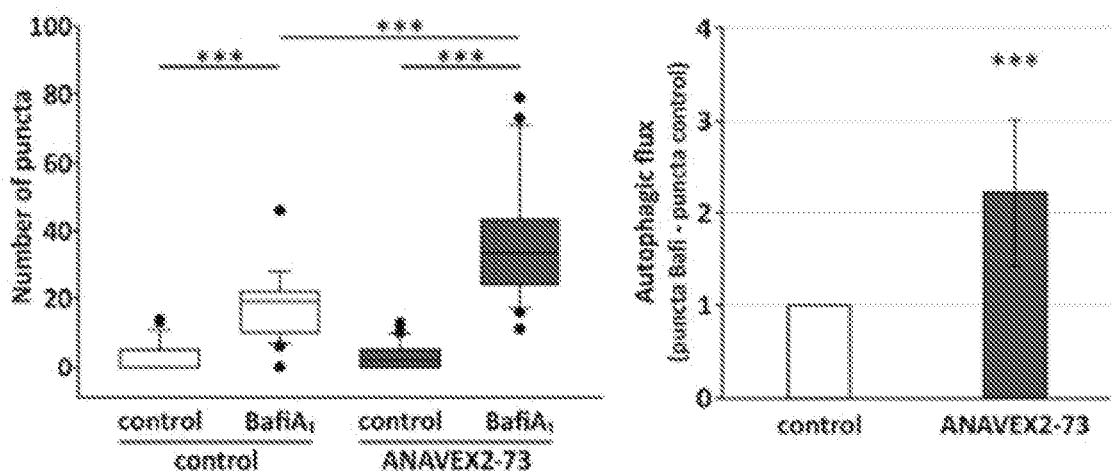

A2-73 CRYSTALLINE POLYMORPH COMPOSITIONS OF MATTER AND METHODS OF USE THEREOF

CROSS-REFERENCE TO RELATED APPLICATIONS

This application is a U.S. National Stage Application of International Application No. PCT/US2019/027369, filed Apr. 12, 2019, which claims the benefit of U.S. Provisional Patent Application No. 62/656,435 filed Apr. 12, 2018, the entire disclosure of each of which is incorporated herein by reference.

FIELD OF THE INVENTION

The present invention relates generally to crystalline forms of tetrahydro-N,N-dimethyl-2,2-diphenyl-3-furanmethanamine (A2-73), dosage forms containing them and methods of their use in treatment.

BACKGROUND OF THE INVENTION

Tetrahydro-N,N-dimethyl-2,2-diphenyl-3-furanmethanamine (ANAVEX2-73 or AV2-73) is a mixed muscarinic receptor ligand and Sig-1R agonist with affinities in the low micromolar range. A2-73 can treat neurodevelopmental disorders and neuroprotective characteristics. Improved drug formulations showing, for example, better bioavailability, better stability, or enhanced delivery of pharmaceutically active compounds are consistently sought, there is an ongoing need for more fully characterized, new, drug molecules. There is also an ongoing need for methods of treating neurodegenerative diseases.

SUMMARY OF THE INVENTION

In one aspect, the present disclosure encompasses a crystalline form of tetrahydro-N,N-dimethyl-2,2-diphenyl-3-furanmethanamine (A2-73), wherein the crystalline form is a salt or a freebase. A salt can be any pharmaceutically acceptable salt, such as a hydrochloride salt, a fumarate salt, a sulfate salt, a dihydrogen phosphate salt, a benzoate salt, a mesylate salt, an edisylate salt, and an oxalate salt. It shall be understood that in any of the pharmaceutical formulations, dosage forms and methods disclosed herein, crystalline A2-73 can be the freebase disclosed herein, or a salt as disclosed herein including any one or more of a hydrochloride salt, a fumarate salt, a sulfate salt, a dihydrogen phosphate salt, a benzoate salt, a mesylate salt, an edisylate salt, and an oxalate salt.

When the A2-73 is a hydrochloride salt, the hydrochloride salt is characterized by the XRPD pattern shown in FIG. 4, FIG. 6, FIG. 8, FIG. 9, FIG. 10, FIG. 11, FIG. 12, and FIG. 14. The hydrochloride salt characterized by the XRPD pattern shown in FIG. 4 can be further characterized by the particle shapes and sizes depicted in FIG. 2 and FIG. 3. The hydrochloride salt characterized by the XRPD pattern shown in FIG. 6 can be further characterized by the particle shapes and sizes depicted in FIG. 5. hydrochloride salt characterized by the XRPD pattern shown in FIG. 8 can be further characterized by the particle shapes and sizes depicted in FIG. 7. The hydrochloride salt characterized by the XRPD pattern shown in FIG. 14 is further characterized by the particle shapes and sizes depicted in FIG. 13.

The crystalline form of A2-73 can be a sulfate salt. The sulfate salt can be characterized by the XRPD pattern shown in FIG. 18 and FIG. 19. The sulfate salt characterized by the XRPD pattern shown in FIG. 18 can be further characterized by the particle shapes depicted in FIG. 17.

The crystalline form of A2-73 can be a mesylate salt. The mesylate salt can be characterized by the XRPD pattern shown in FIG. 20.

The crystalline form of A2-73 can be an oxalate salt. The oxalate salt can be characterized by the XRPD pattern shown in FIG. 21, FIG. 22, and FIG. and 23.

The crystalline form of A2-73 can be a dihydrogen phosphate salt. The dihydrogen phosphate salt can be characterized by the XRPD pattern shown in FIG. 25. The dihydrogen phosphate salt characterized by the XRPD pattern shown in FIG. 25 is further characterized by the particle shapes depicted in FIG. 24.

The crystalline form of A2-73 can be an edisylate salt. The edisylate salt can be characterized by the XRPD pattern shown in FIG. 26.

The crystalline form of A2-73 can be a benzoate salt. The benzoate salt can be characterized by the XRPD pattern shown in FIG. 27.

The crystalline form of A2-73 can be a fumarate salt. The fumarate salt can be characterized by the XRPD pattern shown in FIG. 29, FIG. 30, FIG. 32, FIG. 33, and FIG. 34. The fumarate salt characterized by the XRPD pattern shown in FIG. 29 can be further characterized by the particle shapes depicted in FIG. 28, and the fumarate salt characterized by the XRPD pattern shown in FIG. 32 can be further characterized by the particle shapes depicted in FIG. 31.

The crystalline form of A2-73 can be a freebase. The freebase can be characterized by the XRPD pattern shown in FIG. 16. The crystalline form characterized by the XRPD pattern shown in FIG. 16 is further characterized by the particle shapes depicted in FIG. 15.

In another aspect, the present disclosure encompasses a dosage form comprising a therapeutically effective amount of A2-73 in a crystalline form selected from the group consisting of A2-73 freebase and a A2-73 salt. The dosage form can comprise from about 1 mg to about 50 g, from about 1 mg to about 500 mg, or about 1 mg to about 100 mg of A2-73 freebase or an A2-73 salt.

A dosage form can be formulated for extended release of crystalline A2-73. In any dosage form, crystalline A2-73 can be a freebase, and the dosage form can comprise from about 1 mg to about 500 mg of A2-73 freebase. A dosage form can be a transdermal patch. A transdermal patch can contain from about 40 mg to about 60 mg, from about 80 mg to about 120 mg, or about 180 mg to about 220 mg of A2-73 freebase. The dosage form can be an enteric coated oral formulation, and the formulation can comprise from about 1 mg to about 50 mg A2-73 freebase.

In any dosage form, crystalline A2-73 can be a pharmaceutically acceptable salt. A pharmaceutically acceptable salt can be selected from the group consisting of fumarate, sulfate, mesylate, dihydrogen phosphate, edisylate, benzoate, hydrochloride, and oxalate. In some aspects, an A2-73 salt is fumarate, and the dosage form can be a transdermal patch. The transdermal patch can contain from about 1 mg to about 55 mg of A2-73 fumarate salt.

In some aspects, a dosage form can be an enteric coated oral formulation. The enteric coated oral formulation can comprise from about 10 mg to about 50 mg, from about 20 mg to about 30 mg, or from about 15 mg to about 25 mg of A2-73 fumarate salt.

In another aspect, the present disclosure encompasses a pharmaceutical formulation for delivery of A2-73. The formulation comprises a therapeutically effective amount of a crystalline form of A2-73 selected from A2-73 freebase and A2-73 salt.

A pharmaceutical formulation can further comprise one or more pharmaceutically acceptable excipients selected from chemical enhancers, humectants, pressure sensitive adhesives, antioxidants, solubilizers, thickening agents, plasticizers, adjuvants, carriers, excipients, vehicles, and any combinations thereof. The one or more excipients can be selected for preparing the formulation for oral, transdermal, parenteral, intraperitoneal, intravascular, subcutaneous, by inhalation spray, rectal, or intrapulmonary administration.

In any pharmaceutical formulation, crystalline A2-73 can be selected from freebase, and any pharmaceutically acceptable salt. In one aspect of a pharmaceutical formulation, crystalline A2-73 is a fumarate salt, or a hydrochloride salt. A pharmaceutical formulation can be for example an oral formulation comprising from about 1% to about 100% by weight crystalline A2-73.

A pharmaceutical formulation can be prepared for extended delivery of crystalline A2-73 and can comprise from about 1 mg to about 50 g of crystalline A2-73. An extended delivery formulation can for example be a subcutaneous injectable dosage formulation comprising from about 0.5 g to about 3 g of crystalline A2-73.

A pharmaceutical formulation can be a transdermal patch. The patch can comprise from about 40 mg to about 60 mg, from about 80 mg to about 120 mg, or about 180 mg to about 220 mg of A2-73 freebase. The patch can also comprise from about 1 mg to about 55 mg of A2-73 fumarate salt.

The formulation can also be an oral formulation. The oral formulation can comprise from about 1 mg to about 50 mg A2-73 freebase, from about 10 mg to about 50 mg, from about 20 mg to about 30 mg, or from about 15 mg to about 25 mg of A2-73 fumarate salt. The oral formulation can comprise comprises A2-73 hydrochloride salt.

The extended delivery formulation can be a subcutaneous dosage form comprising from about 0.1 to about 5 g of crystalline A2-73.

In yet another aspect, the present disclosure encompasses a transdermal patch for extended delivery of A2-73. The patch may comprise a therapeutically effective amount of a crystalline form of A2-73 selected from A2-73 freebase and A2-73 salt. The transdermal patch can for example be a matrix patch. The patch can further comprise one or more components selected from chemical enhancers, humectants, pressure sensitive adhesives, antioxidants, solubilizers, thickening agents, plasticizers, and any combinations thereof. The patch can be covered by a peripheral pressure sensitive adhesive that extends beyond the patch in all directions.

A transdermal patch comprising A2-73 freebase can contain from about 40 mg to about 60 mg, from about 80 mg to about 120 mg, or about 180 mg to about 220 mg of A2-73 freebase.

A transdermal patch can comprise A2-73 fumarate salt. A patch comprising A2-73 fumarate salt can contain from about 1 mg to about 55 mg of A2-73 fumarate salt.

The surface area of a transdermal patch in contact with the skin of a subject can range from about 1 $cm^2$ to about 20 $cm^2$, from about 3 $cm^2$ to about 5 $cm^2$, or from about 8 $cm^2$ to about 10 $cm^2$. The patch can for example be configured to provide for extended release of A2-73 over a period ranging from about 1 day to about 7 days. Further, the patch can have a transcutaneous maximum flux of A2-73 from the matrix ranging from about 250-350 µg/$cm^2$/h.

In other aspects, the present disclosure encompasses an oral formulation for extended delivery of A2-73. The oral formulation comprises a core comprising a therapeutically effective amount of a crystalline form of A2-73 selected from A2-73 freebase and A2-73 salt; and an enteric coating surrounding the core.

The oral formulation can comprise A2-73 freebase that can range from about 1 mg to about 50 mg A2-73 freebase. The oral formulation can also comprise A2-73 fumarate salt that can range in the core from about 10 mg to about 50 mg, from about 20 mg to about 30 mg, or from about 15 mg to about 25 mg of A2-73 fumarate salt, or about 35% to about 40% by weight A2-73 freebase or A2-73 fumarate. The oral formulation can also comprise in the core about 55% to about 70% by weight hydroxypropyl methylcellulose acetate succinate, about 0.3% to about 0.9% by weight magnesium stearate, and about 0.05% to about 0.5% by weight colloidal silicon dioxide. The hydroxypropyl methylcellulose acetate succinate can be soluble in aqueous solutions with a pH of about 5.5 and greater, a second grade of hydroxypropyl methylcellulose acetate succinate is soluble in aqueous solutions with a pH of about 6.8 and greater, and combinations thereof. The formulation can provide for extended release of A2-73 over a period ranging from about 1 day to about 3 days, and can deliver about 15 to about 30 mg/day of A2-73 to a subject.

In one aspect, the disclosure encompasses a method of administering A2-73 to a subject in need thereof. The method comprises administering the A2-73 to the subject a crystalline form of A2-73 selected from A2-73 freebase and a pharmaceutically acceptable salt of A2-73. In various aspects of the methods, crystalline A2-73 can be administered in a dosage form or pharmaceutical formulation comprising crystalline A2-73 freebase, or a pharmaceutically acceptable salt of A2-73 as disclosed herein. A dosage form can be an immediate release or an extended release dosage form as disclosed herein. In certain aspects, the salt can be a fumarate salt, or a hydrochloride salt. In other aspects, crystalline A2-73 can be administered to the subject over a period of about 30 days, about 60 days, about 120 days or about 180 days.

In one aspect, administration can comprise administering using an extended release dosage form which can be administered dermally using a transdermal patch. The transdermal patch can be for example be replaced periodically such as daily, every other day, weekly, every 10 days to two weeks, or monthly or more. In one aspect, a transdermal patch can maintain a level of A2-73 in the blood of the subject ranging from about 5 ng/ml to about 15 ng/ml, and particularly about 10 ng/ml over the period.

In another aspect, administration can comprise administering using an enteric coated oral dosage form comprising crystalline A2-73. The enteric coated oral dosage form can be administered daily, or every other day and can deliver about 15 to about 30 mg/day of A2-73. An enteric coated oral dosage form comprising crystalline A2-73 can provide administration of A2-73 over an extended period of time which can be for example from about 1 day, about 2 days (about 48 hours), 3 days (about 72 hours), about 4 days, about 5 days, about 6 days, about 7 days, or more.

In another aspect, the disclosure encompasses a method of treating Alzheimer's disease in a subject in need thereof, the method comprising administering to the subject a dosage form comprising a therapeutically effective amount of a crystalline form of A2-73 selected from A2-73 freebase and A2-73 salt.

In another aspect, the disclosure encompasses a method of treating a progressive dementia in a subject in need thereof, the method comprising administering to the subject a dosage form comprising a therapeutically effective amount of a crystalline form of A2-73 selected from A2-73 freebase and A2-73 salt.

In any of the methods, the dosage form being administered can be an extended dosage form as described herein.

In another aspect, the disclosure encompasses a pharmaceutical composition for the treatment of a neurodegenerative disease comprising an anti-neurodegenerative effective amount of A2-73. The therapeutically effective amount can range from about 0.5 mg to about 20 mg, from about 1 mg to about 60 mg, from about 30 mg to about 50 mg, or from about 3 mg to about 5 mg.

In another aspect, the disclosure encompasses a dosage form comprising an anti-neurodegenerative effective amount of A2-73 effective for the treatment of a neurodegenerative disease. The amount of anti-neurodegenerative effective amount of A2-73 can be from about 0.01 to about 10 mg/kg or from about 0.01 to about 10 mg/kg.

In one aspect, the disclosure encompasses a method of treating a neurodegenerative disease in a subject in need thereof. The method comprises administering to the subject an anti-neurodegenerative effective amount of A2-73. The degenerative disease can be Alzheimer's disease, Parkinson's disease, prion diseases, Huntington's disease, motor neuron diseases (MND) such as amyotrophic lateral sclerosis, spinocerebellar ataxia (SCA), or spinal muscular atrophy (SMA).

The anti-neurodegenerative effective amount of A2-73 may be about 0.5 mg/day to about 100 mg/day, about 1 to about 60 mg/day, about 20 to about 50 mg/day, about 20 to about 30 mg/day, or about 15 to about 25 mg/day. Further, administering to the subject an anti-neurodegenerative effective amount of A2-73 can provide blood levels of A2-73 of about 10 ng/ml, or about 12 ng/ml.

BRIEF DESCRIPTION OF THE FIGURES

FIG. 35 Sig-1R activation enhances autophagic activity. FIG. 35C depicts representative confocal fluorescence microscopic images and plots quantifying the puncta in HEK293 cells stably transfected with a GFP-LC3B reporter construct (Scale bar=20 μm or 10 μm, respectively. Thirty cells per treatment in three independent experiments. *** $p<0.001$, t-test.

FIG. 36. Sig-1R activation stimulates ULK1 activation and affects expression levels of distinct autophagy network factors.

FIG. 37. Sig-1R activation by ANAVEX2-73 enhances autophagy in *C. elegans*.

FIG. 38. Sig-1R activation by ANAVEX2-73 increases proteostasis capacity in *C. elegans* and ameliorates Aβ42-caused paralysis.

DETAILED DESCRIPTION

The present disclosure is based in part on the surprising discovery that crystalline polymorphs of tetrahydro-N,N-dimethyl-2,2-diphenyl-3-furanmethanamine ("A2-73" or "Anavex2-73") in freebase or pharmaceutically acceptable salt forms are suitable for oral, transdermal, subcutaneous, or other forms of administration, and can be formulated to provide immediate or extended release of A2-74 upon administration. Crystalline polymorphs of A2-73, dosage forms, and formulations comprising crystalline polymorphs of A2-73 are described below. Methods of using the crystalline polymorphs of A2-73 for treatment are also disclosed, encompassing use of A2-73 for neuroprotection, wherein neuroprotection includes treatment for neurodegenerative diseases.

I. Crystalline Polymorphs

In one aspect the present disclosure presents a crystalline polymorphs of A2-73. Each crystalline polymorph can be in the form of a freebase or can be in the form of a salt. The crystalline polymorphs are characterized by XRPD and other data provided herein. Properties of each crystalline polymorph are described below.

a. Form I, Hydrochloride Salt

Figure 1:
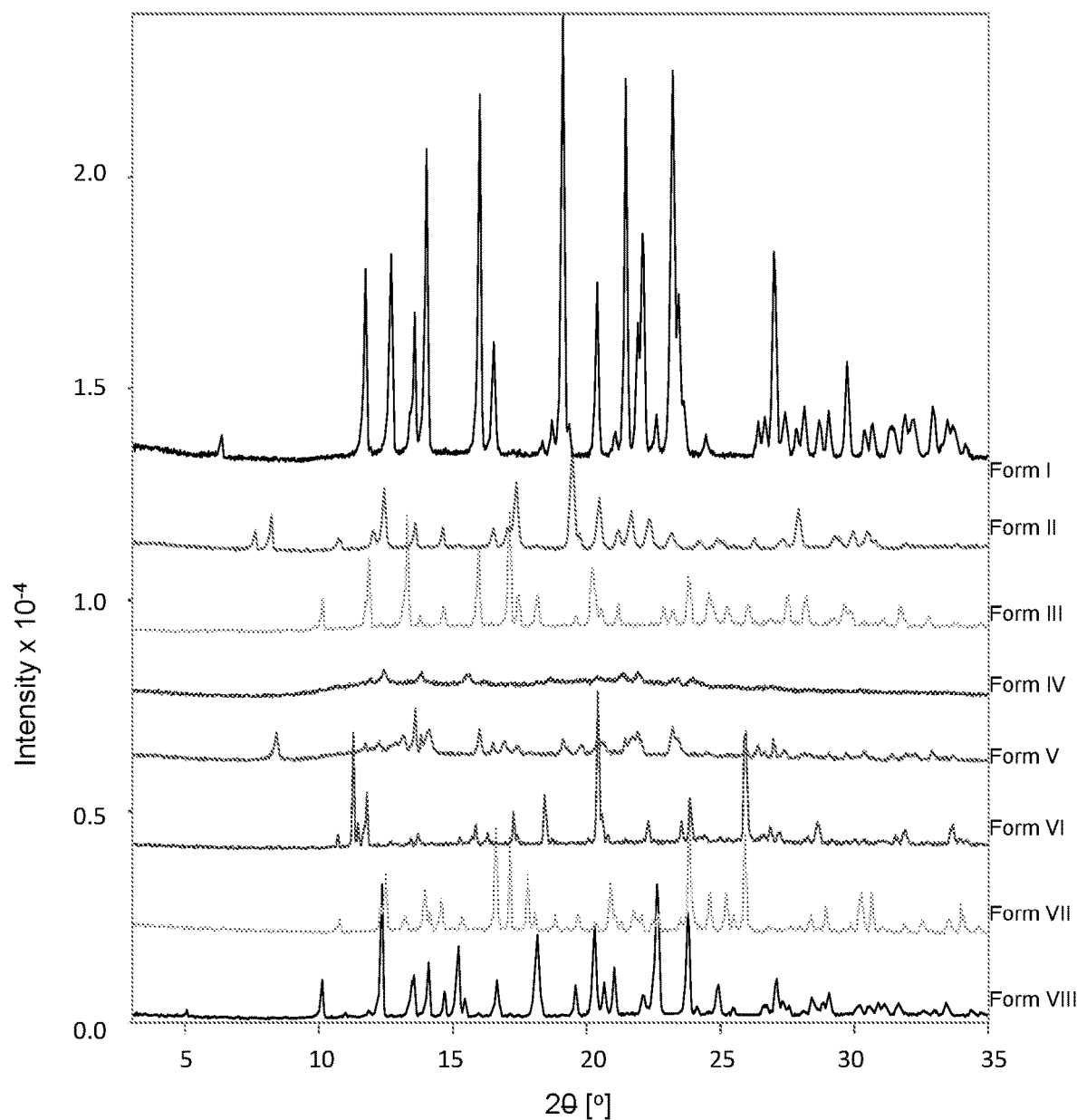
FIG. 1 is an overlay of XRPD patterns for Anavex2-73 (hydrochloride salt) solid-state forms.
Figure 2:
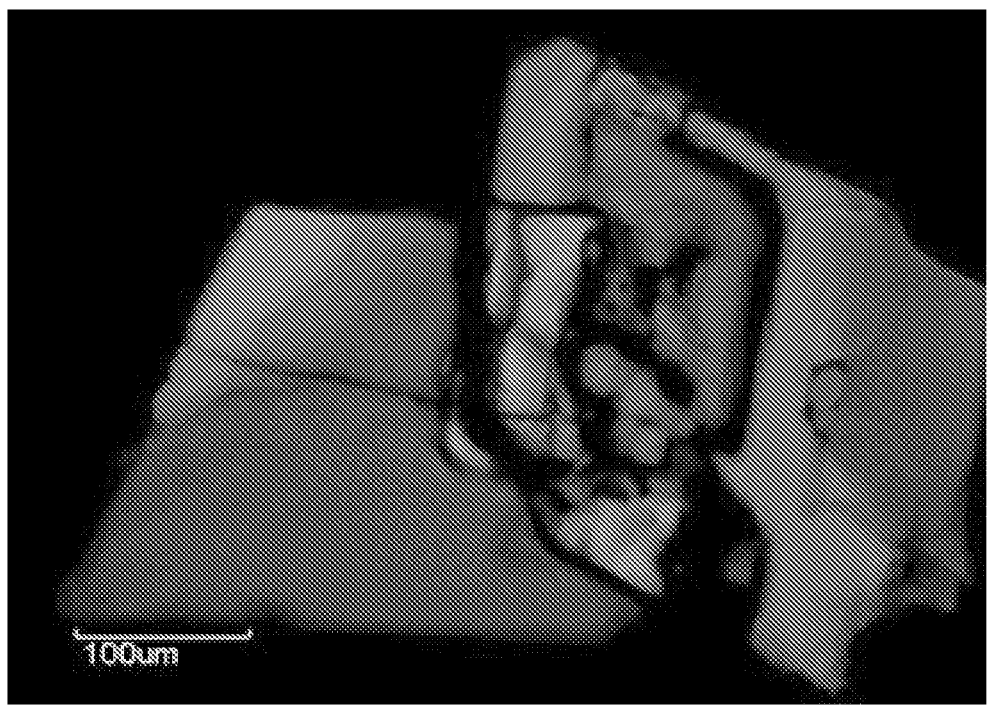
FIG. 2 shows a micrograph of Form I crystals in polarized-light.
Figure 3:
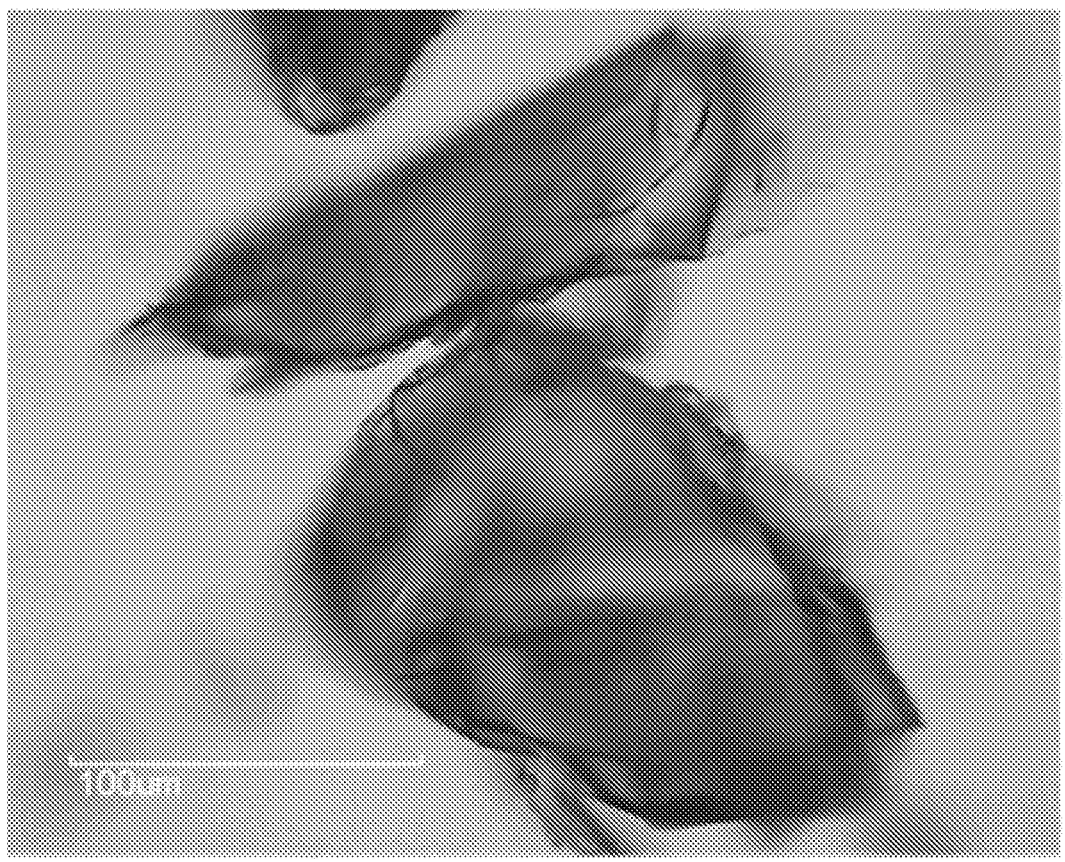
FIG. 3 is a micrograph of crystals of Form I Obtained by Sublimation.

Form I is anhydrous, crystalline (birefringent plates and plate fragments) and shown via single-crystal x-ray analysis to form racemic crystals, meaning each individual crystal contains both enantiomers. Form I is the thermodynamically-preferred racemic crystal form of the hydrochloride salt and is the current Anavex2-73 active pharmaceutical ingredient (API). FIG. 2 shows a polarized-light microscopy (PLM) of Form I. FIG. 3 shows crystals of Form I obtained by sublimation.

Single-Crystal X-Ray Analysis Summary:

Crystal Type: Racemic

Space Group: Monoclinic P21/c

Unit Cell Parameters:

a=14.1623(4) Å α=90.00°
b=9.0974(3) Å β=102.103(3)°
c=13.4052(4) Å γ=90.00°
Volume=1688.73(9) Å$^3$
Z=4, Z'=1
Density (ρcalc)=1.250 g/cm3

Figure 4:
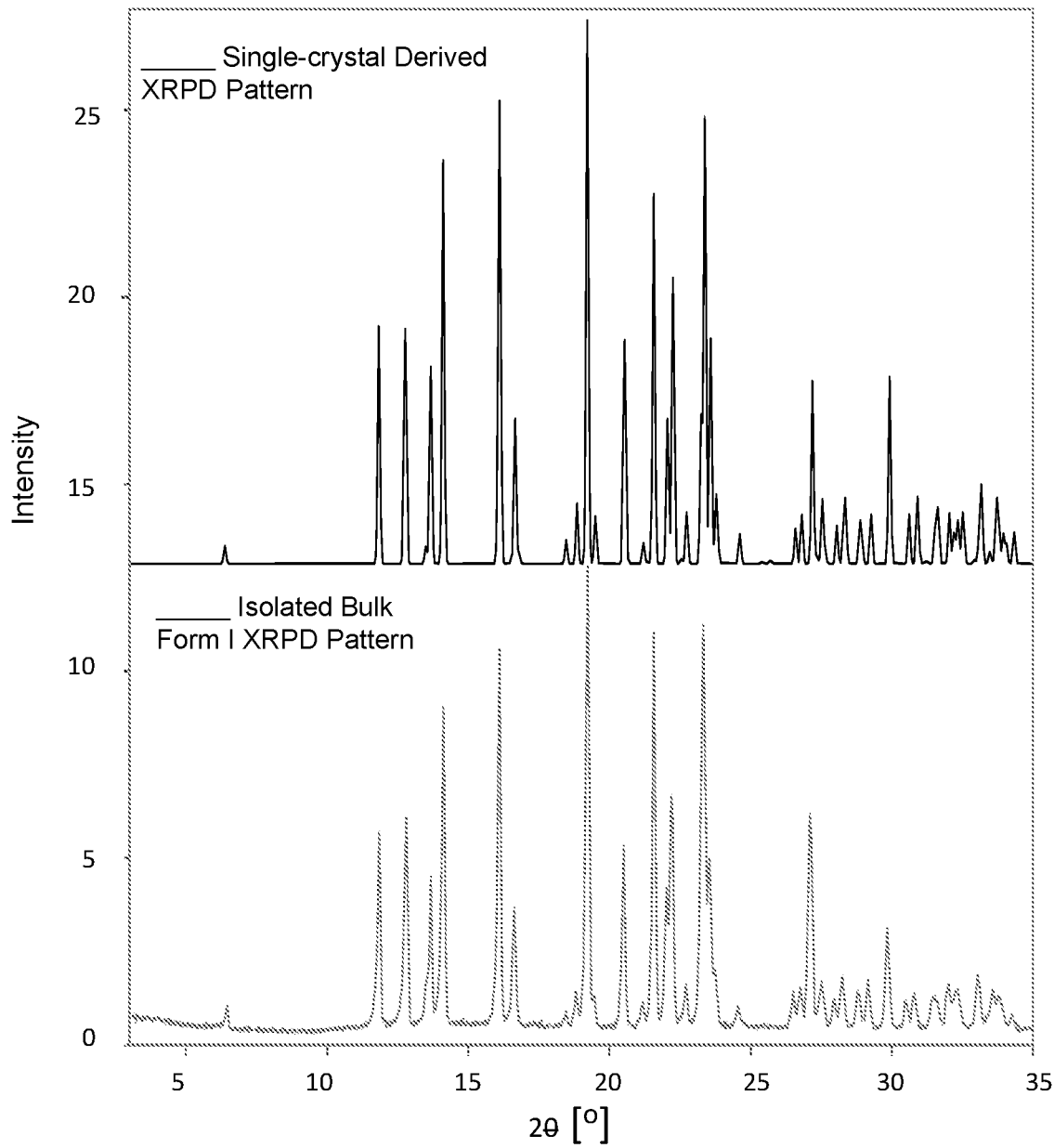
FIG. 4 shows XRPD pattern of Anavex2-73 Form I derived from single-crystal results for copper Kα radiation vs. experimentally measured XRPD pattern obtained for an isolated bulk sample of Form I.

XRPD pattern of Anavex2-73 Form I derived from single-crystal results for copper Kα radiation vs. experimentally measured XRPD pattern obtained for an isolated bulk sample of Form I is shown in FIG. 4.

The twenty most intense XRPD peaks for Anavex2-73 Form I, measured using copper Kα radiation are shown in Table 1.

TABLE 1

XRPD peaks for Anavex2-73 Form I

| Pos. [°2θ] | d-spacing [Å] | Rel. Int. [%] |
|---|---|---|
| 11.74 | 7.537 | 43 |
| 12.71 | 6.964 | 46 |
| 13.58 | 6.523 | 33 |
| 14.02 | 6.315 | 70 |
| 16.00 | 5.538 | 83 |
| 16.54 | 5.361 | 26 |
| 19.13 | 4.640 | 100 |
| 20.40 | 4.354 | 39 |
| 21.47 | 4.139 | 86 |
| 21.92 | 4.055 | 30 |
| 22.10 | 4.022 | 50 |
| 23.23 | 3.829 | 87 |
| 23.43 | 3.796 | 37 |
| 23.66 | 3.761 | 11 |
| 27.00 | 3.302 | 46 |
| 28.14 | 3.171 | 11 |
| 29.07 | 3.072 | 10 |
| 29.73 | 3.003 | 21 |
| 29.79 | 3.004 | 17 |
| 32.95 | 2.716 | 11 | b. Form II, Hydrochloride Salt

Figure 5:
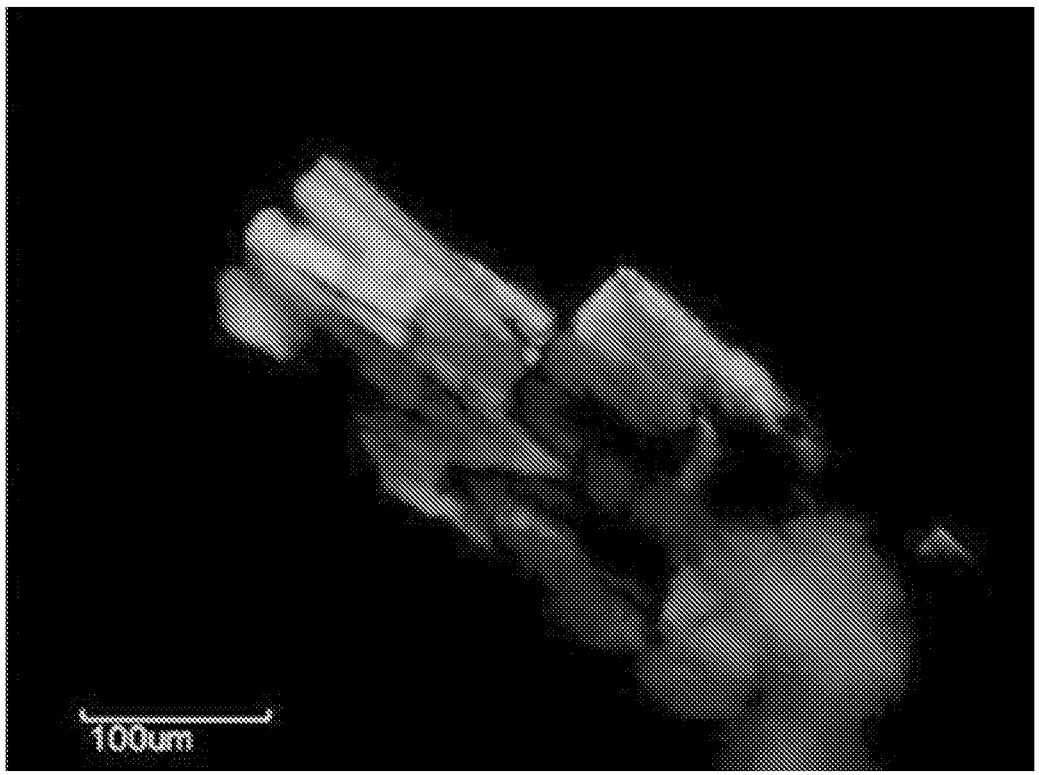
FIG. 5 Polarized-light Microscopy (PLM) of Form II.

Form II is a crystalline hydrate (approximately a monohydrate), consisting of columnar (rod-like) crystals. Single-crystal x-ray analysis shows Form II is a conglomerate, consisting of homochiral crystals (meaning a physical mixture of optically-pure crystals of the individual enantiomers). Form II is slightly hygroscopic, and single-crystal results, although modeled upon the basis of 0.8 moles of water per mole of Anavex2-73, suggest the crystal lattice could potentially hold up to 1.75 moles of water per mole of Anavex2-73, making Form II a likely variable hydrate and less desirable from a pharmaceutical development perspective. FIG. 5 shows a polarized-light microscopy (PLM) of Form II.

Single-Crystal X-Ray Analysis Summary:

Crystal Type: Homochiral

Space Group: Orthorhombic P2$_1$2$_1$2$_1$

Figure 6:
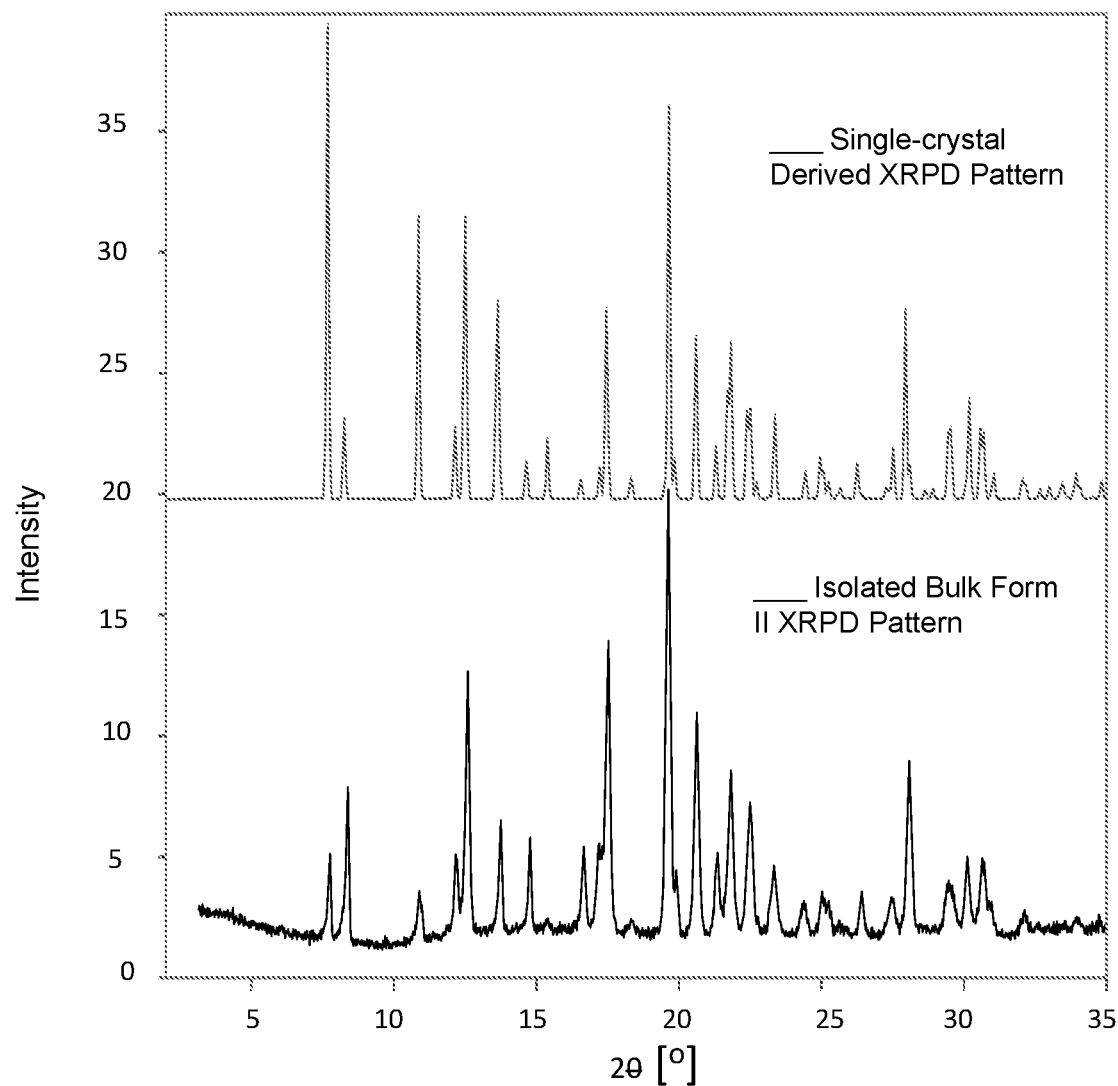
FIG. 6 shows Form II XRPD Pattern obtained using copper Kα radiation vs. single-crystal derived XRPD pattern.

Unit Cell Parameters:

a=7.10738(5) Å α=90.00°
b=14.22620(10) Å β=90.00°
c=17.18510(10) Å γ=90.00°
Volume=1737.608(16) Å$^3$
Z=4, Z'=1
Density (ρcalc)=1.173 g/cm$^3$ XRPD pattern of Anavex2-73 Form II derived from single-crystal results for copper Kα radiation vs. experimentally measured XRPD pattern obtained for an isolated bulk sample of Form II are shown in FIG. 6.

The twenty most intense XRPD peaks for Anavex2-73 Form II, measured using copper Kα radiation are shown in Table 2.

TABLE 2

XRPD peaks for Anavex2-73 Form II

| Pos. [°2θ] | d-spacing [Å] | Rel. Int. [%] |
|---|---|---|
| 7.61 | 11.622 | 19 |
| 8.23 | 10.743 | 34 |
| 10.75 | 8.228 | 11 |
| 12.03 | 7.359 | 19 |
| 12.45 | 7.107 | 60 |
| 13.59 | 6.515 | 26 |
| 14.63 | 6.054 | 23 |
| 16.51 | 5.371 | 20 |
| 17.05 | 5.202 | 20 |
| 17.36 | 5.108 | 66 |
| 19.48 | 4.557 | 100 |
| 19.75 | 4.496 | 14 |
| 20.47 | 4.339 | 50 |
| 21.19 | 4.192 | 18 |
| 21.67 | 4.101 | 37 |
| 22.34 | 3.979 | 30 |
| 23.17 | 3.838 | 16 |
| 27.93 | 3.194 | 39 |
| 29.97 | 2.982 | 17 |
| 30.50 | 2.931 | 17 | c. Form III, Hydrochloride Salt

Figure 7:
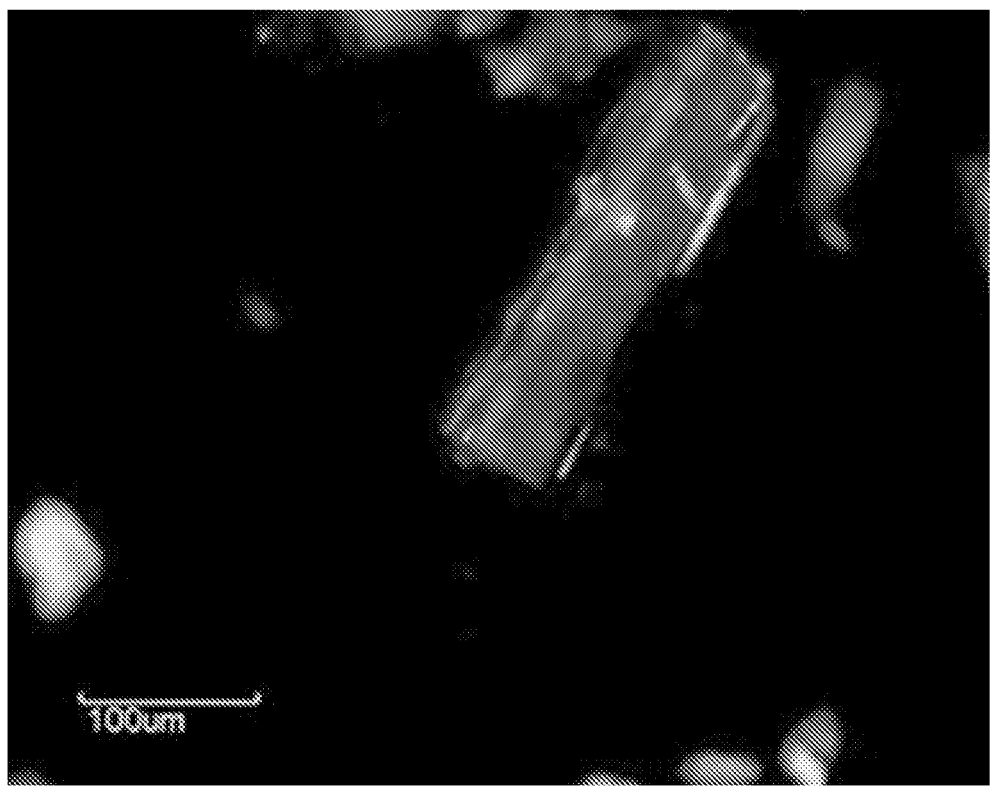
FIG. 7 Polarized-light Microscopy (PLM) of Form III.

Form III is a slightly-hygroscopic, anhydrous, crystalline material, exhibiting a columnar (rod-like) morphology. In some aspects, single-crystal x-ray analysis shows Form III is an optically pure form. In other aspects, single-crystal x-ray analysis shows Form III is a conglomerate, consisting of homochiral crystals (meaning a physical mixture of optically-pure crystals of the individual enantiomers). Form III appears to be the thermodynamically-preferred optically pure form of Anavex2-73. FIG. 7 shows polarized-light microscopy (PLM) of Form III.

Single-Crystal X-Ray Analysis Summary:
Crystal Type: Homochiral
Space Group: Orthorhombic P212121
Unit Cell Parameters:
  a=7.10738(5) Å α=90.00°
  b=14.22620(10) Å β=90.00°
  c=17.18510(10) Å γ=90.00°
  Volume=1737.608(16) Å 3
  Z=4, Z'=1
  Density (ρcalc)=1.215 g/cm3

Figure 8:
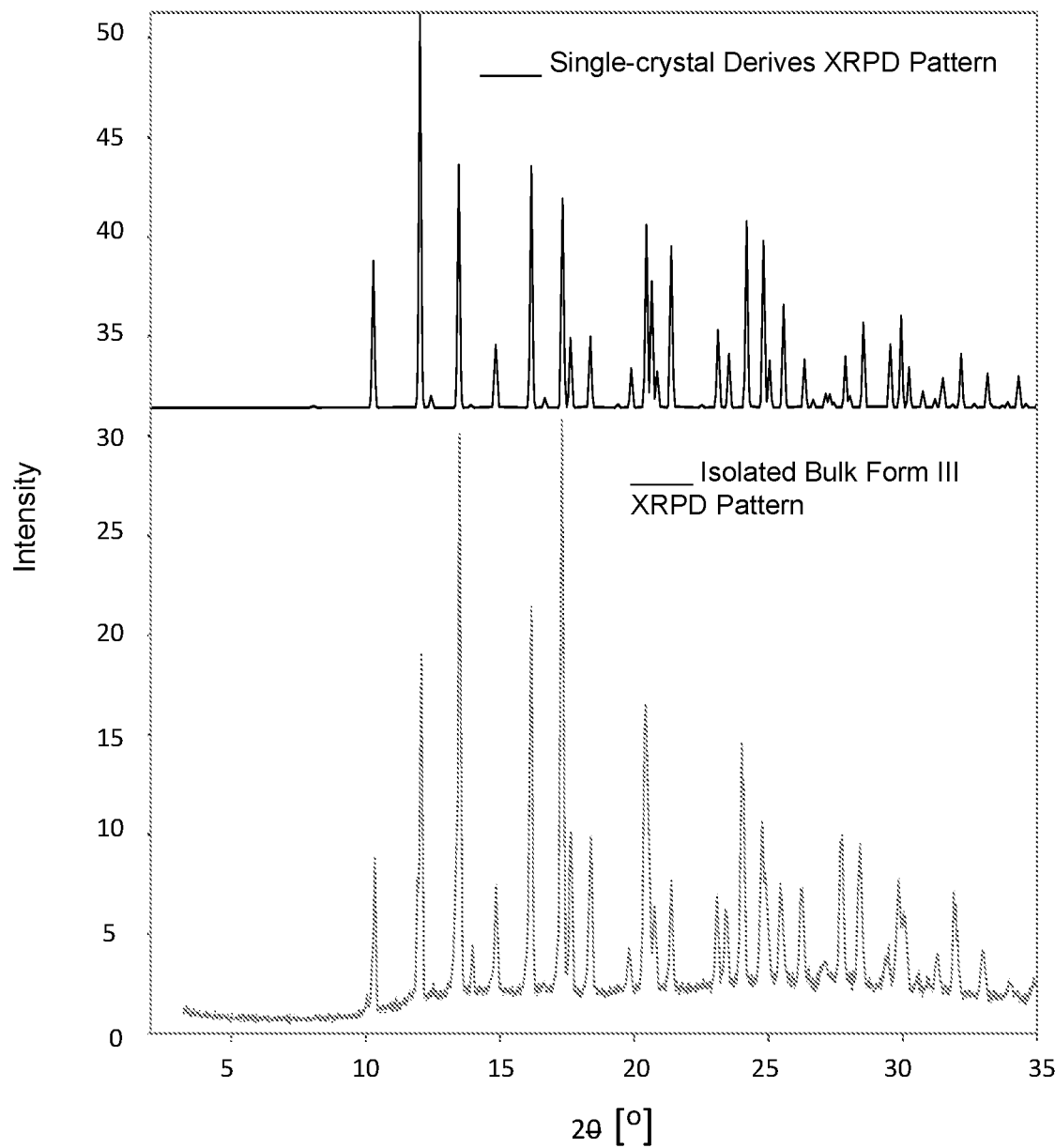
FIG. 8 shows Form III XRPD Pattern obtained using copper Kα radiation vs. single-crystal derived XRPD pattern.

XRPD pattern of Anavex2-73 Form III derived from single-crystal results for copper Kα radiation vs. experimentally measured XRPD pattern obtained for an isolated bulk sample of Form III (FIG. 8).

The twenty most intense XRPD peaks for Anavex2-73 Form III, measured using copper Kα radiation are shown in Table 3.

TABLE 3

XRPD peaks for Anavex2-73 Form III

| Pos. [°2θ] | d-spacing [Å] | Rel. Int. [%] |
|---|---|---|
| 10.14 | 8.721 | 27 |
| 11.72 | 7.550 | 22 |
| 11.87 | 7.455 | 62 |
| 13.30 | 6.657 | 99 |
| 14.67 | 6.041 | 20 |
| 15.97 | 5.551 | 68 |
| 17.10 | 5.185 | 100 |
| 17.43 | 5.088 | 29 |
| 18.19 | 4.877 | 28 |
| 20.23 | 4.390 | 50 |
| 21.19 | 4.193 | 18 |

TABLE 3-continued

XRPD peaks for Anavex2-73 Form III

| Pos. [°2θ] | d-spacing [Å] | Rel. Int. [%] |
|---|---|---|
| 23.81 | 3.734 | 43 |
| 23.88 | 3.727 | 34 |
| 24.56 | 3.625 | 30 |
| 25.23 | 3.530 | 19 |
| 26.00 | 3.427 | 18 |
| 27.49 | 3.242 | 26 |
| 27.55 | 3.237 | 24 |
| 28.21 | 3.163 | 26 |
| 29.65 | 3.013 | 19 | d. Form IV, Hydrochloride Salt

Figure 9:
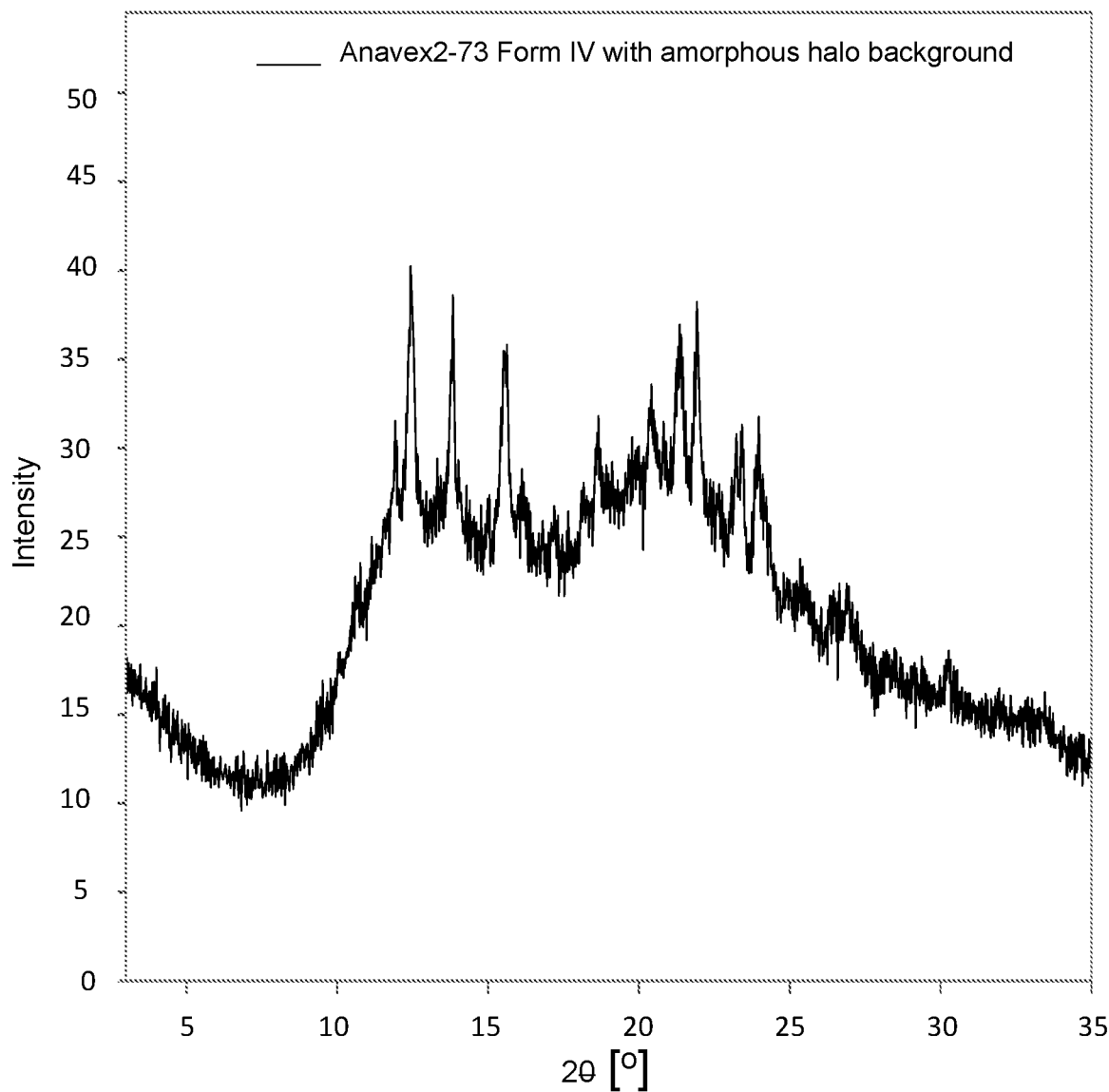
FIG. 9 shows Form IV XRPD Pattern obtained using copper Kα radiation.

Form IV is crystalline and can be isolated as a physical mixture with amorphous material during lyophilization of Anavex2-73 from water. XRPD pattern of Anavex2-73 Form IV obtained using copper Kα radiation is seen in FIG. 9.

The eleven most intense XRPD peaks for Anavex2-73 Form IV, measured using copper Kα radiation are shown in Table 4.

TABLE 4

XRPD peaks for Anavex2-73 Form IV

| Pos. [°2θ] | d-spacing [Å] | Rel. Int. [%] |
|---|---|---|
| 11.92 | 7.424 | 56 |
| 12.45 | 7.111 | 100 |
| 13.83 | 6.403 | 82 |
| 15.57 | 5.691 | 61 |
| 18.65 | 4.759 | 35 |
| 20.42 | 4.350 | 44 |
| 21.35 | 4.161 | 57 |
| 21.94 | 4.052 | 70 |
| 23.37 | 3.807 | 37 |
| 23.95 | 3.716 | 41 |
| 26.74 | 3.334 | 10 | e. Form V, Hydrochloride Salt

Figure 10:
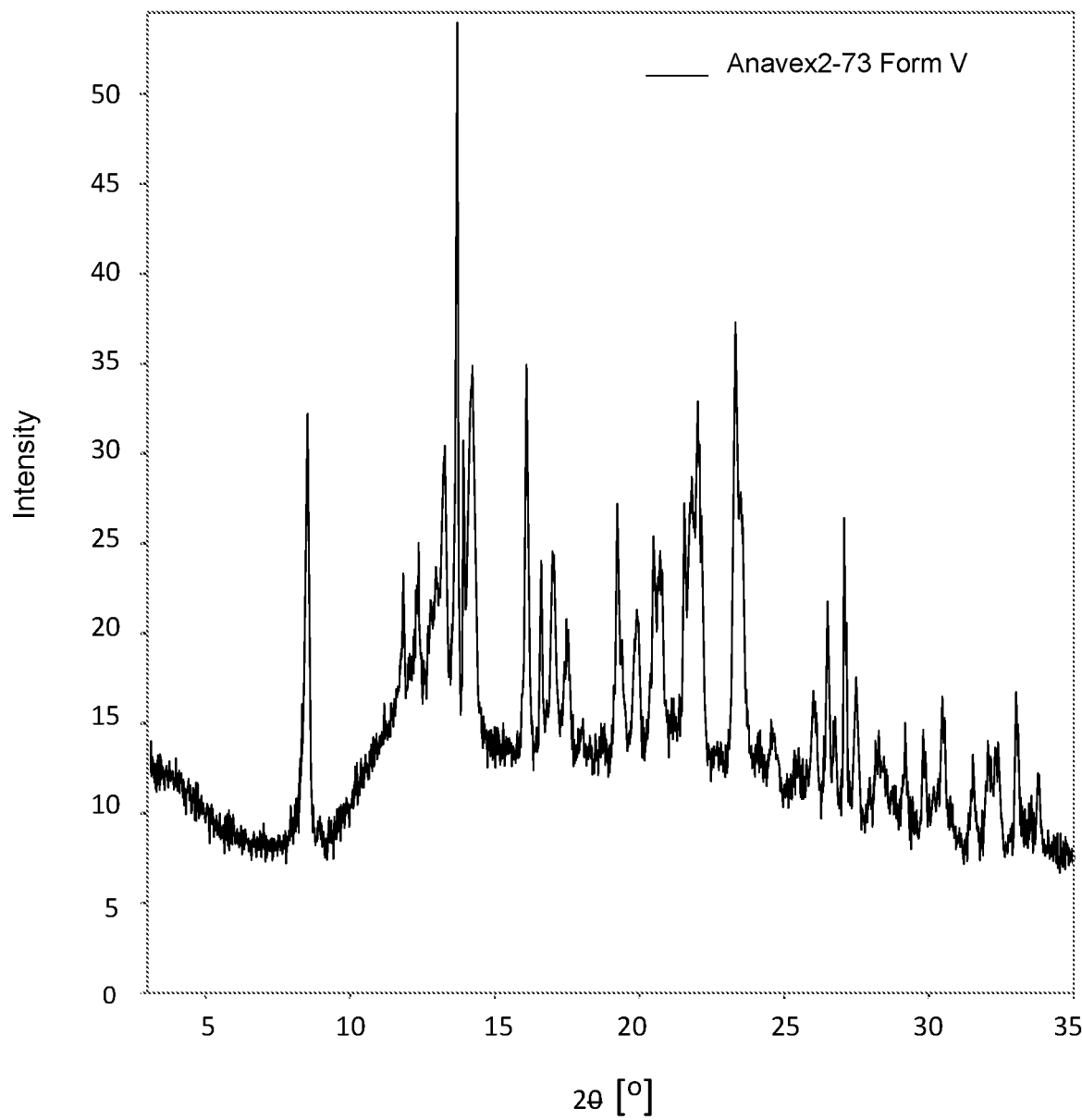
FIG. 10 shows Form V XRPD Pattern obtained using copper Kα radiation.

Form V is crystalline and can be isolated upon rotary evaporation of Anavex2-73 from dichloromethane. XRPD pattern of Anavex2-73 Form V obtained using copper Kα radiation can be seen in FIG. 10. The twenty most intense XRPD peaks for Anavex2-73 Form V, measured using copper Kα radiation are as shown in Table 5.

TABLE 5

| Pos. [°2θ] | d-spacing [Å] | Rel. Int. [%] |
|---|---|---|
| 8.43 | 10.494 | 54 |
| 11.74 | 7.541 | 30 |
| 12.23 | 7.235 | 29 |
| 12.99 | 6.815 | 28 |
| 13.15 | 6.731 | 44 |
| 13.60 | 6.513 | 100 |
| 13.82 | 6.406 | 42 |
| 14.13 | 6.268 | 55 |
| 15.99 | 5.544 | 53 |
| 16.50 | 5.374 | 28 |
| 16.92 | 5.239 | 28 |
| 19.14 | 4.638 | 34 |
| 20.40 | 4.354 | 29 |
| 20.61 | 4.310 | 29 |
| 21.44 | 4.144 | 36 |
| 21.69 | 4.098 | 39 |
| 21.92 | 4.055 | 46 |
| 23.21 | 3.833 | 60 |
| 23.40 | 3.801 | 36 |
| 26.97 | 3.306 | 38 | f. Form VI, Hydrochloride Salt

Figure 11:
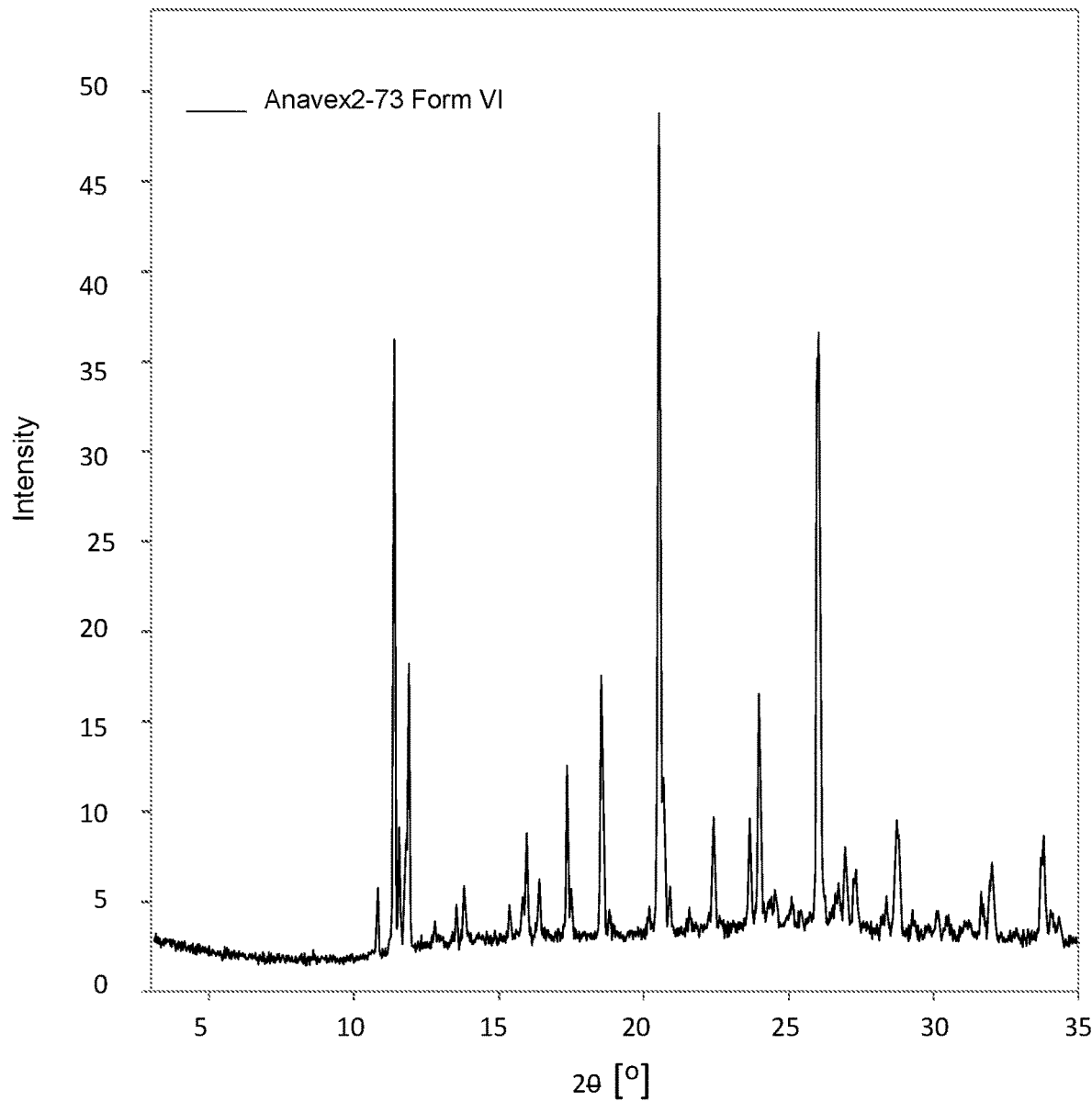
FIG. 11 shows Form VI XRPD Pattern obtained using copper Kα radiation.

Form VI is crystalline and was isolated upon rapid cooling of an aqueous solution of Anavex2-73 to 5° C. XRPD pattern of Anavex2-73 Form VI obtained using copper Kα radiation is seen in FIG. 11.

The twenty most intense XRPD peaks for Anavex2-73 Form VI, measured using copper Kα radiation are as shown in Table 6.

TABLE 6

XRPD peaks for Anavex2-73 Form VI

| Pos. [°2θ] | d-spacing [Å] | Rel. Int. [%] |
|---|---|---|
| 10.72 | 8.253 | 8 |
| 11.29 | 7.836 | 75 |
| 11.46 | 7.723 | 15 |
| 11.79 | 7.506 | 35 |
| 15.85 | 5.591 | 13 |
| 16.30 | 5.439 | 8 |
| 17.26 | 5.138 | 21 |
| 18.45 | 4.810 | 32 |
| 20.43 | 4.347 | 100 |
| 20.59 | 4.314 | 18 |
| 22.30 | 3.986 | 15 |
| 23.55 | 3.778 | 14 |
| 23.86 | 3.730 | 29 |
| 25.89 | 3.438 | 70 |
| 25.94 | 3.435 | 73 |
| 26.84 | 3.322 | 10 |
| 28.65 | 3.116 | 13 |
| 31.90 | 2.806 | 9 |
| 33.60 | 2.665 | 11 |
| 33.68 | 2.661 | 13 | g. Form VII, Hydrochloride Salt

Figure 12:
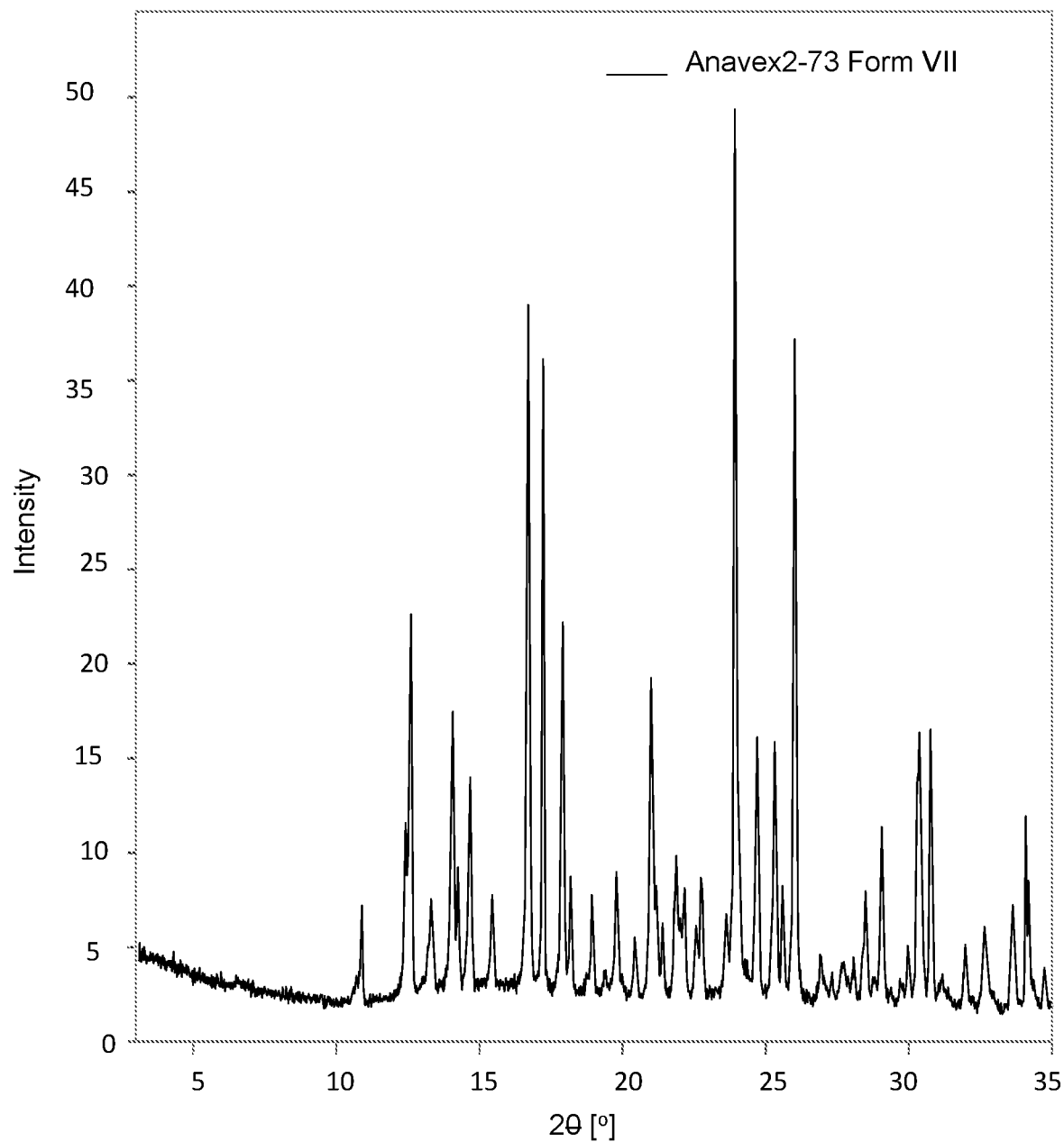
FIG. 12 shows Form VII XRPD Pattern obtained using copper Kα radiation.

Form VII is both crystalline and anhydrous, and it was isolated via air evaporation of Anavex2-73 from methanol. XRPD pattern of Anavex2-73 Form VII obtained using copper Kα radiation is shown in FIG. 12. The twenty most intense XRPD peaks for Anavex2-73 Form VII, measured using copper Kα radiation are shown in Table 7.

TABLE 7

XRPD peaks for Anavex2-73 Form VII

| Pos. [°2θ] | d-spacing [Å] | Rel. Int. [%] |
|---|---|---|
| 12.32 | 7.184 | 20 |
| 12.51 | 7.076 | 43 |
| 13.91 | 6.360 | 25 |
| 13.97 | 6.338 | 33 |
| 14.15 | 6.260 | 15 |
| 14.58 | 6.076 | 25 |
| 16.61 | 5.338 | 78 |
| 17.12 | 5.179 | 73 |
| 17.81 | 4.982 | 42 |
| 20.90 | 4.251 | 36 |
| 21.77 | 4.082 | 16 |
| 23.82 | 3.736 | 100 |
| 24.60 | 3.619 | 30 |
| 25.21 | 3.532 | 29 |
| 25.91 | 3.439 | 75 |
| 28.95 | 3.085 | 19 |
| 30.19 | 2.958 | 24 |
| 30.26 | 2.953 | 30 |
| 30.66 | 2.914 | 31 |
| 33.99 | 2.636 | 21 | h. Form VIII, Hydrochloride Salt

Figure 13:
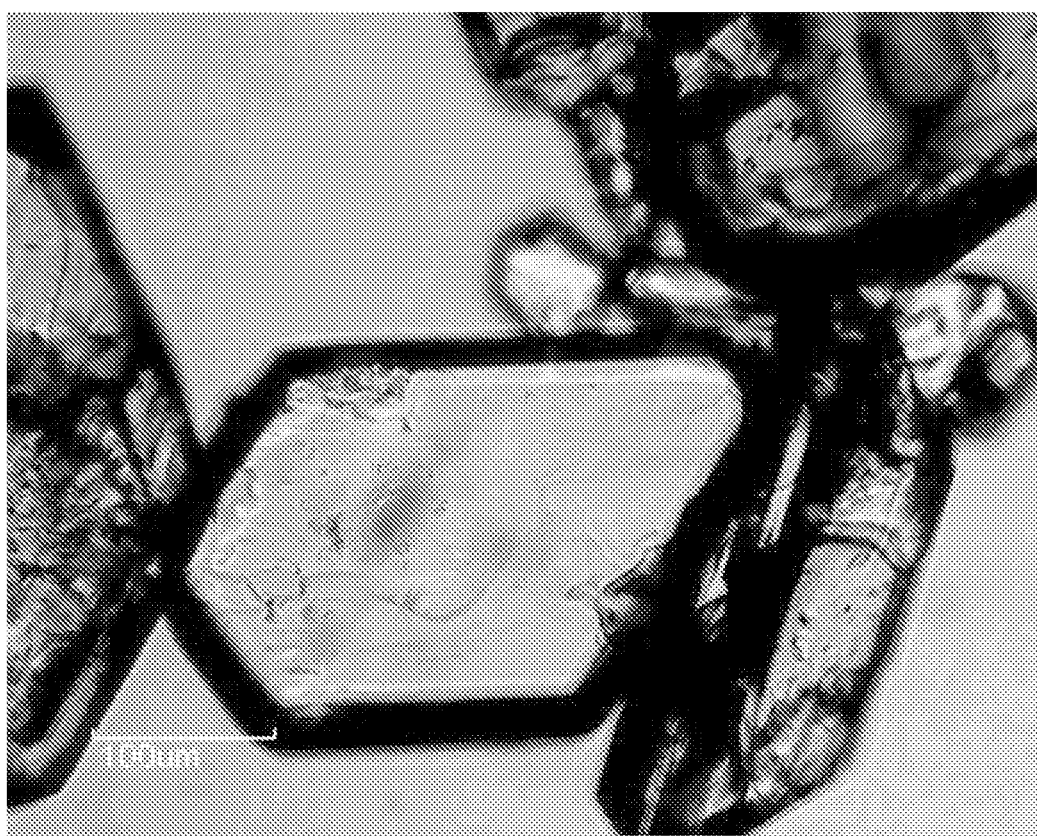
FIG. 13 Polarized-light Microscopy (PLM) of Form VIII.

Form VIII is a trihydrated, crystalline form of Anavex2-73. Single-crystal x-ray analysis shows Form VIII consists of racemic crystals, meaning each individual crystal contains both enantiomers. Without being bound by any particular theory, it is believed that Form VIII is a layer or channel hydrate, with the water of hydration being weakly associated and readily removed by grinding, drying, etc. The resulting material, a dehydrated lattice, is labile, quickly collapsing into Form I. FIG. 13 is a polarized-light microscopy (PLM) of Form VIII.

Figure 14:
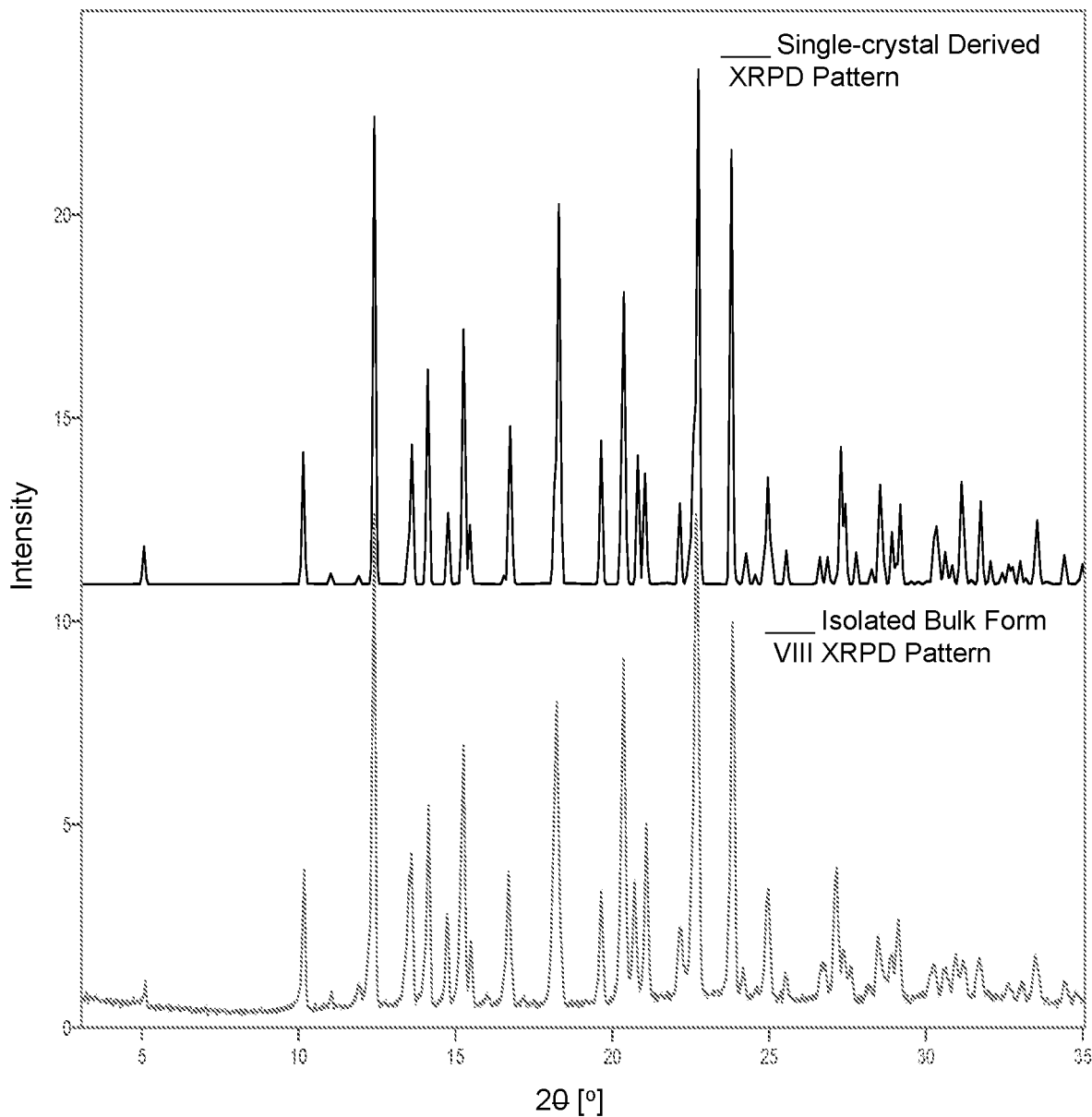
FIG. 14 shows Form VIII XRPD Pattern obtained using copper Kα radiation vs. single-crystal derived XRPD pattern.

Single-Crystal X-Ray Analysis Summary:
Crystal Type: Racemic
Space Group: Monoclinic P2$_1$/c
Unit Cell Parameters:
a=17.7753(11) Å   α=90.00°
b=9.0306(4) Å   β=101.535(5)°
c=13.2638(5) Å   γ=90.00°
Volume=2086.12(12) Å$^3$
Z=4, Z'=1
Density (ρcalc)=1.184 g/cm$^3$ XRPD pattern of Anavex2-73 Form VIII derived from single-crystal results for copper Kα radiation vs. experimentally measured XRPD pattern obtained for an isolated bulk sample of Form VIII is shown in FIG. 14. The twenty most intense XRPD peaks for Anavex2-73 Form VIII, measured using copper Kα radiation are shown in Table 8.

TABLE 8

XRPD peaks for Anavex2-73 Form VIII

| Pos. [°2θ] | d-spacing [Å] | Rel. Int. [%] |
|---|---|---|
| 10.13 | 8.733 | 28 |
| 12.37 | 7.158 | 100 |
| 13.56 | 6.532 | 32 |
| 14.09 | 6.286 | 41 |
| 14.70 | 6.028 | 18 |
| 15.20 | 5.828 | 52 |
| 16.65 | 5.325 | 27 |
| 18.18 | 4.881 | 61 |
| 19.60 | 4.530 | 23 |
| 20.31 | 4.374 | 70 |
| 20.67 | 4.298 | 25 |
| 21.04 | 4.222 | 37 |
| 22.12 | 4.018 | 15 |
| 22.64 | 3.924 | 96 |
| 22.69 | 3.925 | 75 |
| 23.78 | 3.738 | 77 |
| 24.92 | 3.570 | 23 |
| 27.04 | 3.295 | 23 |
| 27.09 | 3.288 | 25 |
| 29.07 | 3.069 | 17 | i. Form I, Freebase

Figure 15:
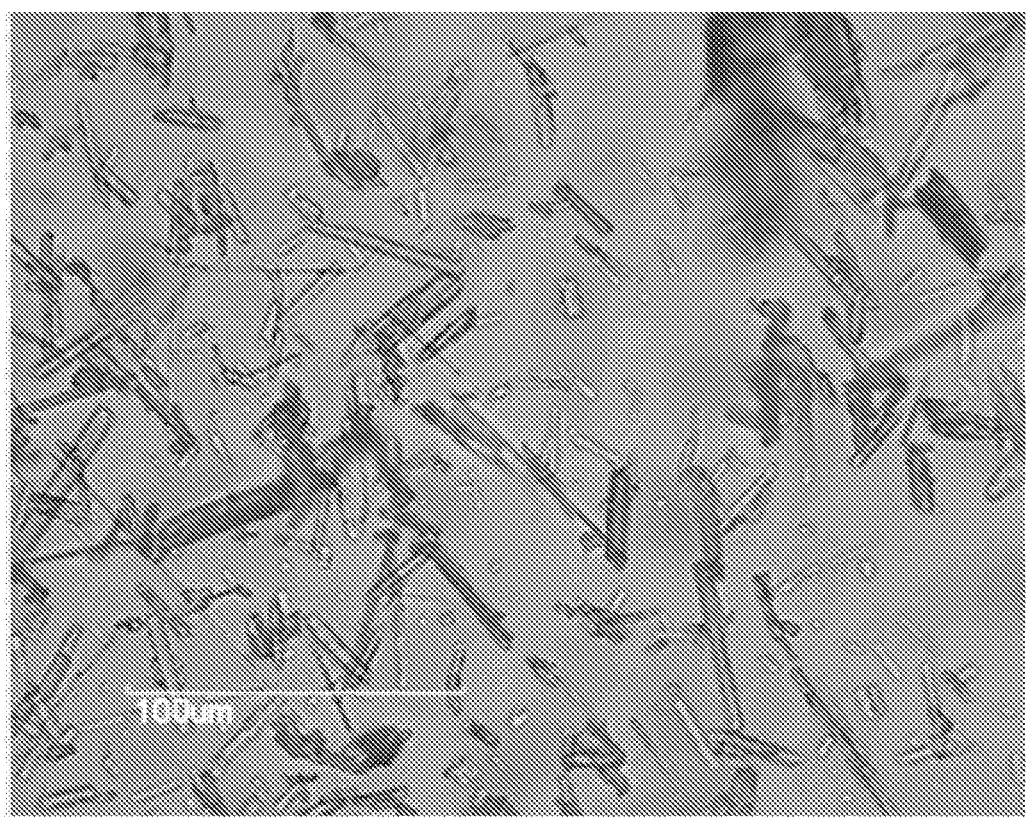
FIG. 15 Non-Polarized-light Microscopy (PLM) of Freebase Form I.
Figure 16:
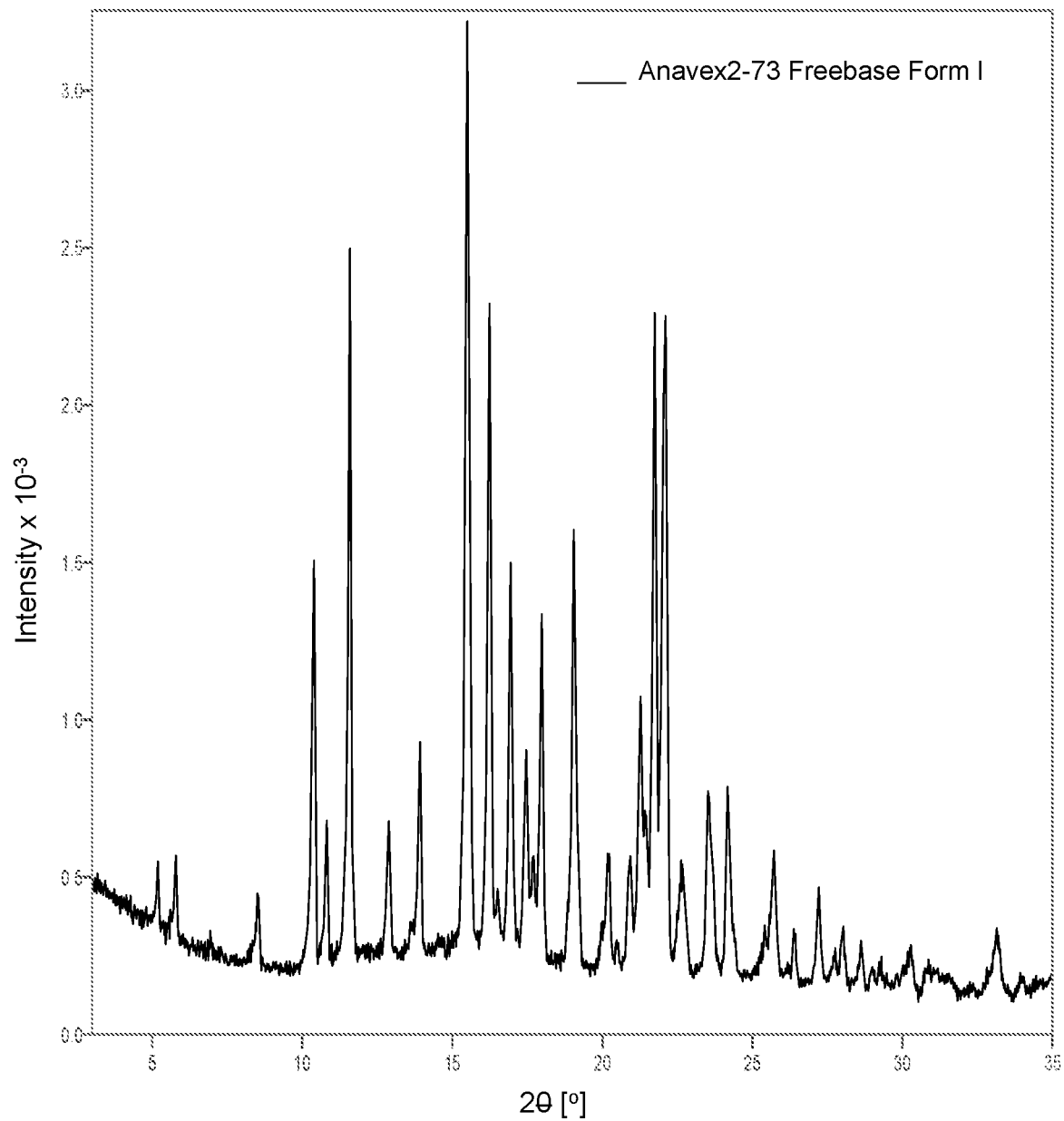
FIG. 16 XRPD pattern of Anavex2-73 freebase Form I obtained using copper Kα radiation.

A2-73 freebase Form I is crystalline by XRPD and PLM, exhibiting highly-birefringent agglomerates of columnar (rod-like) crystals. Thermogravimetric analysis (TGA) showed no significant weight loss until post-melting, indicating Form I is anhydrous. This is confirmed by gravimetric vapor sorption (GVS) analysis, showing minimal water update (0.3% w/w) up to 90% RH. XRPD analysis post-GVS showed no change in form. Differential scanning calorimetry (DSC) shows a sharp melting endotherm at an onset of ca. 89° C. (peak temperature at ca. 91° C.). Upon further heating, Form I appears to sublime, beginning above ca. 120° C. with a weight loss of ca. 99% observed by 212.6° C. $^1$H NMR spectra and HPLC-MS results were consistent with the structure of A2-73 freebase. A2-73 freebase was shown to have an HPLC purity of 99.9%, and CAD analysis confirmed the absence of chloride within the sample. FIG. 15 is a non-polarized-light microscopy (PLM) of Freebase Form I. XRPD pattern of Anavex2-73 freebase Form I obtained using copper Kα radiation is shown in FIG. 16.

The twenty most intense XRPD peaks for Anavex2-73 freebase Form I, measured using copper Kα radiation are shown in Table 9.

TABLE 9

XRPD peaks for Anavex2-73 freebase Form I

| Pos. [°2θ] | d-spacing [Å] | Rel. Int. [%] |
|---|---|---|
| 10.38 | 8.519 | 43 |
| 10.82 | 8.177 | 15 |
| 11.59 | 7.634 | 76 |
| 12.89 | 6.870 | 15 |
| 13.91 | 6.365 | 23 |
| 15.50 | 5.717 | 100 |
| 16.24 | 5.460 | 70 |
| 16.95 | 5.232 | 43 |
| 17.46 | 5.078 | 23 |
| 17.70 | 5.012 | 11 |
| 17.98 | 4.935 | 37 |
| 19.06 | 4.657 | 46 |
| 20.21 | 4.395 | 12 |
| 20.93 | 4.244 | 12 |
| 21.27 | 4.178 | 29 |
| 21.73 | 4.089 | 70 |
| 22.09 | 4.023 | 69 |
| 23.53 | 3.781 | 19 |
| 24.18 | 3.681 | 20 |
| 25.71 | 3.465 | 13 |

Solubility:

A2-73 freebase, surprisingly, exhibited high solubility in all solvents tested, except water, as shown in Table 10, below.

TABLE 10

Solvent Solubility Screen Results

| | Solvent | Approx. Solubility (mg/mL) |
|---|---|---|
| 1 | 1,4-Dioxane | ≥200 |
| 2 | 1-Butanol | ≥200 |
| 3 | 1-Propanol | 100 ≥ x ≥ 67 |
| 4 | 2-Butanone | ≥200 |
| 5 | 2-Ethoxyethanol | 200 ≥ x ≥ 100 |
| 6 | 2-Propanol | 200 ≥ x ≥ 100 |
| 7 | Acetone | ≥200 |
| 8 | Acetonitrile | 67 ≥ x ≥ 50 |
| 9 | Cyclohexane | ≥200 |
| 10 | Cyclohexanone | 200 ≥ x ≥ 100 |
| 11 | Dichloromethane | 200 ≥ x ≥ 100 |
| 12 | Dimethyl sulfoxide | ≥200 |
| 13 | Ethanol | 200 ≥ x ≥ 100 |
| 14 | Ethyl Acetate | 200 ≥ x ≥ 100 |
| 15 | Heptane | ≥200 |
| 16 | Isopropyl acetate | 67 ≥ x ≥ 50 |
| 17 | Methanol | 200 ≥ x ≥ 100 |
| 18 | Methyl Acetate | ≥200 |
| 19 | Methyl isobutyl ketone | ≥200 |
| 20 | N, N'-Dimethylformamide | ≥200 |
| 21 | Nitromethane | ≥200 |
| 22 | t-Butylmethyl ether | 200 ≥ x ≥ 100 |
| 23 | Tetrahydrofuran | ≥200 |
| 24 | Water | <5 | j. Sulfate Form I

A2-73 sulfate Form I is crystalline and melts at a DSC onset temperature of ca. 184° C. Form I consisted of highly-birefringent crystals. Its PLM and XRPD pattern are provided below.

Figure 17:
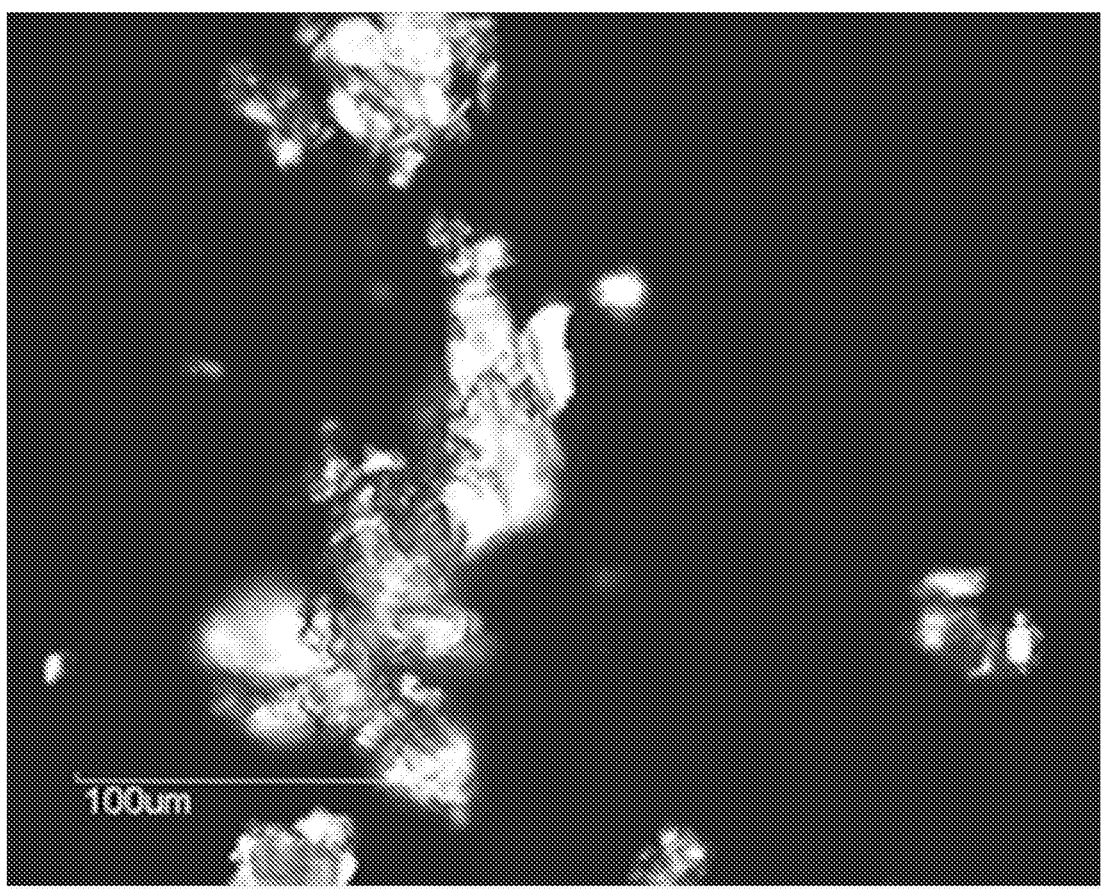
FIG. 17 Polarized-light Microscopy (PLM) of Anavex2-73 sulfate Form I.
Figure 18:
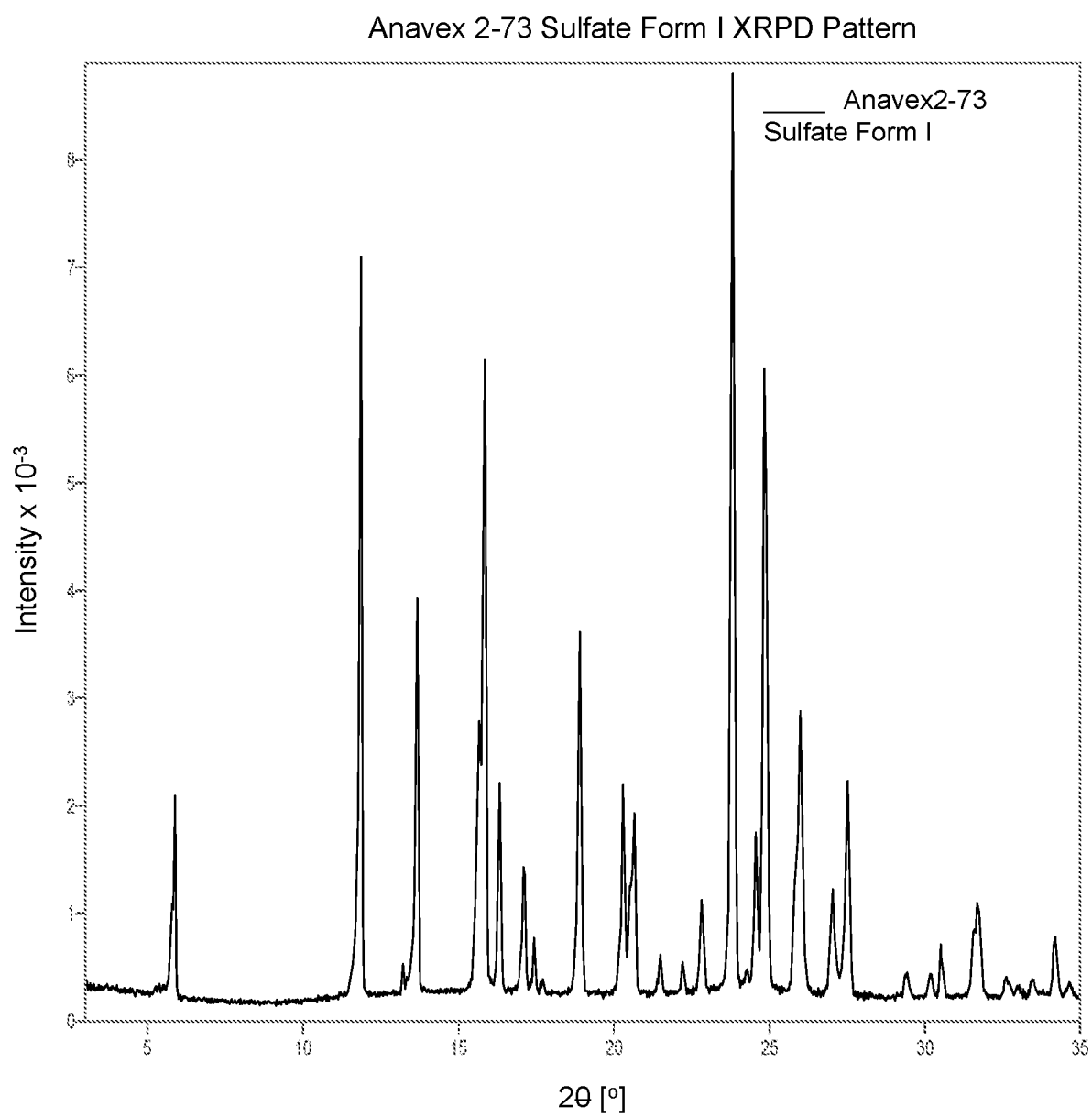
FIG. 18 XRPD pattern of Anavex2-73 sulfate Form I obtained using copper Kα radiation.

FIG. 17 is a polarized-light microscopy (PLM) of Anavex2-73 sulfate Form I. XRPD pattern of Anavex2-73 sulfate Form I obtained using copper Kα radiation is shown in FIG. 18. The twenty most intense XRPD peaks for Anavex2-73 sulfate Form I, measured using copper Kα radiation are shown in Table 11.

TABLE 11

XRPD peaks for Anavex2-73 sulfate Form I

| Pos. [°2θ] | d-spacing [Å] | Rel. Int. [%] |
|---|---|---|
| 5.88 | 15.020 | 21 |
| 11.85 | 7.466 | 81 |
| 13.66 | 6.483 | 42 |
| 15.67 | 5.657 | 31 |
| 15.78 | 5.612 | 52 |
| 15.84 | 5.596 | 69 |
| 16.32 | 5.431 | 23 |
| 17.11 | 5.181 | 14 |
| 18.91 | 4.692 | 40 |
| 20.30 | 4.375 | 23 |
| 20.52 | 4.329 | 12 |
| 20.65 | 4.302 | 20 |
| 23.82 | 3.736 | 100 |
| 24.56 | 3.625 | 18 |
| 24.84 | 3.581 | 69 |
| 24.90 | 3.581 | 52 |
| 25.80 | 3.450 | 12 |
| 25.98 | 3.426 | 31 |
| 27.03 | 3.296 | 12 |
| 27.51 | 3.240 | 24 | k. Sulfate Form II

Figure 19:
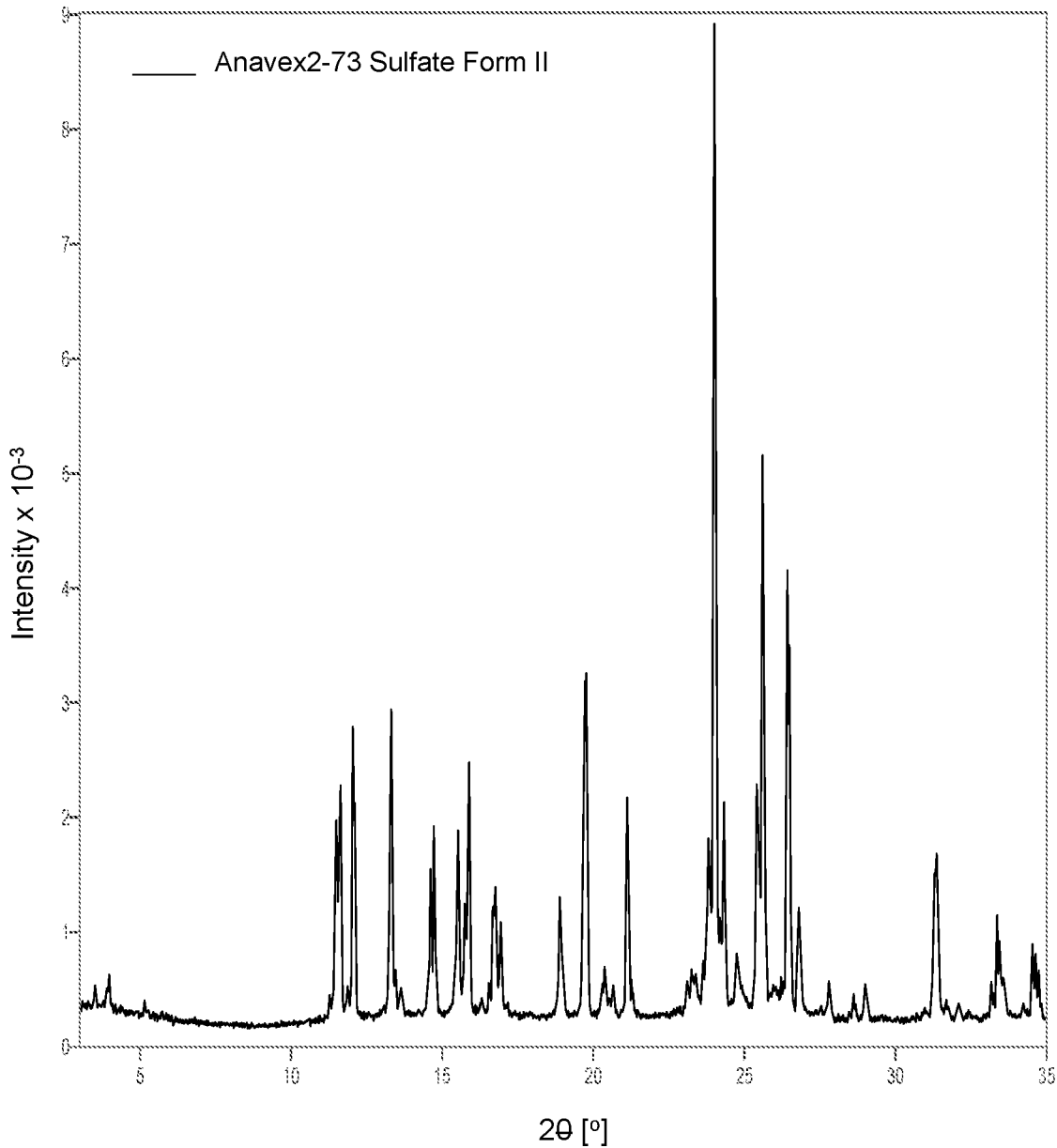
FIG. 19 Anavex2-73 Sulfate Form II XRPD Pattern.

A2-73 sulfate Form II is crystalline and melts at a DSC onset temperature of ca. 190° C. Form II appears to be metastable, converting to A2-73 sulfate Form I post-storage at 40° C./75% RH. Its XRPD pattern, obtained using copper Kα radiation is provided in FIG. 19. The twenty most intense XRPD peaks for Anavex2-73 sulfate Form II, measured using copper Kα radiation are shown in Table 12.

TABLE 12

XRPD peaks for Anavex2-73 sulfate Form II

| Pos. [°2θ] | d-spacing [Å] | Rel. Int. [%] |
|---|---|---|
| 11.50 | 7.697 | 20 |
| 11.64 | 7.606 | 24 |
| 12.05 | 7.347 | 30 |
| 12.11 | 7.306 | 18 |
| 13.32 | 6.647 | 31 |
| 14.73 | 6.015 | 18 |
| 15.53 | 5.707 | 19 |
| 15.89 | 5.577 | 26 |
| 19.65 | 4.514 | 19 |
| 19.75 | 4.495 | 33 |
| 21.12 | 4.206 | 22 |
| 23.81 | 3.737 | 18 |
| 24.00 | 3.704 | 100 |
| 24.07 | 3.704 | 60 |
| 24.32 | 3.657 | 22 |
| 25.42 | 3.501 | 22 |
| 25.60 | 3.476 | 57 |
| 25.67 | 3.476 | 30 |
| 26.42 | 3.370 | 45 |
| 26.48 | 3.363 | 37 | l. Mesylate Form I

Figure 20:
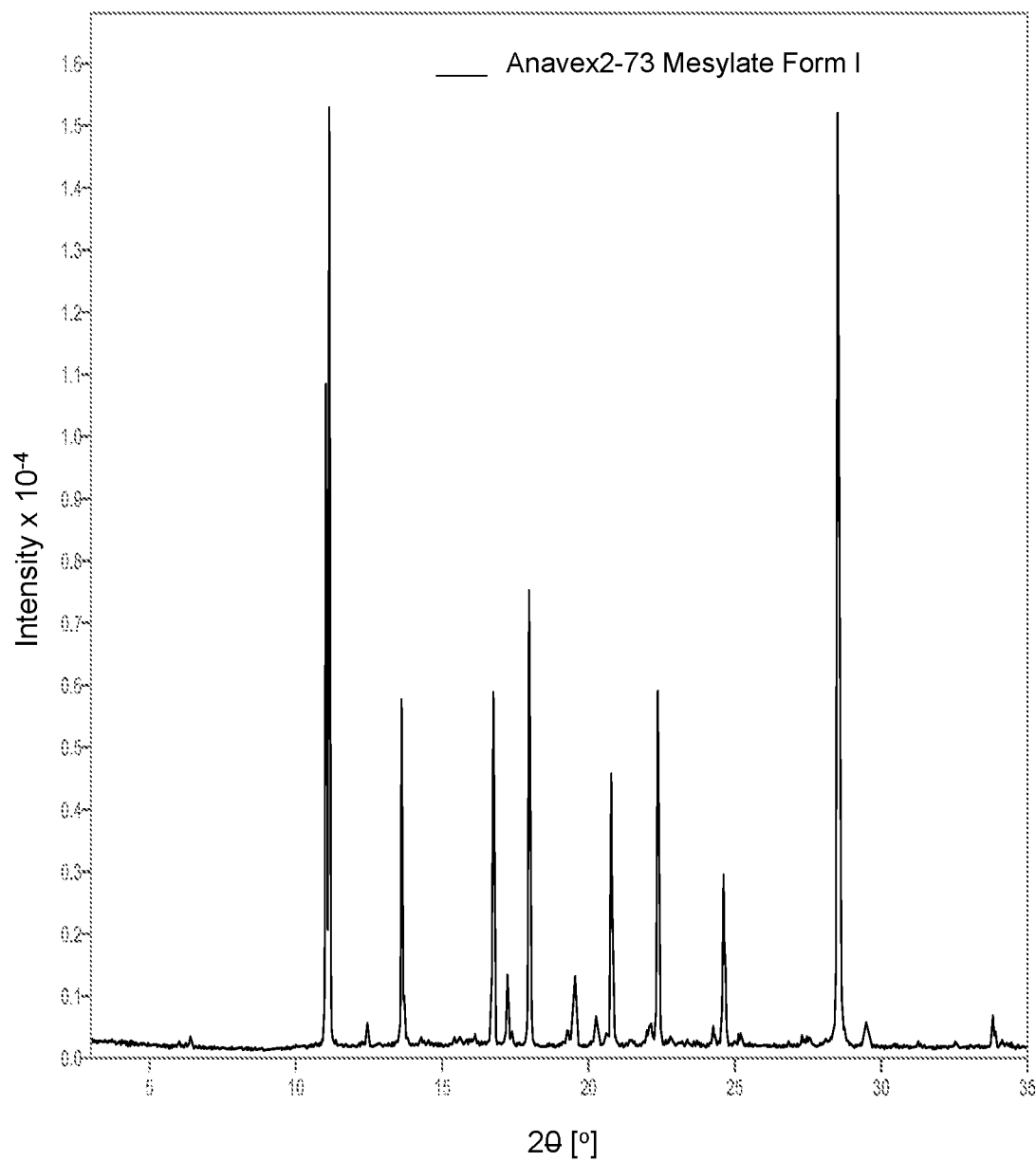
FIG. 20 Anavex2-73 Mesylate Form I XRPD Pattern.

A2-73 mesylate Form I is crystalline and melts at a DSC onset temperature of ca. 159° C. Its XRPD pattern, obtained using copper Kα radiation is provided in FIG. 20.

The twenty most intense XRPD peaks for Anavex2-73 mesylate Form I, measured using copper Kα radiation are shown in Table 13.

TABLE 13

XRPD peaks for Anavex2-73 mesylate Form I

| Pos. [°2θ] | d-spacing [Å] | Rel. Int. [%] |
|---|---|---|
| 11.03 | 8.019 | 72 |
| 11.15 | 7.938 | 99 |
| 12.45 | 7.110 | 3 |
| 13.62 | 6.500 | 36 |
| 16.75 | 5.294 | 38 |
| 17.23 | 5.145 | 8 |
| 17.98 | 4.934 | 48 |
| 19.54 | 4.543 | 8 |
| 20.26 | 4.382 | 3 |
| 20.78 | 4.275 | 29 |
| 22.04 | 4.030 | 2 |
| 22.13 | 4.024 | 2 |
| 22.37 | 3.972 | 38 |
| 22.43 | 3.971 | 17 |
| 24.26 | 3.666 | 2 |
| 24.62 | 3.614 | 19 |
| 28.51 | 3.128 | 100 |
| 28.59 | 3.128 | 50 |
| 29.49 | 3.027 | 3 |
| 33.81 | 2.649 | 3 | m. Oxalate Form I

Figure 21:
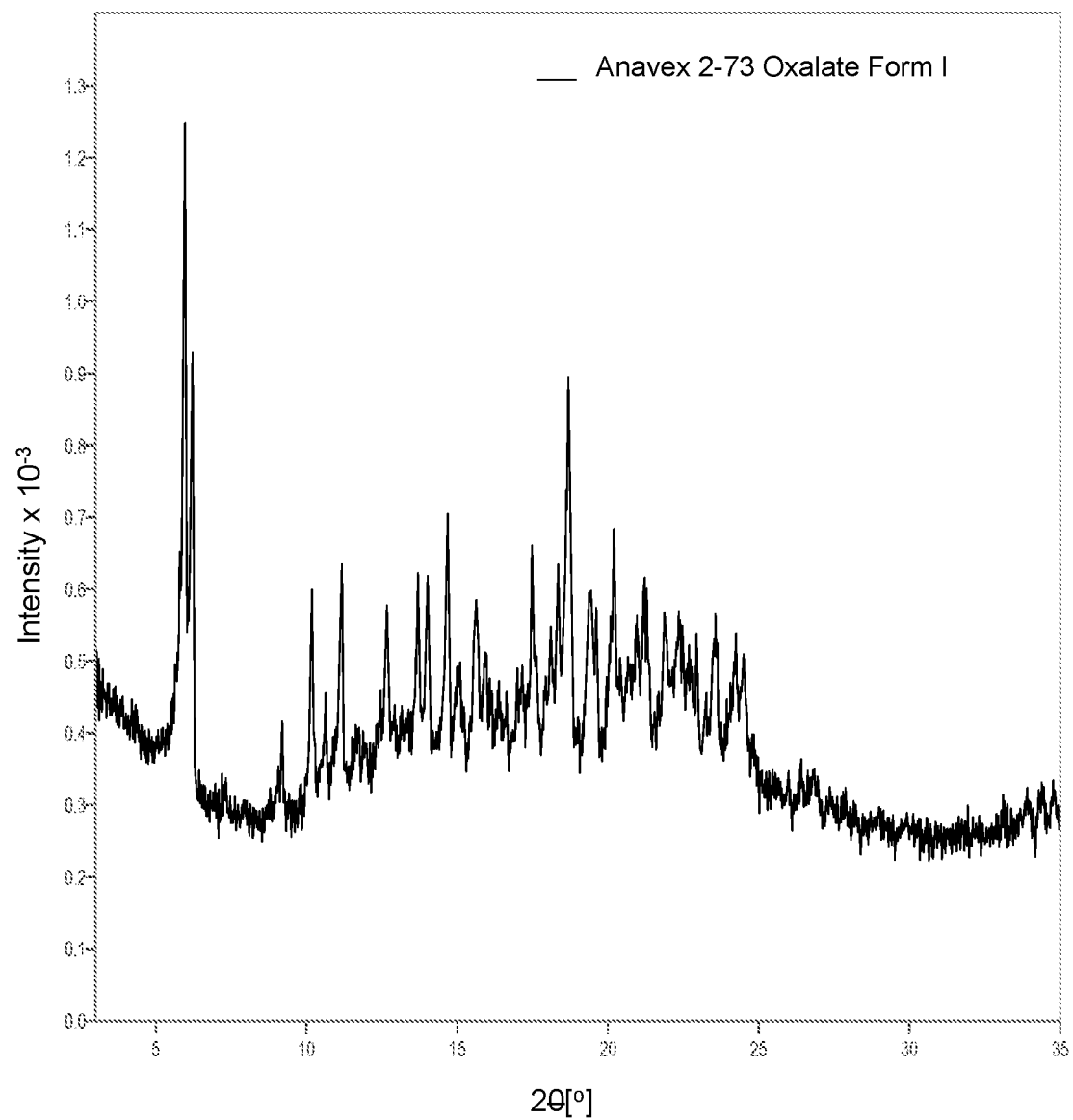
FIG. 21 Anavex2-73 Oxalate Form I XRPD Pattern.

A2-73 oxalate Form I is crystalline. Its XRPD pattern, obtained using copper Kα radiation is provided in FIG. 21. The twenty most intense XRPD peaks for Anavex2-73 oxalate Form I, measured using copper Kα radiation are shown in Table 14.

TABLE 14

XRPD peaks for Anavex2-73 oxalate Form I

| Pos. [°2θ] | d-spacing [Å] | Rel. Int. [%] |
|---|---|---|
| 5.96 | 14.822 | 100 |
| 6.22 | 14.212 | 68 |
| 10.18 | 8.693 | 35 |
| 11.17 | 7.924 | 38 |
| 12.68 | 6.983 | 31 |
| 13.71 | 6.460 | 37 |
| 14.01 | 6.320 | 36 |
| 14.68 | 6.036 | 46 |
| 15.63 | 5.671 | 32 |
| 17.48 | 5.074 | 40 |
| 18.11 | 4.899 | 27 |
| 18.34 | 4.837 | 36 |
| 18.68 | 4.750 | 65 |
| 19.41 | 4.574 | 32 |
| 19.61 | 4.528 | 29 |
| 20.20 | 4.397 | 41 |
| 21.19 | 4.193 | 33 |
| 21.90 | 4.059 | 28 |
| 22.38 | 3.973 | 26 |
| 23.56 | 3.776 | 26 | n. Oxalate Form II

Figure 22:
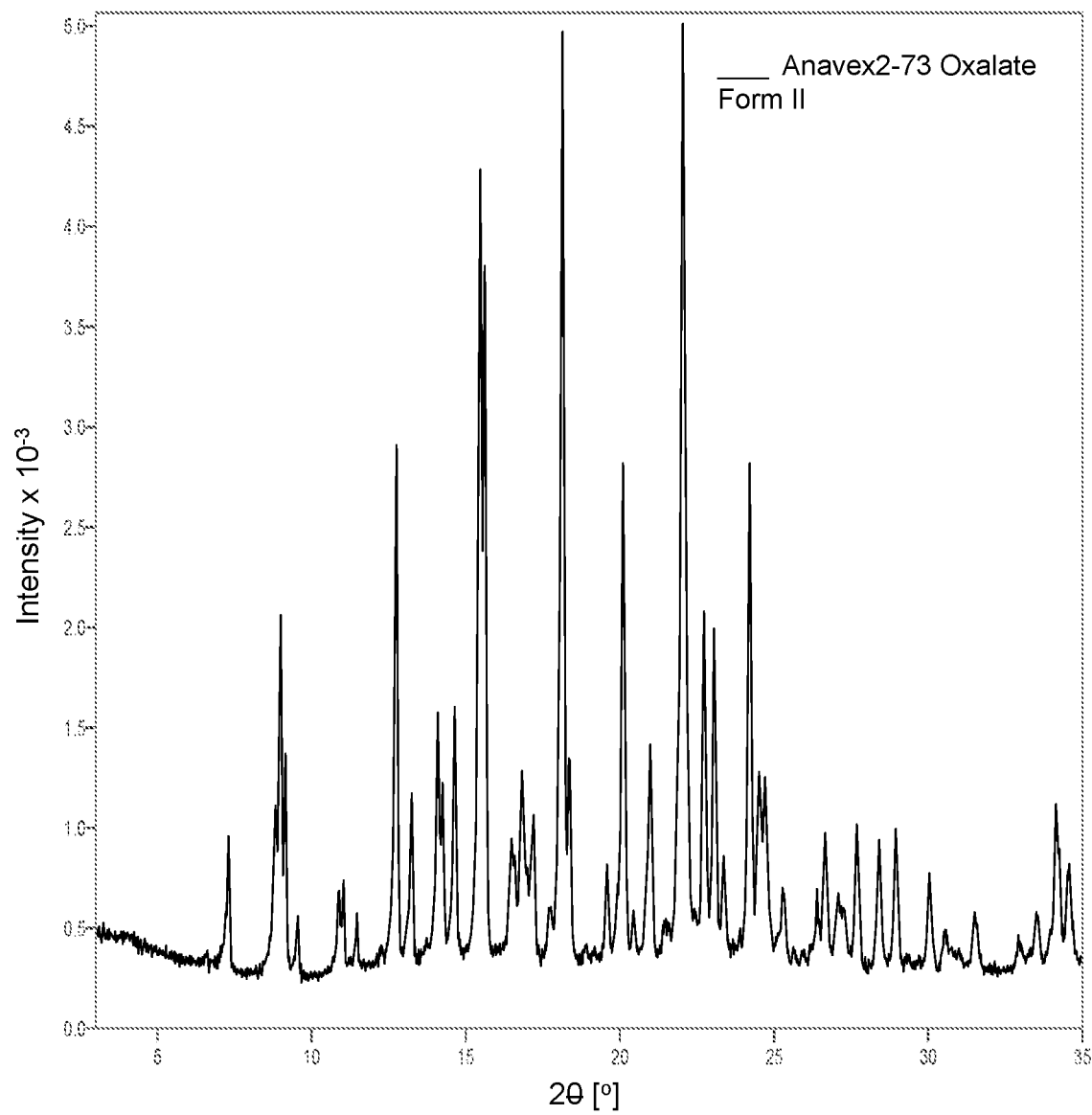
FIG. 22 Anavex2-73 Oxalate Form II XRPD Pattern.

A2-73 oxalate Form II is crystalline. Its XRPD pattern, obtained using copper Kα radiation is provided in FIG. 22. The twenty most intense XRPD peaks for Anavex2-73 oxalate Form II, measured using copper Kα radiation in Table 15.

TABLE 15

XRPD peaks for Anavex2-73 oxalate Form II

| Pos. [°2θ] | d-spacing [Å] | Rel. Int. [%] |
|---|---|---|
| 9.00 | 9.825 | 38 |
| 9.16 | 9.657 | 23 |
| 12.76 | 6.940 | 56 |
| 13.25 | 6.683 | 19 |
| 14.10 | 6.283 | 28 |
| 14.25 | 6.217 | 20 |
| 14.64 | 6.049 | 28 |
| 15.47 | 5.728 | 85 |
| 15.62 | 5.674 | 75 |
| 16.82 | 5.270 | 21 |
| 18.14 | 4.891 | 99 |
| 18.36 | 4.833 | 23 |
| 20.11 | 4.415 | 54 |
| 20.99 | 4.233 | 24 |
| 22.04 | 4.033 | 100 |
| 22.73 | 3.913 | 38 |
| 23.06 | 3.857 | 36 |
| 24.20 | 3.678 | 53 |
| 24.51 | 3.632 | 21 |
| 24.70 | 3.604 | 21 | o. Oxalate Form III

Figure 23:
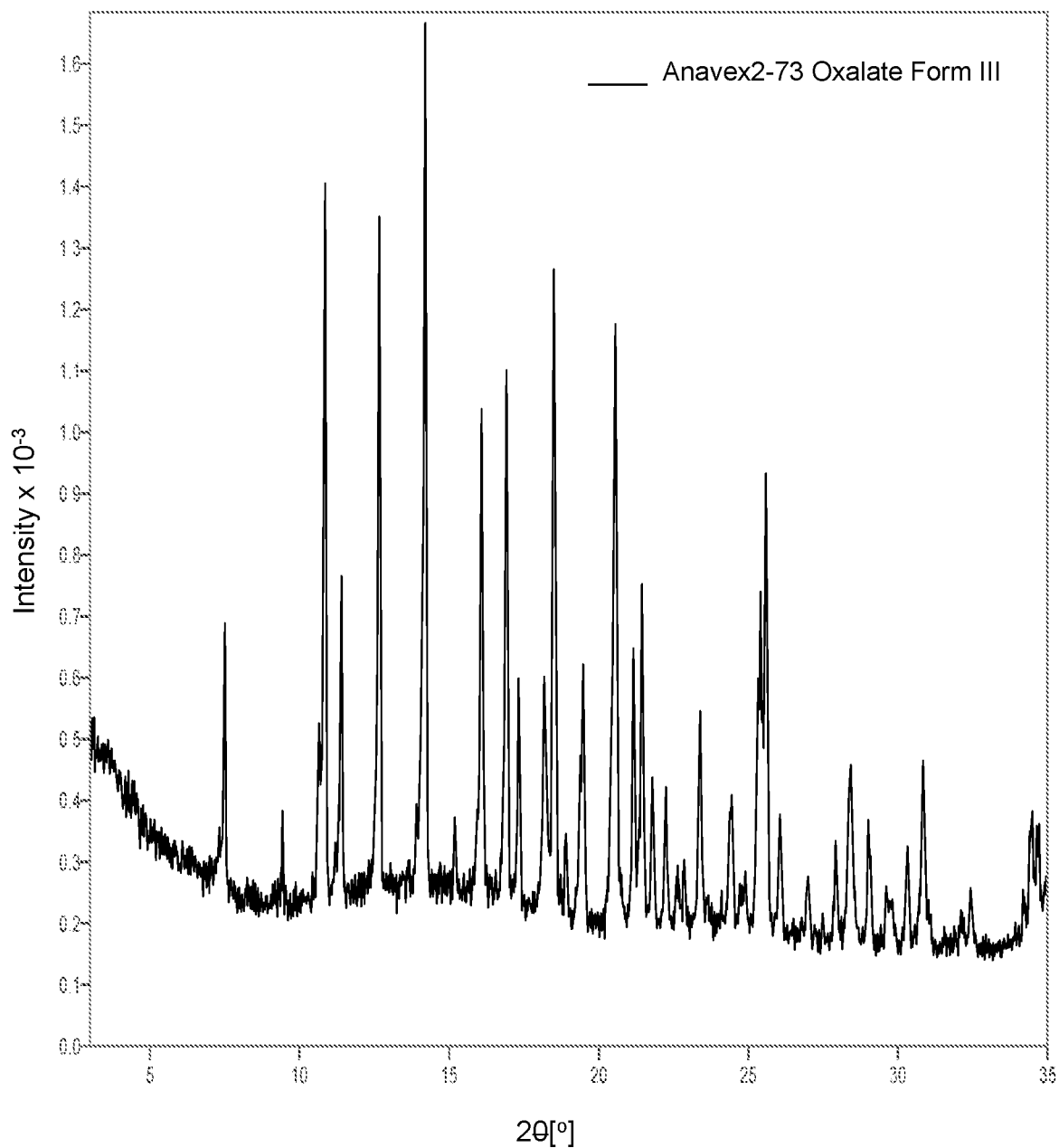
FIG. 23 Anavex2-73 Oxalate Form III XRPD Pattern.

A2-73 oxalate Form III is anhydrous, crystalline and melts with a DSC onset temperature of ca. 154° C. Its XRPD pattern, obtained using copper Kα radiation is provided in FIG. 23.

The twenty most intense XRPD peaks for Anavex2-73 oxalate Form III, measured using copper Kα radiation.

TABLE 16

| Pos. [°2θ] | d-spacing [Å] | Rel. Int. [%] |
|---|---|---|
| 7.50 | 11.786 | 30 |
| 10.66 | 8.302 | 21 |
| 10.86 | 8.150 | 82 |
| 11.41 | 7.758 | 37 |
| 12.66 | 6.991 | 79 |
| 14.20 | 6.236 | 100 |
| 16.09 | 5.509 | 57 |
| 16.91 | 5.242 | 62 |
| 17.33 | 5.118 | 28 |
| 18.17 | 4.882 | 27 |
| 18.51 | 4.794 | 73 |
| 19.48 | 4.558 | 29 |
| 20.55 | 4.322 | 68 |
| 21.17 | 4.198 | 31 |
| 21.45 | 4.143 | 38 |
| 23.38 | 3.805 | 25 |
| 25.40 | 3.507 | 35 |
| 25.59 | 3.481 | 52 |
| 28.41 | 3.142 | 19 |
| 30.84 | 2.900 | 21 | p. Dihydrogen Phosphate Form I

A2-73 dihydrogen phosphate (mono-A2-73 phosphate) Form I is crystalline, hygroscopic and melts with a DSC onset temperature of ca. 187-193° C. The isolated sample of Form I consisted of small agglomerates of highly birefringent crystals, and it exhibits solubilities of ca. 47.2 and 33.1 mg/mL at pH 1.2 and 4.5, respectively. The pH of a saturated solution of Form I in water is 2.66. Its PLM and XRPD pattern are provided in FIGS. 24 and 25 respectively.

Figure 24:
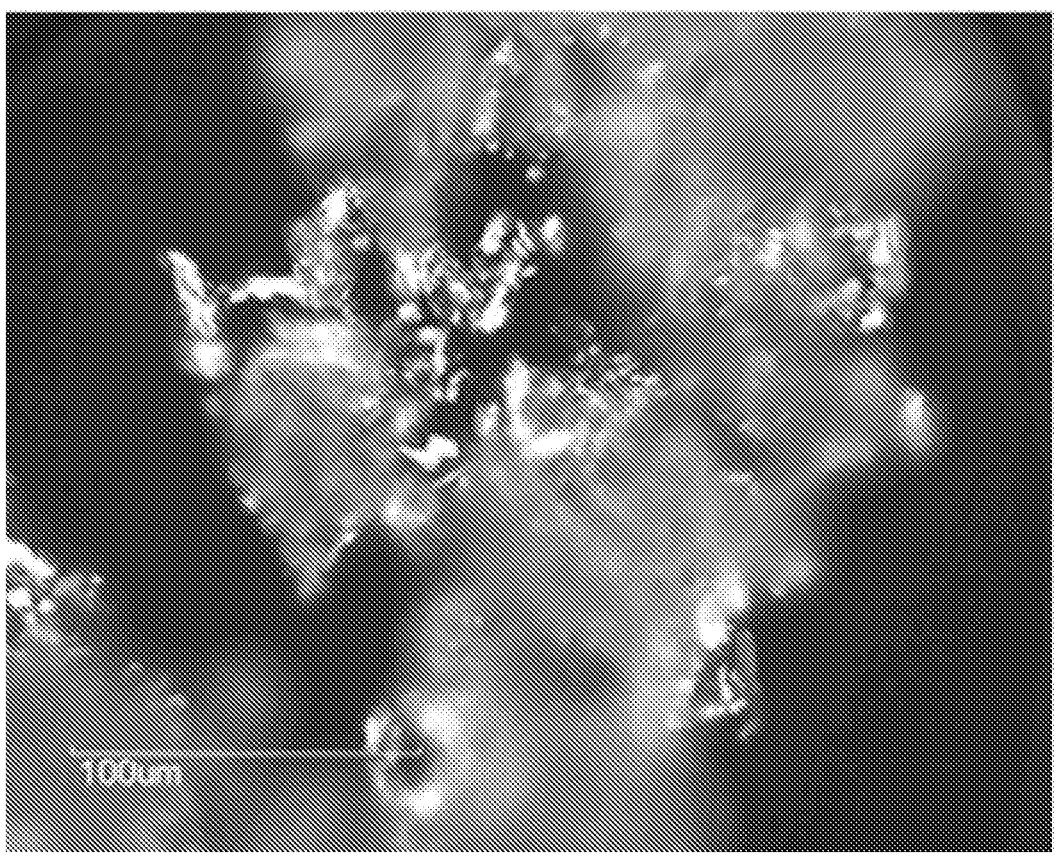
FIG. 24 Polarized-light Microscopy (PLM) of Anavex2-73 dihydrogen phosphate Form I.

FIG. 24 is a polarized-light microscopy (PLM) of Anavex2-73 dihydrogen phosphate Form I.

Figure 25:
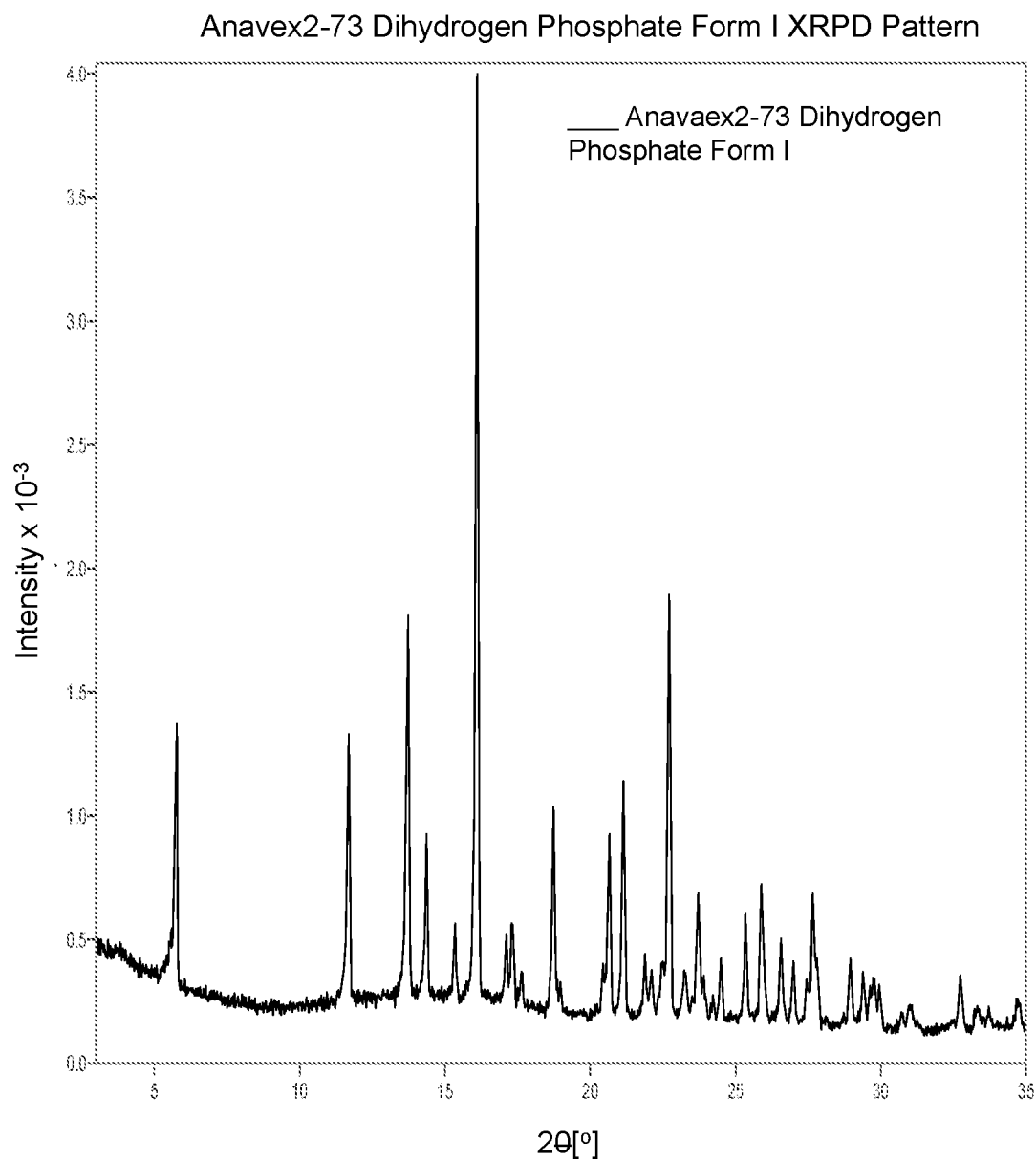
FIG. 25 XRPD pattern of Anavex2-73 dihydrogen phosphate Form I obtained using copper Kα radiation.

XRPD pattern of Anavex2-73 dihydrogen phosphate Form I obtained using copper Kα radiation is shown in FIG. 25.

The twenty most intense XRPD peaks for Anavex2-73 dihydrogen phosphate Form I, measured using copper Kα radiation.

TABLE 17

| Pos. [°2θ] | d-spacing [Å] | Rel. Int. [%] |
|---|---|---|
| 5.76 | 15.334 | 28 |
| 11.69 | 7.570 | 29 |
| 13.73 | 6.450 | 42 |
| 14.36 | 6.166 | 19 |
| 15.35 | 5.772 | 9 |
| 16.11 | 5.502 | 100 |
| 17.11 | 5.184 | 8 |
| 17.32 | 5.120 | 9 |
| 18.74 | 4.736 | 22 |
| 20.65 | 4.301 | 19 |
| 21.14 | 4.203 | 25 |
| 21.88 | 4.062 | 7 |
| 22.71 | 3.916 | 46 |
| 23.71 | 3.752 | 13 |
| 25.34 | 3.515 | 12 |
| 25.89 | 3.442 | 15 |
| 26.56 | 3.356 | 9 |
| 26.99 | 3.304 | 7 |
| 27.66 | 3.225 | 14 |
| 28.95 | 3.084 | 7 | q. Edisylate Form I

Figure 26:
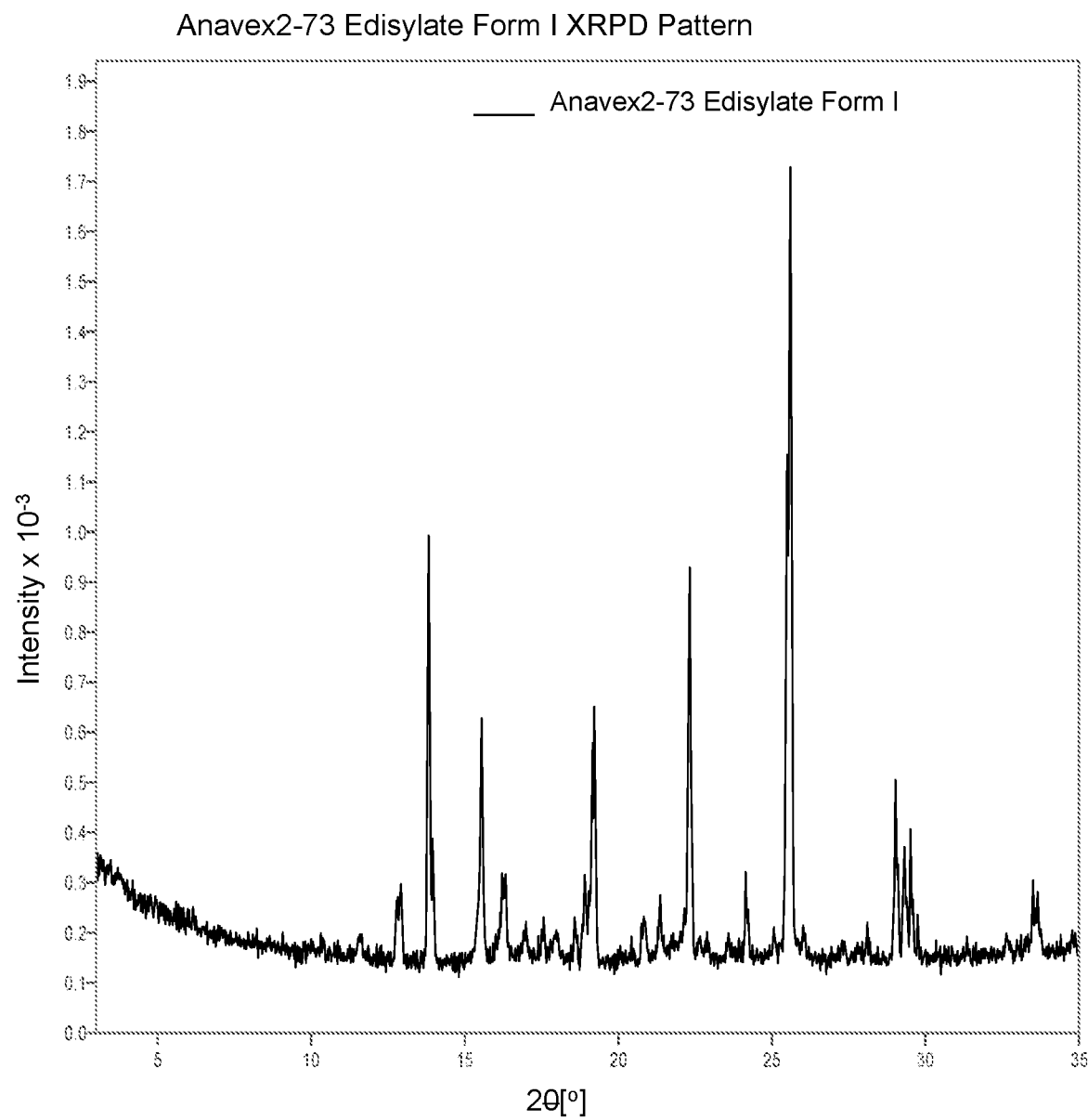
FIG. 26 A2-73 edisylate Form I XRPD pattern, obtained using copper Kα radiation.

A2-73 edisylate Form I is crystalline. Its XRPD pattern, obtained using copper Kα radiation is provided in FIG. 26.

The twenty most intense XRPD peaks for Anavex2-73 edisylate Form I, measured using copper Kα radiation.

TABLE 16

| Pos. [°2θ] | d-spacing [Å] | Rel. Int. [%] |
|---|---|---|
| 3.43 | 25.781 | 4 |
| 12.91 | 6.856 | 9 |
| 13.82 | 6.406 | 53 |
| 13.96 | 6.343 | 15 |
| 15.56 | 5.696 | 30 |
| 16.29 | 5.443 | 8 |
| 18.60 | 4.771 | 5 |
| 18.91 | 4.692 | 9 |
| 19.20 | 4.622 | 25 |
| 20.86 | 4.259 | 5 |
| 21.35 | 4.162 | 7 |
| 22.33 | 3.981 | 50 |
| 24.15 | 3.685 | 11 |
| 25.49 | 3.491 | 62 |
| 25.59 | 3.481 | 100 |
| 29.02 | 3.077 | 22 |
| 29.31 | 3.047 | 13 |
| 29.52 | 3.026 | 16 |
| 29.75 | 3.003 | 5 |
| 33.52 | 2.674 | 7 | r. Benzoate Form I

Figure 27:
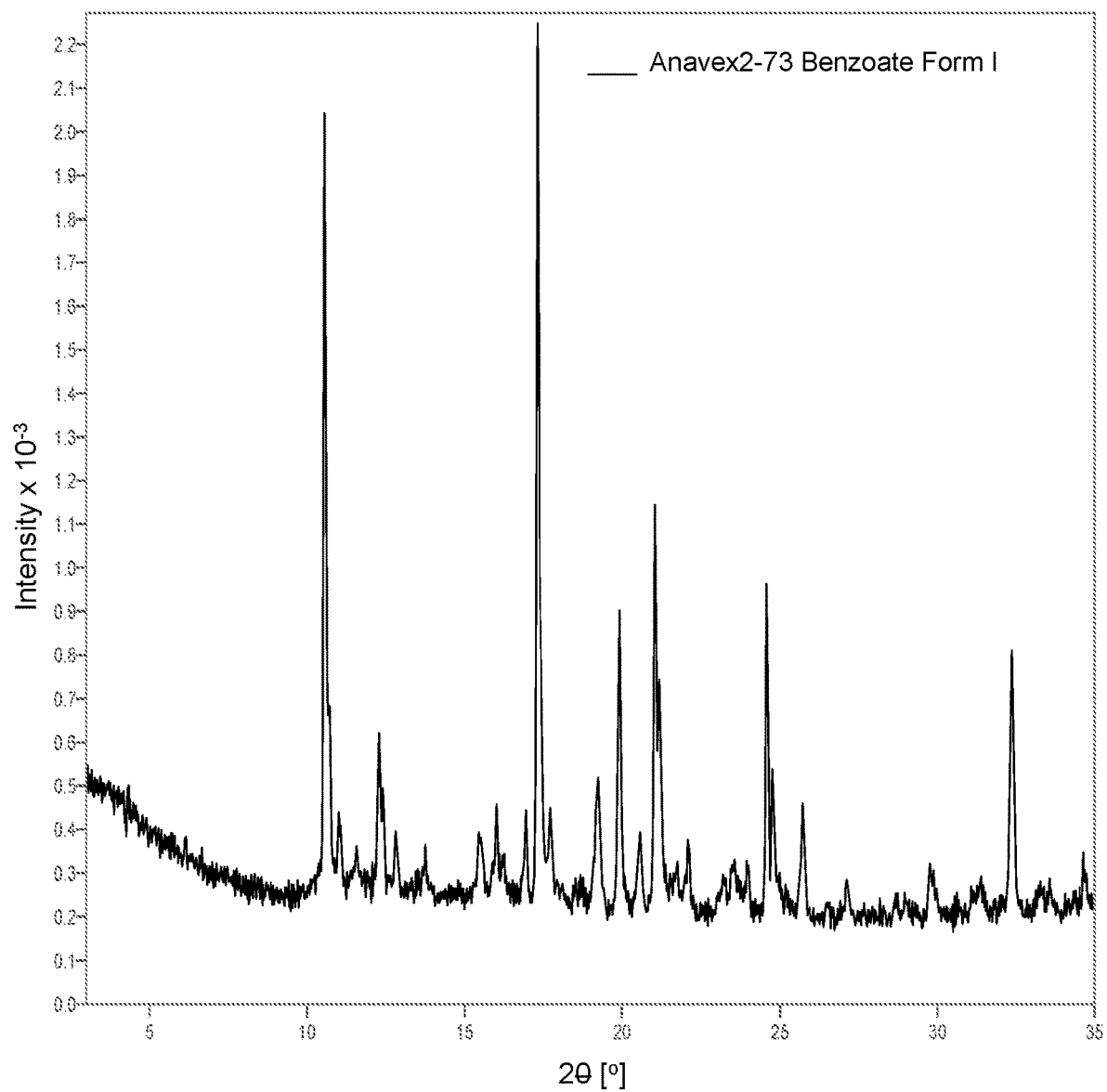
FIG. 27 A2-73 benzoate Form I XRPD pattern, obtained using copper Kα radiation.

A2-73 benzoate Form I is crystalline and melts with a DSC onset temperature of ca. 116° C. Its XRPD pattern, obtained using copper Kα radiation is provided in FIG. 27.

The twenty most intense XRPD peaks for Anavex2-73 benzoate Form I, measured using copper Kα radiation.

TABLE 17

| Pos. [°2θ] | d-spacing [Å] | Rel. Int. [%] |
|---|---|---|
| 10.57 | 8.373 | 89 |
| 10.73 | 8.246 | 22 |
| 11.04 | 8.018 | 9 |
| 12.30 | 7.195 | 19 |
| 12.82 | 6.906 | 8 |
| 15.48 | 5.725 | 8 |
| 16.02 | 5.534 | 10 |
| 16.93 | 5.237 | 11 |
| 17.31 | 5.123 | 100 |
| 17.73 | 5.003 | 11 |
| 19.24 | 4.614 | 15 |
| 19.91 | 4.459 | 34 |
| 20.56 | 4.319 | 9 |
| 21.04 | 4.223 | 47 |
| 21.18 | 4.194 | 26 |
| 22.10 | 4.023 | 8 |
| 24.57 | 3.623 | 38 |
| 24.76 | 3.596 | 17 |
| 25.73 | 3.463 | 12 |
| 32.35 | 2.767 | 30 | s. Hydrogen Fumarate Form I

A2-73 hydrogen fumarate (mono-A2-73 fumarate) Form I is anhydrous, crystalline and melts with a DSC onset temperature of ca. 193° C. Form I consisted of small agglomerates highly-birefringent crystals. Its PLM and XRPD pattern are provided in FIGS. 28 and 29 respectively.

Figure 28:
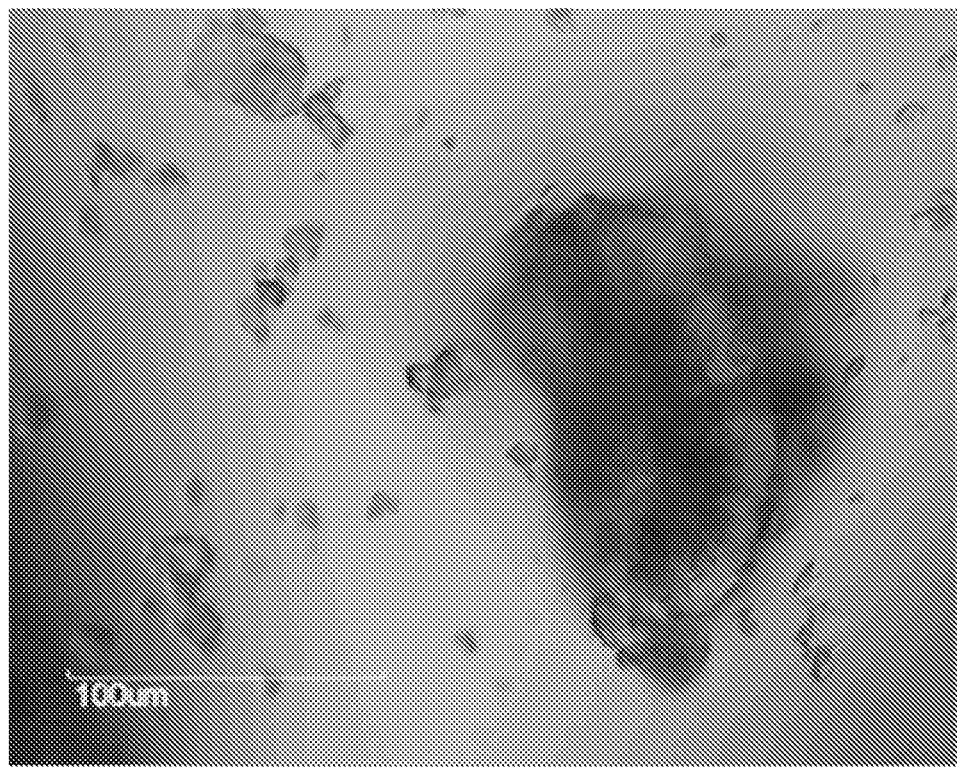
FIG. 28 Polarized-light Microscopy (PLM) of Anavex2-73 hydrogen fumarate Form I.

FIG. 28 shows a polarized-light microscopy (PLM) of Anavex2-73 hydrogen fumarate Form I.

Figure 29:
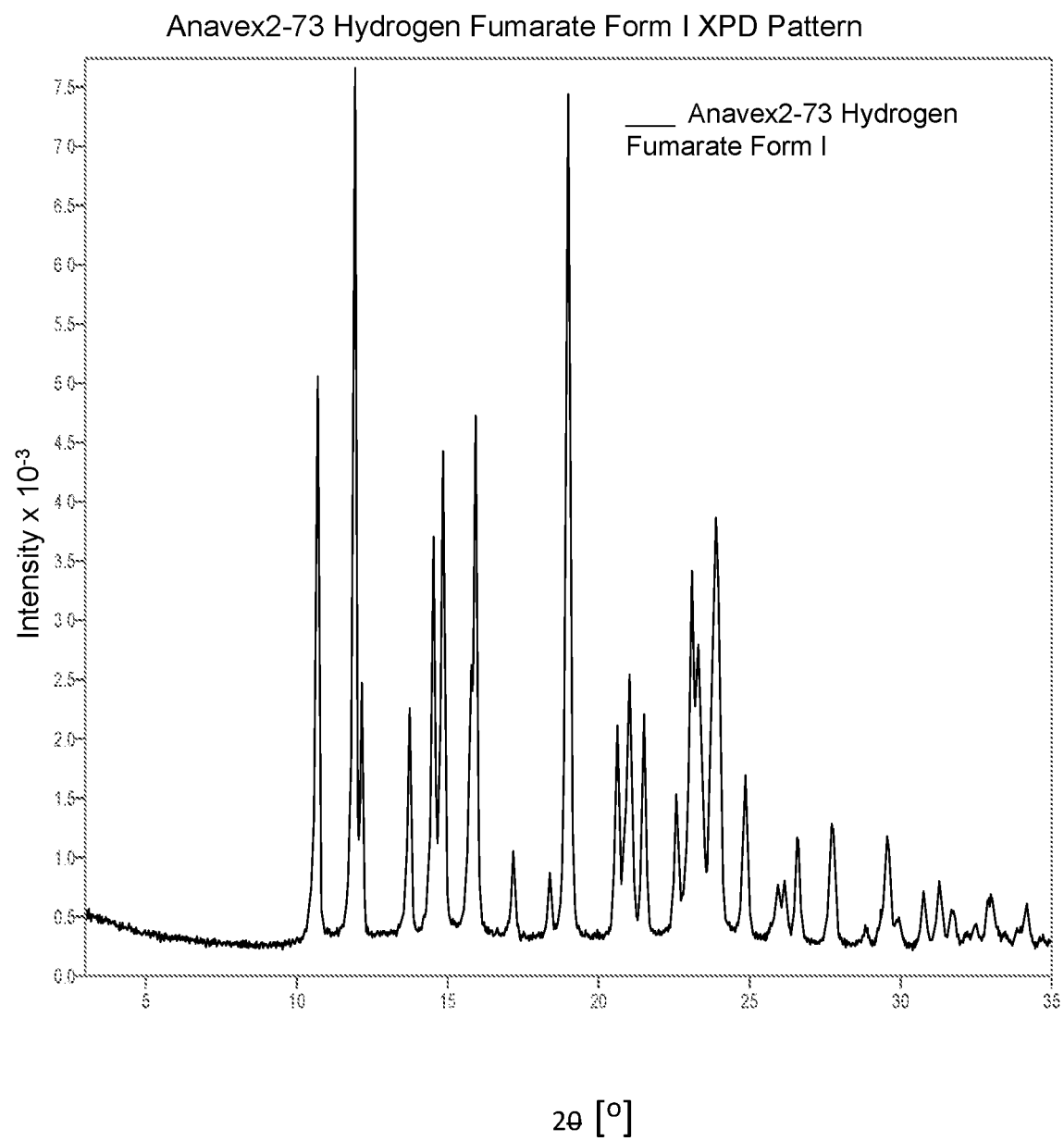
FIG. 29 A2-73 hydrogen fumarate Form I XRPD pattern, obtained using copper Kα radiation.

XRPD pattern of Anavex2-73 hydrogen fumarate Form I obtained using copper Kα radiation I shown in FIG. 29.

The twenty most intense XRPD peaks for Anavex2-73 hydrogen fumarate Form I, measured using copper Kα radiation.

TABLE

| Pos. [°2θ] | d-spacing [Å] | Rel. Int. [%] |
|---|---|---|
| 10.71 | 8.264 | 65 |
| 11.94 | 7.415 | 100 |
| 12.17 | 7.274 | 29 |
| 13.74 | 6.444 | 27 |
| 14.54 | 6.092 | 47 |
| 14.85 | 5.965 | 56 |
| 15.79 | 5.613 | 32 |
| 15.93 | 5.562 | 60 |
| 18.99 | 4.674 | 96 |
| 20.61 | 4.309 | 25 |
| 21.02 | 4.227 | 31 |
| 21.51 | 4.132 | 26 |
| 22.58 | 3.938 | 16 |
| 23.08 | 3.853 | 42 |
| 23.29 | 3.820 | 34 |
| 23.74 | 3.748 | 30 |
| 23.88 | 3.723 | 49 |
| 23.98 | 3.717 | 37 |
| 24.86 | 3.578 | 19 |
| 27.74 | 3.214 | 14 | t. Hydrogen Fumarate Form II

Figure 30:
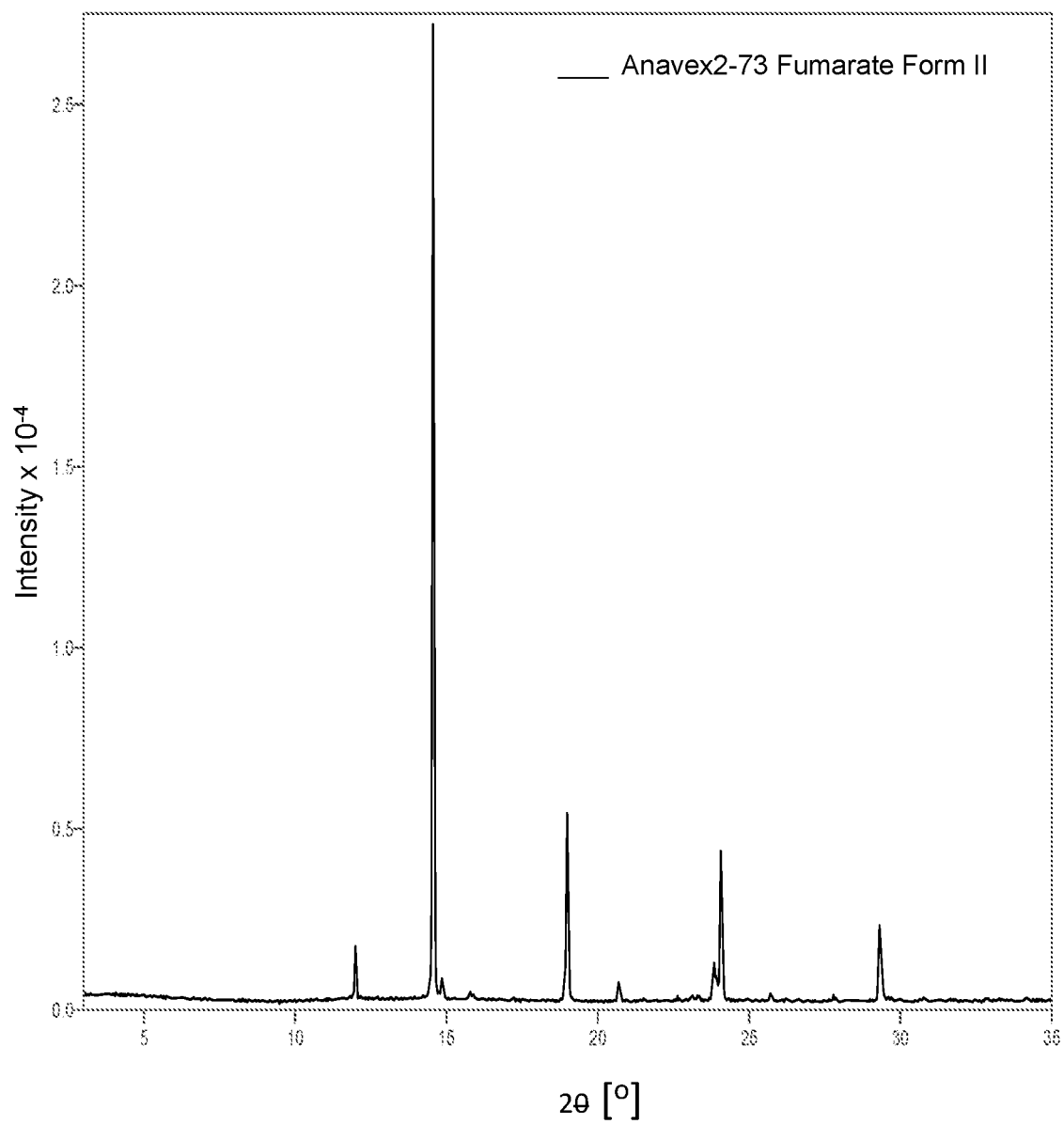
FIG. 30 A2-73 hydrogen fumarate Form II XRPD pattern, obtained using copper Kα radiation.

A2-73 fumarate Form II is crystalline and melts with a DSC onset temperature of ca. 196° C. Its XRPD pattern, obtained using copper Kα radiation is provided in FIG. 30.

The seventeen most intense XRPD peaks for Anavex2-73 fumarate Form II, measured using copper Kα radiation.

TABLE

| Pos. [°2θ] | d-spacing [Å] | Rel. Int. [%] |
|---|---|---|
| 11.99 | 7.382 | 5.4 |
| 14.56 | 6.084 | 100.0 |
| 14.86 | 5.962 | 2.2 |
| 15.78 | 5.617 | 0.8 |
| 18.99 | 4.675 | 19.0 |
| 20.69 | 4.293 | 1.9 |
| 22.63 | 3.929 | 0.3 |
| 23.33 | 3.813 | 0.4 |
| 23.85 | 3.731 | 3.9 |

TABLE-continued

| Pos. [°2θ] | d-spacing [Å] | Rel. Int. [%] |
|---|---|---|
| 24.07 | 3.695 | 15.3 |
| 24.13 | 3.694 | 7.7 |
| 25.70 | 3.464 | 0.8 |
| 27.80 | 3.206 | 0.4 |
| 29.31 | 3.045 | 7.7 |
| 29.39 | 3.045 | 4.4 |
| 30.74 | 2.906 | 0.2 |
| 32.87 | 2.723 | 0.2 | u. Hydrogen Fumarate Form III

A2-73 hydrogen fumarate (mono-A2-73 fumarate) Form III is anhydrous, crystalline, melts with a DSC onset temperature of ca. 197° C., and is slightly hygroscopic, picking up ca. 0.9% w/w at 90% RH. Form III consists of large, highly-birefringent columnar (lathe-like) crystals. Form III exhibited moderate solubility at gastric pH (generally about 1.5 to 3.5) and lower solubility at GI pH. GI pH shall mean about pH 6 in the duodenum, increasing gradually to about pH 7.4 in the terminal ileum before dropping to about pH 5.7 in the caecum and gradually increasing to about pH 6.7 in the rectum. Measured solubilities of ca. 43.0, 4.1 and 12.6 mg/mL at pH 1.2, 4.5 and 6.8, respectively, were observed for Form III. The pH of a saturated solution of Form III is 3.61. Its PLM and XRPD pattern are provided in FIGS. 31 and 32.

Figure 31:
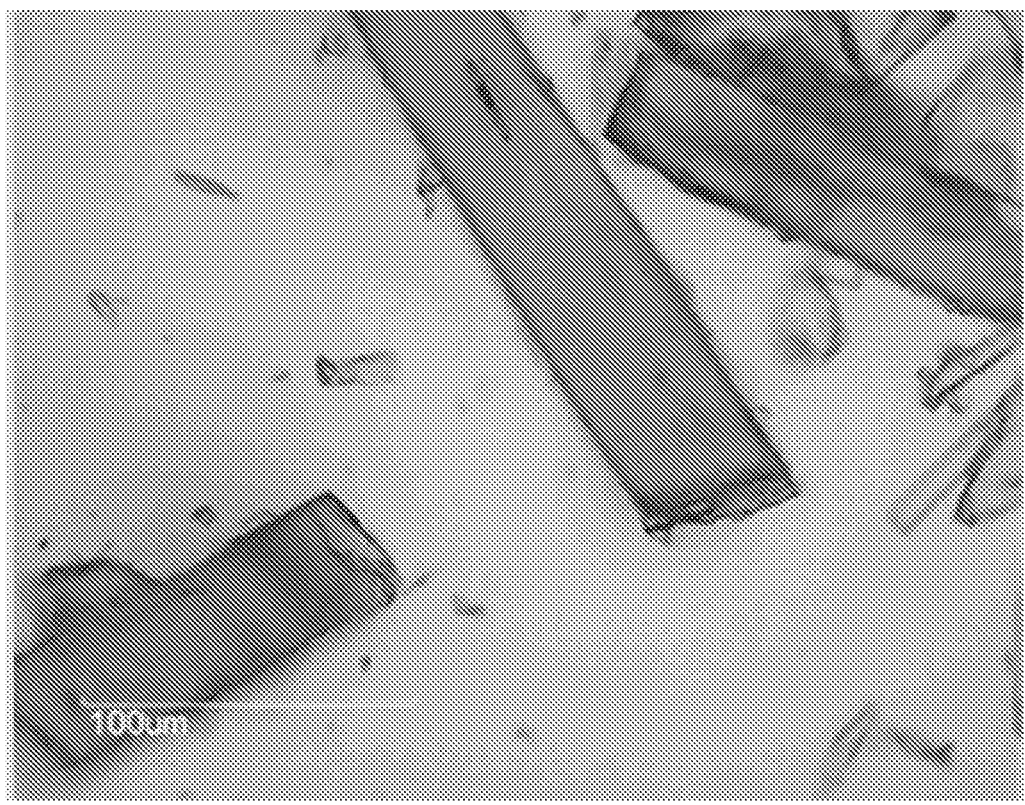
FIG. 31 Polarized-light Microscopy (PLM) of Anavex2-73 hydrogen fumarate Form III.

FIG. 31 shows a polarized-light microscopy (PLM) of Anavex2-73 hydrogen fumarate Form III.

Figure 32:
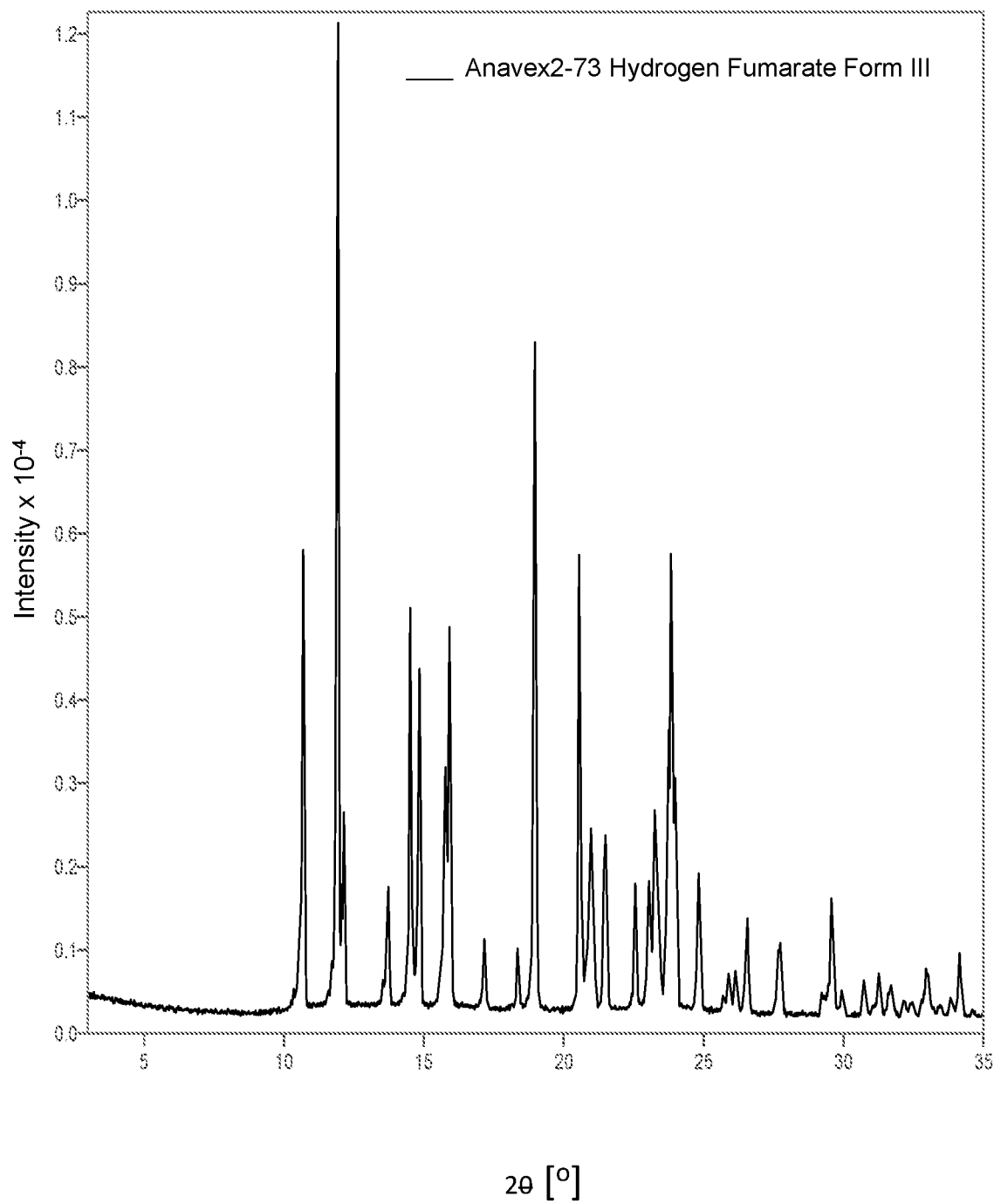
FIG. 32 XRPD pattern of Anavex2-73 hydrogen fumarate Form III obtained using copper Kα radiation.

XRPD pattern of Anavex2-73 hydrogen fumarate Form III obtained using copper Kα radiation is shown in FIG. 32.

The twenty most intense XRPD peaks for Anavex2-73 Fumarate Form III, measured using copper Kα radiation.

TABLE

| Pos. [°2θ] | d-spacing [Å] | Rel. Int. [%] |
|---|---|---|
| 10.69 | 8.273 | 47 |
| 11.93 | 7.417 | 100 |
| 12.05 | 7.342 | 13 |
| 12.14 | 7.288 | 20 |
| 14.51 | 6.104 | 40 |
| 14.85 | 5.967 | 34 |
| 15.78 | 5.617 | 25 |
| 15.92 | 5.566 | 38 |
| 18.97 | 4.677 | 67 |
| 20.55 | 4.322 | 46 |
| 20.98 | 4.235 | 18 |
| 21.42 | 4.145 | 13 |
| 21.49 | 4.135 | 18 |
| 22.56 | 3.942 | 13 |
| 23.05 | 3.859 | 13 |
| 23.25 | 3.826 | 20 |
| 23.69 | 3.755 | 23 |
| 23.83 | 3.734 | 46 |
| 23.98 | 3.711 | 23 |
| 24.82 | 3.584 | 14 | v. Fumarate Form IV

Figure 33:
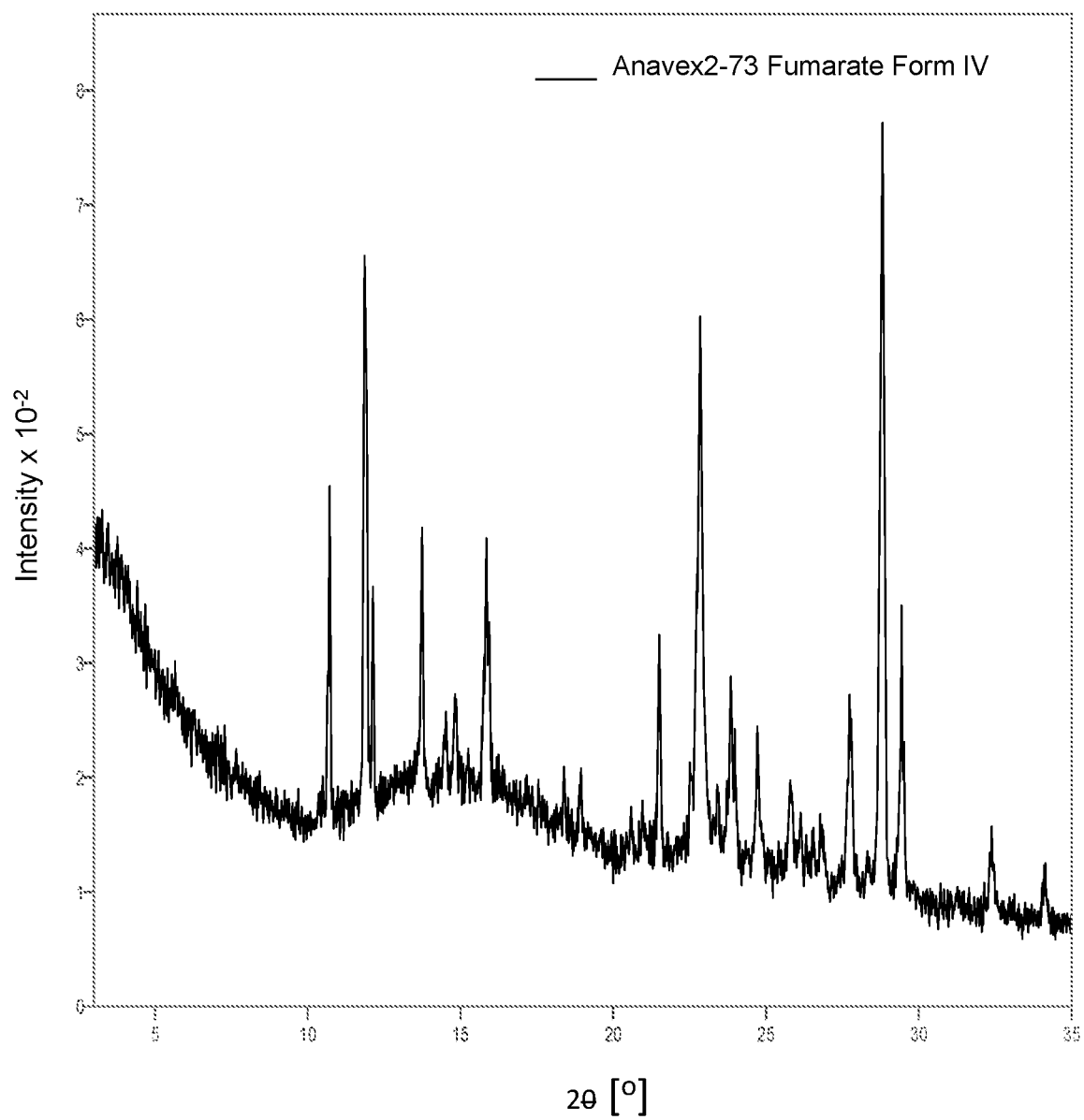
FIG. 33 XRPD pattern of Anavex2-73 hydrogen fumarate Form IV obtained using copper Kα radiation.

A2-73 fumarate Form IV is anhydrous, crystalline and melts with a DSC onset temperature of ca. 170° C., followed by sublimation. Its XRPD pattern, obtained using copper Kα radiation is provided in FIG. 33.

The twenty most intense XRPD peaks for Anavex2-73 Form fumarate IV, measured using copper Kα radiation.

TABLE

| Pos. [°2θ] | d-spacing [Å] | Rel. Int. [%] |
|---|---|---|
| 10.72 | 8.257 | 43 |
| 11.87 | 7.456 | 73 |
| 12.13 | 7.296 | 30 |
| 13.74 | 6.444 | 37 |
| 14.52 | 6.102 | 13 |
| 14.83 | 5.975 | 15 |
| 15.84 | 5.594 | 32 |
| 18.37 | 4.829 | 6 |
| 21.50 | 4.133 | 30 |
| 22.84 | 3.893 | 71 |
| 23.43 | 3.797 | 10 |
| 23.85 | 3.732 | 25 |
| 24.73 | 3.600 | 17 |
| 25.81 | 3.451 | 12 |
| 26.82 | 3.324 | 7 |
| 27.75 | 3.215 | 22 |
| 28.81 | 3.099 | 100 |
| 29.44 | 3.034 | 38 |
| 32.37 | 2.766 | 8 |
| 34.11 | 2.628 | 6 | w. Fumarate Form V

Figure 34:
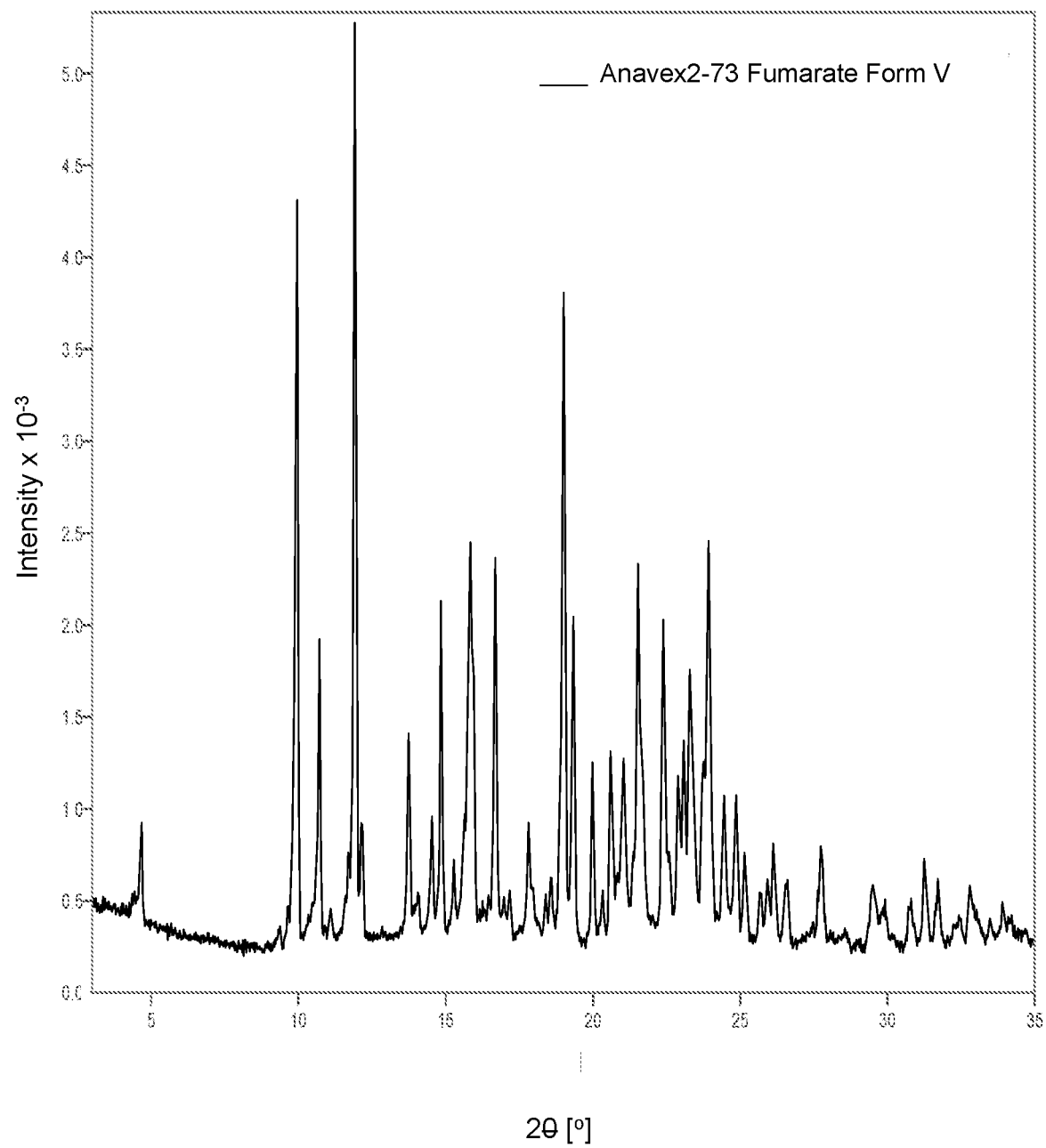
FIG. 34 XRPD pattern of Anavex2-73 hydrogen fumarate Form V obtained using copper Kα radiation.

A2-73 fumarate (di-A2-73 fumarate) Form V is crystalline. Its XRPD pattern, obtained using copper Kα radiation is provided in FIG. 34.

The twenty most intense XRPD peaks for Anavex2-73 Form fumarate V, measured using copper Kα radiation.

TABLE

| Pos. [°2θ] | d-spacing [Å] | Rel. Int. [%] |
|---|---|---|
| 9.96 | 8.884 | 81 |
| 10.71 | 8.257 | 33 |
| 11.92 | 7.425 | 100 |
| 13.74 | 6.445 | 23 |
| 14.85 | 5.967 | 37 |
| 15.83 | 5.597 | 44 |
| 15.96 | 5.555 | 29 |
| 16.69 | 5.313 | 42 |
| 19.01 | 4.668 | 71 |
| 19.33 | 4.591 | 36 |
| 19.99 | 4.442 | 20 |
| 20.60 | 4.311 | 21 |
| 21.03 | 4.225 | 20 |
| 21.52 | 4.129 | 40 |
| 21.68 | 4.099 | 19 |
| 22.40 | 3.970 | 35 |
| 22.89 | 3.886 | 18 |
| 23.07 | 3.855 | 22 |
| 23.29 | 3.820 | 30 |
| 23.92 | 3.720 | 44 |

II. Pharmaceutical Formulations

One aspect of the disclosure encompasses a pharmaceutical formulation for delivery of A2-73. A pharmaceutical formulation comprises a therapeutically effective amount of a crystalline form of A2-73 selected from A2-73 freebase and any pharmaceutically acceptable A2-73 salt as disclosed herein.

A pharmaceutical formulation can be prepared as known in the art for extended or slow release, or for substantially immediate release, and can comprise from about 1 mg to about 50 g of crystalline A2-73. For instance, formulations for immediate delivery can comprise crystalline A2-73 salt such as the hydrochloride salt. In other aspects, the formulations can be prepared for extended release of crystalline A2-73. In non-limiting example, a formulation for extended release of crystalline A2-73 can comprise crystalline A2-73 freebase.

A pharmaceutical formulation further comprises one or more pharmaceutically acceptable excipients. Non-limiting examples of excipients include chemical enhancers, humectants, pressure sensitive adhesives, antioxidants, solubilizers, thickening agents, plasticizers, adjuvants, carriers, excipients, vehicles, coatings, and any combinations thereof. One or more excipients can be selected for oral, transdermal, parenteral, intraperitoneal, intravascular, subcutaneous, by inhalation spray, rectal, or intrapulmonary administration.

Crystalline A2-73 can in general be formulated for improving patient compliance, preventing a subject from removing the drug-delivery device. For instance, formulations could be formulated for improved patient compliance and preventing removal of a drug-delivery device by providing formulations for extended delivery. Extended delivery can range for periods ranging from more than one day, to months. This may be especially relevant for patients with compromised cognitive and/or motor-control abilities. Extended delivery for periods can range from about 1 day to about 1 year, from about 1 day to about 1 week, from about 3 days to about 1 month, from about 2 weeks to about 6 months, or from about 2 months to about 4 months.

Extended release formulations could be used for substantially continuous delivery of drug at a preselected rate. For example, for crystalline A2-73, the drug can be delivered at a rate of from about 1 mg to about 100 mg/day, from about 40 to about 60 gm/day, or from about 10 to about 30 gm/day. Appropriate amounts of crystalline A2-73 can be readily determined by the ordinarily skilled artisan based upon, for example, the intended duration of administration of the drug by the extended release formulation, the delivery mechanism, the particular formulation, and the relative potency of the drug among other factors.

i. Binders

Non-limiting examples of binders suitable for the formulations of various aspects include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

The binder can be introduced into the mixture to be granulated in a solid form including but not limited to a crystal, a particle, a powder, or any other finely divided solid form known in the art. Alternatively, the binder can be dissolved or suspended in a solvent and sprayed onto the mixture in a granulation device as a binder fluid during granulation.

ii. Diluent

Non-limiting examples of diluents (also referred to as "fillers" or "thinners") include carbohydrates, inorganic compounds, and biocompatible polymers, such as polyvinylpyrrolidone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing.

iii. Disintegrents

Disintegrents can be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

iv. Preservatives

Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

v. Flavor-Modifying Agents

Suitable flavor-modifying agents include flavorants, taste-masking agents, sweeteners, and the like. Flavorants include, but are not limited to, synthetic flavor oils and flavoring aromatics and/or natural oils, extracts from plants, leaves, flowers, fruits, and combinations thereof. Other non-limiting examples of flavors include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

Taste-masking agents include but are not limited to cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®, Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol copolymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other aspects, additional taste-masking agents contemplated are those described in U.S. Pat. Nos. 4,851,226, 5,075,114, and 5,876,759, each of which is hereby incorporated by reference in its entirety.

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

vi. Lubricants and Glidants

The lubricant compositions may be utilized to lubricate ingredients that form a pharmaceutical composition. As a glidant, the lubricant facilitates removal of solid dosage forms during the manufacturing process. Non-limiting examples of lubricants and glidants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil. The pharmaceutical composition will generally comprise from about 0.01% to about 10% by weight of a lubricant. In some aspects, the pharmaceutical composition will comprise from about 0.1% to about 5% by weight of a lubricant. In a further aspect, the pharmaceutical composition will comprise from about 0.5% to about 2% by weight of a lubricant.

vii. Dispersants

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

viii. Colorants

Depending upon the aspect of the disclosure, it may be desirable to include a coloring agent. Suitable color additives include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various aspects of the disclosure.

ix. pH Modifiers

Non-limiting examples of pH modifiers include citric acid, acetic acid, tartaric acid, malic acid, fumaric acid, lactic acid, phosphoric acid, sorbic acid, benzoic acid, sodium carbonate and sodium bicarbonate.

(x) Chelating Agents

A chelating agent may be included as an excipient to immobilize oxidative groups, including but not limited to metal ions, in order to inhibit the oxidative degradation of the morphinan by these oxidative groups. Non-limiting examples of chelating agents include lysine, methionine, glycine, gluconate, polysaccharides, glutamate, aspartate, and disodium ethylenediaminetetraacetate ($Na_2EDTA$).

(xi) Antimicrobial Agents

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, $Na_2EDTA$, and sulfites including but not limited to sulfur dioxide, sodium bisulfite, and potassium hydrogen sulfite.

(xii) Release-Controlling Polymers

Release-controlling polymers may be included in the various aspects of the solid dosage pharmaceutical compositions incorporating compounds according to this disclosure. In one aspect, the release-controlling polymers may be used as a tablet coating. In other aspects, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

Suitable hydrophilic release-controlling polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, crosslinked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabic gum, carrageens gum, ghafti gum, guar gum, karaya gum, locust bean gum, okra gum, tragacanth gum, scleroglucan gum, xanthan gum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylamides, polyacrylic acid, polyamides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and combinations thereof.

(xiii) Coatings

A solid dosage comprising a compound according to this disclosure may comprise a coating, wherein such a coating may control release of the compound, act as a moisture barrier, or buffer or modify pH. A "control releasing coat" or "controlled release coat" as used herein is defined to mean a functional coat which can for example comprise at least one pH independent polymer, pH dependent polymer (for example enteric or reverse enteric type polymers), soluble polymer, insoluble polymer, lipids, lipidic materials, or combinations thereof. The coating, when applied onto a dosage form, may slow (for example when applied to a normal release matrix dosage form), further slow (for example when applied to a controlled release matrix dosage form) or modify the rate of release of a compound according to this disclosure when applied to an uncoated dosage form. For example, the control releasing coat can be designed such that when the control releasing coat is applied to a dosage form, the dosage form in conjunction with the control releasing coat can exhibit the release of the compound according to this disclosure, such as a "modified-release", "controlled-release", "sustained-release", "extended-release", "delayed-release", "prolonged-release" or combinations thereof. The "control releasing coat" may optionally comprise additional materials that may alter the functionality of the control releasing coat.

The term "moisture barrier" as used herein is one, which impedes or retards the absorption of moisture. Compounds according to this disclosure may be hygroscopic and, as such, may be susceptible to decomposition over time under highly humid conditions. The proportion of the components of the moisture barrier and the amount of the moisture barrier optionally applied onto the control-releasing coating or onto the core is typically such that the moisture barrier does not fall within the USP definition and requirement for an enteric coat. Suitably, the moisture barrier may comprise an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier may additionally comprise other conventional inert excipients, which may improve processing of an extended-release formulation.

Coating and matrix materials which may be used in accordance with the invention are those known in the art for use in controlled-release formulations, such as synthetic polymers of the polyvinyl type, e.g. polyvinylchloride, polyvinylacetate and copolymers thereof, polyvinylalcohol, and polyvinylpyrrolidone; synthetic polymers of the polyethylene type, e.g. polyethylene and polystyrene; acrylic acid polymers; biopolymers or modified biopolymers, such as cellulosic polymers, shellac and gelatin; fats, oils, higher fatty acids and higher alcohols (i.e., acids and alcohols containing alkyl chains of at least 10 carbon atoms), for example aluminum monostearate, cetylalcohol, hydrogenated beef tallow, hydrogenated castor oil, 12-hydroxystearyl alcohol, glyceryl mono- or dipalmitate; glyceryl mono-, di- or tristearate; myristyl alcohol, stearic acid, stearyl alcohol, and polyethyleneglycols; waxes; sugars and sugar alcohols.

The pH-buffering properties of a coating may be strengthened by introducing into the coating substances chosen from a group of compounds usually used in antacid formulations, for example magnesium oxide, hydroxide or carbonate, aluminum or calcium hydroxide, carbonate or silicate; composite aluminum/magnesium compounds, for example $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2SiO_2 \cdot nH_2O$, aluminum bicarbonate coprecipitate or similar compounds; or other pharmaceutically acceptable pH-buffering compounds, for example the sodium, potassium, calcium, magnesium and aluminum salts of phosphoric, carbonic, citric or other suitable, weak, inorganic or organic acids; or suitable organic bases, including basic amino acids; and salts or combinations thereof.

A pH-dependent coating serves to release the drug in desired areas of the gastrointestinal (GI) tract, e.g., the stomach or small intestine. When a pH-independent coating is desired, the coating is designed to achieve optimal release regardless of pH-changes in the environmental fluid, e.g., the GI tract. When the coating is formulated to release a compound according to this disclosure in the intestines (especially the upper small intestines), the coating is often called an "enteric coating". A pH-dependent coating may include, but is not limited to, acrylic acid polymers and copolymers, for example polymers formed from acrylic acid, methacrylic acid, methyl acrylate, ammonio methylacrylate, ethyl acrylate, methyl methacrylate and/or ethyl methacrylate (e.g., Eudragit™); cellulosic polymers such as hydroxypropyl cellulose, hydroxyethyl cellulose, hydroxypropyl methyl cellulose, methyl cellulose, ethyl cellulose, cellulose acetate, cellulose acetate phthalate (CAP), cellulose acetate trimellitate, hydroxypropylmethyl cellulose phthalate, hydroxypropylmethyl cellulose succinate and carboxymethylcellulose sodium; shellac (purified lac); vinyl polymers and copolymers such as polyvinyl pyrrolidone, polyvinyl acetate, polyvinylacetate phthalate (PVAP), vinylacetate crotonic acid copolymer, and ethylene-vinyl acetate copolymers; zein; and salts and combinations thereof.

A. Transdermal Administration

One aspect of the disclosure encompasses formulations of A2-73 for transdermal administration. Non-limiting examples of transdermal formulations include those used in a transdermal patch, such as but not limited to gels, ointments, emulsions, microemulsions, aqueous gels, foams, sprays, lotions or creams.

In one aspect, a transdermal formulation of crystalline forms of A2-73 is a transdermal patch. A transdermal patch comprises a therapeutically effective amount of a crystalline form of A2-73. The crystalline form of A2-73 can be A2-73 freebase or A2-73 salt.

The crystalline form of A2-73 in the patch can be A2-73 freebase. When the crystalline form of A2-73 is A2-73 freebase, the patch could contain from about 40 mg to about 60 mg, from about 80 mg to about 120 mg, or about 180 mg to about 220 mg of A2-73 freebase. Alternatively, the crystalline form of A2-73 in the patch can be A2-73 fumarate salt. When the Crystalline form of A2-73 is A2-73 fumarate salt, the patch could comprise from about 1 mg to about 55 mg of A2-73 fumarate salt.

Transdermal patches include those formulated for extended or slow release, and those formulated for substantially immediate release. For example, an extended release transdermal patch may include a crystalline form of A2-73 as a free base or as a A2-73 fumarate salt as disclosed herein. For example, an immediate release patch form may include for example an A2-73 salt, such as the HCl salt.

The transdermal patch can provide for extended release of A2-73 over a period ranging from about 1 day to about 7 days. Additionally, the transdermal patch can have a transcutaneous maximum flux of A2-73 ranging from about 250-350 $\mu g/cm^2/h$.

The transdermal patch can be a matrix patch or a reservoir patch. In one aspect, the patch is a matrix patch. Transdermal patches containing amounts of a compound for delivery in a matrix or a reservoir, for extended delivery of the compound are known in the art and can be as described for example in U.S. Pat. No. 9,656,441 and U.S. Patent Publication No. 2019/0099383, the disclosures of which are incorporated herein in their entirety.

A matrix patch can be covered by a peripheral pressure sensitive adhesive that extends beyond the patch in all directions. The patch can further contain one or more other excipients such as those described in Section III herein and can be selected from chemical enhancers, humectants, pressure sensitive adhesives, antioxidants, solubilizers, thickening agents, plasticizers, and any combinations thereof.

A matrix layer of a transdermal patch can be formulated for extended release. For instance, in addition to comprising a therapeutically effective amount of the active ingredient, a matrix formulation can further comprise one or more pharmaceutically acceptable carriers or excipients. Non-limiting examples of pharmaceutically acceptable carriers or excipients include chemical penetration enhancers (CPE), chemical enhancers, humectants, pressure sensitive adhesives, antioxidants, solubilizers, thickening agents, plasticizers, and any combinations thereof.

In some aspects, a matrix layer comprises one or more CPE's. Non-limiting examples of a CPE include anionic surfactants, cationic surfactants, zwitterionic surfactants, nonionic surfactants, fatty acids, fatty esters, azone and azone-like compounds, ethanol, glycerolmonolaurate, DMF, polyethylenglycole monolaurate, DMSO, ethyl alcohol, oleic acid, oleyl alcohol, glycerol monooleate, levulinic acid, dipropylene glycol, diethylene glycol monoethyl ether, lauric lactate, and combinations thereof.

In some aspects a transdermal patch of the disclosure comprises a matrix layer having a top side and a bottom side, the matrix comprising a therapeutically effective amount of a crystalline form of A2-73 selected from A2-73 freebase and A2-73 salt. The patch also comprises an adhesive layer having a top side and a bottom side, wherein the bottom side of the adhesive layer contacts the top side of the matrix layer, and wherein the adhesive layer having a first portion covering the top side of the matrix layer and a second portion extending on the sides of the matrix layer. The bottom side of the matrix contacts the skin of a user.

The transdermal patch can further have a protective layer covering the bottom side of the matrix and the bottom side of the second portion of the adhesive layer. Further, the transdermal patch can include a cover layer on the top side of the matrix. Preferably, the cover layer is at least partially bi-elastic. For instance, the bi-elastic cover layer can an acrylic copolymer having hydroxyl functional groups. In some instances, the transdermal patch can contain separating layer situated between the top side of the matrix layer and the bottom side of the adhesive layer.

A surface area of the matrix in contact with the skin of a subject can range from about 1 cm$^2$ to about 20 cm$^2$, from about 3 cm$^2$ to about 5 cm$^2$, or from about 8 cm$^2$ to about 10 cm$^2$.

In one aspect, a patch comprises a matrix comprising either A2-73 freebase or A2-73 fumarate, or a reservoir containing A2-73 freebase or A2-73 fumarate. Other excipients/chemicals/reagents which may be included in a patch matrix or reservoir are ethyl oleate (EO) and Tween 60, Tween 40, Tween 80, triethanolamine and ethanol, propylene glycol (PG) and polyvinyl alcohol (PVA), polyethylene glycol 400 (PEG 400), and methanol or any combination thereof. Patch components may include backing membrane (3M-9720), rate-controlling membrane (3M-CoTran 9728 (2 mil) and 9716 (4 mil)), and release liner (SCOTCHPAK 9755), acrylate adhesive Duro-Tak 387/2510.

B. Oral Formulation

Some aspects of the disclosure encompass an oral formulation for delivery of crystalline forms of A2-73 freebase and salt. Oral formulations are known in the art and include without limitation, a tablet, including a suspension tablet, a chewable tablet, an effervescent tablet or caplet; a pill; a powder such as a sterile packaged powder, a dispensable powder, and an effervescent powder; a capsule including both soft or hard gelatin capsules such as HPMC capsules; a lozenge; a sachet; a sprinkle; a reconstitutable powder or shake; a troche; pellets; granules; liquids; suspensions; emulsions; or semisolids and gels. Alternatively, the pharmaceutical compositions may be incorporated into a food product or powder for mixing with a liquid, or administered orally after only mixing with a non-foodstuff liquid.

Oral dosage forms include those formulated for extended or slow release, and those formulated for substantially immediate release. For example, an extended release oral dosage form may include a crystalline form of A2-73 as a free base or as a A2-73 fumarate salt as disclosed herein. For example, an immediate release oral dosage form may include for example an A2-73 salt, such as the HCl salt. Release characteristics and release time can be measured according to methods known in the art.

In one aspect, an oral dosage form comprising crystalline A2-73 provides for extended release of the A2-73 over a period ranging from about 1 day to about 3 days, 4-24 hours, e.g., 6-24 hours, preferably 12-24 hours, and can provide for delivery of about 15 to about 30 mg/day of A2-73 to a subject.

In another aspect, an oral dosage form comprising crystalline A2-73 provides for substantially immediate release of the A2-73 as understood in the art, and may for example comprise A2-73 hydrochloride in an immediate-release oral dosage form.

In one aspect, the oral formulation is an enteric coated oral dosage form comprising a core matrix ("core") comprising a therapeutically effective amount of a crystalline form of A2-73. The crystalline A2-73 can be A2-73 freebase or A2-73 salt. The core is surrounded by a coating. Preferably, the coating is an enteric coating A solid core of the instant disclosure, such as a capsule or tablet formulations contain the crystalline A2-73, along with an excipient. Non-limiting examples of excipients can be as described in Section III above and can include binders, diluents (fillers), disintegrants, effervescent disintegration agents, preservatives (antioxidants), flavor-modifying agents, lubricants and glidants, dispersants, coloring agents, pH modifiers, chelating agents, antimicrobial agents, release-controlling polymers, and combinations of any of these agents.

Non-limiting examples of binders suitable for oral formulations include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

Non-limiting examples of diluents (also referred to as "fillers" or "thinners") include carbohydrates, inorganic compounds, and biocompatible polymers, such as polyvinylpyrrolidone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing.

Disintegrents may be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

Non-limiting examples of pH modifiers include citric acid, acetic acid, tartaric acid, malic acid, fumaric acid, lactic acid, phosphoric acid, sorbic acid, benzoic acid, sodium carbonate and sodium bicarbonate.

Release-controlling polymers may be included in the oral formulations incorporating compounds according to this disclosure. In one aspect, the release-controlling polymers can be used as a tablet coating. In other aspects, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

A coating may control release of the compound, act as a moisture barrier, or buffer or modify pH. A "control releasing coat" or "controlled release coat" as used herein is defined to mean a functional coat which can for example comprise at least one pH independent polymer, pH dependent polymer (for example enteric or reverse enteric type polymers), soluble polymer, insoluble polymer, lipids, lipidic materials, or combinations thereof. The coating, when applied onto a solid dosage form, may slow (for example when applied to a normal release matrix dosage form), further slow (for example when applied to a controlled release matrix dosage form) or modify the rate of release of a compound according to this disclosure when applied to an uncoated dosage form. For example, the control releasing coat can be designed such that when the control releasing coat is applied to a dosage form, the dosage form in conjunction with the control releasing coat can exhibit the release of the compound according to this disclosure, such as an "immediate release", a "modified-release", "controlled-release", "sustained-release", "extended-release", "delayed-release", "prolonged-release" or combinations thereof. The coat may optionally comprise additional materials that may alter the functionality of the control releasing coat.

The pH-buffering properties of a coating may be strengthened by introducing into the coating substances chosen from a group of compounds usually used in antacid formulations, for example magnesium oxide, hydroxide or carbonate, aluminum or calcium hydroxide, carbonate or silicate; composite aluminum/magnesium compounds, for example $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2SiO_2 \cdot nH_2O$, aluminum bicarbonate coprecipitate or similar compounds; or other pharmaceutically acceptable pH-buffering compounds, for example the sodium, potassium, calcium, magnesium and aluminum salts of phosphoric, carbonic, citric or other suitable, weak, inorganic or organic acids; or suitable organic bases, including basic amino acids; and salts or combinations thereof.

A pH-dependent coating serves to release the drug in desired areas of the gastrointestinal (GI) tract, e.g., the stomach or small intestine. When a pH-independent coating is desired, the coating is designed to achieve optimal release regardless of pH-changes in the environmental fluid, e.g., the GI tract. When the coating is formulated to release a compound according to this disclosure in the intestines (especially the upper small intestines), the coating is often called an "enteric coating". A pH-dependent coating may include, but is not limited to, acrylic acid polymers and copolymers, for example polymers formed from acrylic acid, methacrylic acid, methyl acrylate, ammonio methylacrylate, ethyl acrylate, methyl methacrylate and/or ethyl methacrylate (e.g., Eudragit™); cellulosic polymers such as hydroxypropyl cellulose, hydroxyethyl cellulose, hydroxypropyl methyl cellulose, methyl cellulose, ethyl cellulose, cellulose acetate, cellulose acetate phthalate (CAP), cellulose acetate trimellitate, hydroxypropylmethyl cellulose phthalate, hydroxypropylmethyl cellulose succinate and carboxymethylcellulose sodium; shellac (purified lac); vinyl polymers and copolymers such as polyvinyl pyrrolidone, polyvinyl acetate, polyvinylacetate phthalate (PVAP), vinylacetate crotonic acid copolymer, and ethylene-vinyl acetate copolymers; zein; and salts and combinations thereof.

Coating and core materials which may be used in accordance with the invention are those known in the art for use in controlled-release formulations, such as synthetic polymers of the polyvinyl type, e.g. polyvinylchloride, polyvinylacetate and copolymers thereof, polyvinylalcohol, and polyvinylpyrrolidone; synthetic polymers of the polyethylene type, e.g. polyethylene and polystyrene; acrylic acid polymers; biopolymers or modified biopolymers, such as cellulosic polymers, shellac and gelatin; fats, oils, higher fatty acids and higher alcohols (i.e., acids and alcohols containing alkyl chains of at least 10 carbon atoms), for example aluminum monostearate, cetylalcohol, hydrogenated beef tallow, hydrogenated castor oil, 12-hydroxystearyl alcohol, glyceryl mono- or dipalmitate; glyceryl mono-, di- or tristearate; myristyl alcohol, stearic acid, stearyl alcohol, and polyethyleneglycols; waxes; sugars and sugar alcohols.

The crystalline A2-73 in the core can be A2-73 freebase, and the core can comprise from about 1 g to about 50 g of crystalline A2-73. The core can comprise from about 1 mg to about 50 mg A2-73 freebase. The core can also comprise from about 1 g to about 50 g, from about 10 mg to about 50 mg, from about 20 mg to about 30 mg, or from about 15 mg to about 25 mg of A2-73 fumarate salt. The core can comprise about 35% to about 40% by weight A2-73 freebase or A2-73 fumarate. In one aspect, the core comprises about 35% to about 40% by weight A2-73 freebase or A2-73 fumarate, about 55% to about 70% by weight hydroxypropyl methylcellulose acetate succinate, about 0.3% to about 0.9% by weight magnesium stearate, and about 0.05% to about 0.5% by weight colloidal silicon dioxide. The hydroxypropyl methylcellulose acetate succinate is soluble in aqueous solutions with a pH of about 5.5 and greater, a second grade of hydroxypropyl methylcellulose acetate succinate is soluble in aqueous solutions with a pH of about 6.8 and greater, and combinations thereof.

C. Subcutaneous

The formulation can be a subcutaneous injectable dosage formulation. In some aspects, the formulation can be an extended delivery subcutaneous injectable dosage formulation or for substantially immediate delivery. Extended release subcutaneous dosage formulations can comprising from comprise from about 0.1 to about 5 g of crystalline A2-73 to about 0.5 g to about 3 g of crystalline A2-73.

Injectable dosage formulations for extended release of a drug are known in the art and can include an injectable formulation formulated for extended delivery of a drug such as implantable drug delivery devices. The term "drug delivery device" as used herein refers to any implantable device suitable for delivering a formulation according to the disclosure. Non-limiting examples of devices include any implantable device with any mechanism of action including diffusive, erodible, or convective systems, e.g., osmotic pumps, biodegradable implants, electro diffusion systems, electro osmosis systems, vapor pressure pumps, electrolytic pumps, effervescent pumps, piezoelectric pumps, erosion-based systems, or electromechanical systems.

III. Dosage Forms

One aspect of the disclosure encompasses dosage forms of A2-73. A dosage form contains a therapeutically effective amount of A2-73 in a crystalline form. For instance, a dosage form can contain a neuroprotective amount of crystalline A2-73. In some aspects, the neuroprotective amount is an anti-neurodegenerative amount of A2-73 in a crystalline form as disclosed herein. The crystalline A2-73 can be crystalline A2-73 freebase or crystalline A2-73 salt. The dosage forms can be formulated as described in Section II above.

A dosage form can comprise from about 1 mg to about 50 g, from about 1 mg to about 500 mg, or about 1 mg to about 100 mg of A2-73 freebase or A2-73 salt. Further, Dosage forms can comprise from about 1 mg to about 500 mg, from about 50 to about 400 mg, or from about from about 75 to about 150 mg, or from about 150 to about 200 mg of A2-73 freebase or a A2-73 salt. For instance, the dosage form can comprise 1, 10, 20, 30, 40, 50, 60, 70, 80, 90, 100, 120, 140, 160, 180, 200, 220, 240, 260, 280, or 300 or more mg of A2-73 freebase or A2-73 salt. In some aspects, dosage forms can comprise from about 1 mg to about 500 mg, or about 1 mg to about 100 mg of A2-73 freebase or A2-73 salt.

In some aspects, the crystalline form of A2-73 in the dosage form is a freebase. When the A2-73 is a freebase, the dosage form can comprise from about 1 mg to about 500 mg, from about 40 mg to about 60 mg, from about 80 mg to about 120 mg, or about 180 mg to about 220 mg of A2-73 freebase.

In other aspects, the crystalline form of A2-73 in the dosage form is a salt of A2-73. When the A2-73 is a salt, the dosage form can comprise from about 1 mg to about 500 mg, about 1 mg to about 55 mg, from about 40 mg to about 60 mg, from about 80 mg to about 120 mg, or about 180 mg to about 220 mg of A2-73 salt.

Dosage forms include those formulated for extended or slow release, and those formulated for immediate release. For example, an immediate release dosage form may include a crystalline form of A2-73 as the free base or as a A2-73 salt as disclosed herein. For example, a fast-dissolve oral dosage form may include for example an A2-73 salt, such as the HCl salt. Alternatively, a dosage form may include a crystalline form of A2-73 as the free base or as a A2-73 salt formulated for inhalation drug delivery, either as a dry powder or aerosol spray.

Dosage forms also include those formulated for topical administration. For instance, a dosage form can be formulated as one or more of a gel, ointment, emulsion, microemulsion, solution, suspension, paste, gel, foam, spray, lotion, or cream. In one aspect, a topical administration dosage form is a transdermal patch. Transdermal patches can be for example as described in Section III below. When the dosage form is formulated as a transdermal patch, the transdermal patch can contain from about 40 mg to about 60 mg, from about 80 mg to about 120 mg, or from about 180 mg to about 220 mg of A2-73 freebase in crystalline form.

Dosage forms can alternatively be formulated for oral administration. Dosage forms formulated for oral administration can be tablets to swallow, chew, or dissolve in water or under the tongue, capsules and chewable capsules, powders, granules, teas, drops, or liquid medications or syrups. Preferably, the dosage form is an enteric coated oral formulation. Enteric coated oral formulations can be as described in Section IV below.

When the dosage form is an enteric coated oral formulation, the formulation can comprise from about 0.1 mg to about 60 mg A2-73 freebase, preferably from about 1 mg to about 50 mg A2-73 freebase.

An enteric coated oral formulation can also contain A2-73 salt in crystalline form. The A2-73 salt can be a fumarate salt, a sulfate salt, a mesylate salt, a dihydrogen phosphate salt, an edisylate salt, a benzoate salt, a hydrochloride salt, and an oxalate salt. In one aspect, the A2-73 salt is a fumarate salt. When the A2-73 salt is a fumarate salt, the enteric coated oral formulation can comprise from about 0.1 to about 100 mg of A2-73 fumarate salt, preferably from about 1 mg to about 55 mg of A2-73 fumarate salt.

Dosage forms also encompass those formulated for subcutaneous and/or intramuscular injection. For example, an intramuscular dosage form may comprise A2-73 in the free base form, dissolved in an oil matrix for intramuscular injection, or alternatively prepared as a suspension of the free base for intramuscular injection. A dosage form formulated for subcutaneous or intramuscular injection may comprise A2-73 in a salt or free base form as disclosed herein, prepared as microspheres using methods known in the art. Alternatively, A2-73 in free base or salt form may be coated, for example using Atomic Layer Deposition (ALD) techniques, with a thin layer coating such as a coating of zinc oxide, and used in a formulation for subcutaneous or intramuscular injection. Alternatively, A2-73 free base may be dissolved in a biodegradable polymer matrix, and then implanted subcutaneously (or used in a transdermal patch as detailed further below).

IV. Methods of Administering A2-73 and Methods of Treating

One aspect of the disclosure encompasses a method of administering A2-73 to a subject. The method comprises administering the A2-73 to the subject in a dosage form comprising a crystalline form of A2-73 selected from A2-73 freebase and A2-73 salt.

Dosage forms can be as described in Section III above. The dosage forms can be formulated for immediate or extended release, and can be formulated for oral, transdermal, subcutaneous, or other forms of administration. Formulations can be as described in Section II above.

Extended release dosage forms comprising crystalline A2-73 can administer A2-73 over a period of about two weeks, 30 days, about 45 days, about 60 days, about 90 days, or about 120 to about 180 days 120 to about 180 days.

In some aspects, the method comprises administering a topical dosage form. The topical dosage form can be a transdermal patch. The transdermal patch can be replaced daily, weekly, or longer. In some aspects, the transdermal patch can maintain a level of A2-73 in the blood of the subject for a period of time ranging from about 5 ng/ml to about 15 ng/ml and particularly about 10 ng/ml can be maintained.

The crystalline form of A2-73 can also be administered orally using a dosage form formulated for oral administration. Preferably, a dosage form is an enteric coated oral formulation.

The enteric coated oral dosage form can be administered every other day. The dosage form can deliver about 15 to about 30 mg/day of A2-73. Further, when formulated for extended release of A2-73, the oral dosage form could deliver A2-73 for a period of time can range from about 1 day to about 7 days, about 48 hours, about 72 hours, or greater.

One aspect of the disclosure encompasses a method of treating Alzheimer's disease in a subject in need thereof, the method comprising administering a dosage form comprising a therapeutically effective amount of a crystalline form of A2-73 selected from A2-73 freebase and A2-73 salt.

One aspect of the disclosure encompasses a method of treating a progressive dementia in a subject in need thereof, the method comprising administering a dosage form comprising a therapeutically effective amount of a crystalline form of A2-73 selected from A2-73 freebase and A2-73 salt.

V. Treating a Neurodegenerative Disease

Sig-1R expression or activity are linked to neurodegeneration, and the activation of Sig-1R is associated with neuroprotection in different in vitro and in vivo models, employing different types of pharmacological Sig-1R activators with different pharmacological profiles. The inventors have surprisingly discovered that A2-73, a mixed muscarinic receptor ligand and Sig-1R agonist, can be used to treat neurodegenerative disease. As such, any of the crystalline forms of A2-73, and topical and oral dosage forms as disclosed can be administered to a subject in need thereof, for neuroprotection including treatment of a neurodegenerative disease.

As such, one aspect of the disclosure encompasses a pharmaceutical composition for the treatment of a neurodegenerative disease. The composition comprises an anti-neurodegenerative effective amount of A2-73. The A2-73 can be crystalline polymorph of A2-73, and can be a freebase or a salt. Preferably, the A2-73 is a hydrochloride salt of A2-73.

The anti-neurodegenerative effective amount can range from about 0.5 mg to about 20 mg, about 1 mg to about 60 mg, about 30 mg to about 50 mg, or about 3 mg to about 5 mg.

Another aspect of the disclosure encompasses a dosage form comprising an amount of A2-73 effective for the treatment of a neurodegenerative disease. The amount of A2-73 in the dosage form can be from about 0.01 to about 10 mg/kg.

Another aspect of the disclosure encompasses a method of treating an anti-neurodegenerative disease in a subject in need thereof comprising administering to the subject an anti-neurodegenerative effective amount of A2-73. The neurodegenerative disease can be selected from Alzheimer's disease, Parkinson's disease, prion diseases, Huntington's disease, motor neuron diseases (MND) such as amyotrophic lateral sclerosis, spinocerebellar ataxia (SCA), and spinal muscular atrophy (SMA).

The anti-neurodegenerative effective amount of A2-73 can range from about 0.5 mg/day to about 100 mg/day, from about 1 to about 60 mg/day, from about 20 to about 50 mg/day, from about 20 to about 30 mg/day, or from about 15 to about 25 mg/day. Administering the anti-neurodegenerative effective amount of A2-73 can provide blood levels of about 10 ng/ml, about 12 ng/ml, about of A2-73.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described cells and methods without departing from the scope of the invention, it is intended that all matter contained in the above description and in the examples given below, shall be interpreted as illustrative and not in a limiting sense.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

The term "subject" as used herein refers to a mammalian subject, including without limitation a human, a non-human primate, a mouse, a rat, guinea pig, and a dog.

As used herein, the terms "extended" or "slow" release or delivery are used interchangeably, and can be understood in contrast to an immediate release composition. In an extended release formulation, the active ingredient is gradually, continuously liberated over time, at a rate appropriate for the intended use of the dosage form. In particular, the term indicates that the formulation does not release the full dose of the active ingredient immediately after dosing, and that the formulation allows a reduction in dosage frequency. A slow or extended release, used synonymously with prolonged action, sustained release, or modified release, dosage form is a dosage form that allows a reduction in dosing frequency or a significant increase in patient compliance or therapeutic performance as compared to that presented as an immediate release dosage form (e.g., as a solution or an immediate drug-releasing, conventional solid dosage form).

EXAMPLES

The publications discussed above are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1

Preparation of Form I, Hydrochloride Salt

Form I can be obtained via crystallization of Anavex2-73 from anhydrous solvents, for example, isopropyl alcohol (IPA). At 70° C., Form I can be obtained, for example, from IPA containing up to at least 2.5% v/v water. Form I can also be obtained via sublimation. Some examples of Form I preparation follow:

(i) Example 1.

Approximately 100 mg of Anavex2-73 was weighed into a sample vial, to which 0.5 mL or 1 mL of 2-ethoxyethanol, 1-propanol, acetone, acetonitrile, dichloromethane, dimethyl sulfoxide, ethanol, N,N'-dimethylacetamide, dimethylformamide, N-methyl-2-pyrrolidone or tert-butanol was added. To these vials additional Anavex2-73 was added, if needed, to ensure a mobile slurry was observed. The slurries were agitated for ca. 72 hours using an incubator shaker with temperature cycling employed between ambient temperature (about 20 to 25° C.) and 40° C. (2 hours at each temperature). After ca. 72 hours of temperature cycling the saturated solutions were separated from the slurries using a 0.45 µm syringe filter. To approximately ¼$^{th}$ of each filtrate, tert-butyl methyl ether was added to precipitate out Form I, which was characterized by XRPD.

(ii) Example 2.

Approximately 100 mg of Anavex2-73 was weighed into a sample vial, to which 0.5 mL or 1 mL of 2-ethoxyethanol, 1-propanol, acetone, acetonitrile, dichloromethane, dimethyl sulfoxide, ethanol, N,N'-dimethylacetamide, dimethylformamide, N-methyl-2-pyrrolidone or tert-butanol was added. To these vials additional Anavex2-73 was added, if needed, to ensure a mobile slurry was observed. The slurries were agitated for ca. 72 hours using an incubator shaker with temperature cycling employed between ambient temperature and 40° C. (2 hours at each temperature). After ca. 72 hours of temperature cycling, the slurries were filtered through a 0.45 µm filter to isolate the Form I precipitate, which was characterized by XRPD.

(iii) Example 3.

Anavex2-73 is slurried in IPA containing ca. 2.5% v/v water (or less) and stirred for 20 hrs. at 70° C. After which, the Form I precipitate is isolated by filtration, which was characterized by XRPD.

(iv) Example 4.

Approximately 100 mg of Anavex2-73 was heated to approximately 200° C. in a 5 mL beaker, topped with ice, under atmospheric pressure. The residue was collected and characterized by XRPD.

Example 2

Preparation of Form II, Hydrochloride Salt

Form II can be obtained via crystallization of Anavex2-73 from organic solvent:water mixtures, for example, isopropyl alcohol (IPA):water (90:10). It can also be obtained via air evaporation at ambient temperature from 1-butanol, chloroform, ethanol or tert-butanol. Examples of Form II preparation follow:

(i) Example 1.

Approximately 100 mg of Anavex2-73 was weighed into a sample vial, to which 0.5 mL or 1 mL of water, IPA:water (95:5 v/v) or IPA:water (97.5:2.5 v/v) was added. To this vial additional Anavex2-73 was added, if needed, to ensure a mobile slurry was observed. The slurries were agitated for ca. 72 hours using an incubator shaker with temperature cycling employed between ambient temperature and 40° C. (2 hours at each temperature). After ca. 72 hours of temperature cycling the saturated solutions were separated from the slurries using a 0.45 µm syringe filter. To approximately ¼$^{th}$ of each filtrate, tert-butyl methyl ether, or in the case of water, THF was added to precipitate out Form II, which was characterized by XRPD.

(ii) Example 2.

Approximately 100 mg of Anavex2-73 was weighed into a sample vial, to which 0.5 mL or 1 mL of IPA containing 2.5 to 10% v/v water. To these vials additional Anavex2-73 was added, if needed, to ensure a mobile slurry was observed. The slurries were agitated for ca. 72 hours using an incubator shaker with temperature cycling employed between ambient temperature and 40° C. (2 hours at each temperature). After ca. 72 hours of temperature cycling, the slurries were filtered through a 0.45 µm filter to isolate the Form II precipitate, which was characterized by XRPD.

(iii) Example 3.

Anavex2-73 was slurried in IPA containing ca. 2.5 to 92.5% v/v water and stirred for 20 hrs at a temperature of 20° C. After which, the Form II precipitate was isolated by filtration, which was characterized by XRPD.

(iv) Example 4.

Anavex2-73 is slurried in IPA containing ca. 7.5 to 45% v/v water and stirred for 20 hrs. at a temperature of 70° C. After which, the Form II precipitate is isolated by filtration, which was characterized by XRPD.

(v) Example 5.

Form II was produced on a 250 mg scale using both IPA:water (95:5% v/v) and IPA:water (97.5:2.5% v/v). Approximately 250 mg of Anavex2-73 was weighed into 20 mL scintillation vials. To each vial was added 2.5 mL of either IPA:water (95:5% v/v) or IPA:water (97.5:2.5% v/v). The slurries were agitated for ca. 48 hours using an incubator shaker with temperature cycling employed between ambient temperature and 40° C. (2 hours at each temperature). After ca. 48 hours of temperature cycling the saturated solutions were separated from the slurries. The saturated solutions were then allowed to evaporate at ambient temperature. The residual solid material after temperature cycling was analyzed by XRPD. The residual solid was allowed to air dry at ambient temperature, and once again, analyzed by XRPD.

Example 3

Preparation of Form III, Chloride Salt

Form III can be obtained via crystallization of Anavex2-73 from water and isopropyl alcohol (IPA) at 20° C.

In some aspects, preparation of Form III follows:

(i) Example 1.

In one aspect, an example of preparation of Form III is: Approximately 100 mg of Anavex2-73 was weighed into a sample vial, to which 0.5 mL of water was added. To this vial additional Anavex2-73 was added to ensure a mobile slurry was observed. The slurry was agitated for ca. 72 hours using an incubator shaker with temperature cycling employed between ambient temperature and 40° C. (2 hours at each temperature). After ca. 72 hours of temperature cycling the saturated solution was separated from the slurry using a 0.45 μm syringe filter. Approximately ¼th of the filtrate was allowed to evaporate at ambient temperature (ca. 20° C.). XRPD data was collected for solid residue.

(ii) Example 2.

In another aspect, an example of preparation of Form III is: Anavex2-73 is slurried in IPA and stirred for 20 hours at a temperature of 20° C. After which, the Form III precipitate is isolated by filtration and characterized by XRPD.

(iii) Example 3.

In one aspect, an example of preparation of Form III is: Form III material was produced on a 500 mg scale using water. Approximately 500 mg of Anavex2-73 was weighed into a 20 mL scintillation vial and 600 μL of water added. The slurry was then agitated for ca. 48 hours using an incubator shaker with temperature cycling employed between ambient temperature and 40° C. (2 hours at each temperature). After ca. 24 hours a thin slurry was noted and an additional 130 mg of Anavex2-73 was added to the slurry. After the full 48 hours of temperature cycling the saturated solution was separated from the slurry. The saturated solution was then allowed to evaporate at ambient temperature. The residual solid material after temperature cycling was analyzed by XRPD. The residual solid was allowed to air dry at ambient temperature and re-analyzed by XRPD.

Example 4

Preparation of Form IV, Hydrochloride Salt

Form IV was obtained via Anavex2-73 lyophilization from water. In one aspect, preparation of Form IV follows:

(i) Example 1.

Approximately 20 mg of Anavex2-73 was weighed into a 2 mL sample vial and dissolved in 200 μL deionized water. The sample was then placed in a freezer at −20° C. Once frozen, the sample was lyophilized and characterized by XRPD to assess the crystallinity of the material.

Example 5

Preparation of Form V, Hydrochloride Salt

Form V was obtained via Anavex2-73 rotary evaporation from dichloromethane. In one aspect, preparation of Form V follows:

(i) Example 1.

Approximately 20 mg of Anavex2-73 was dissolved in 300 μL of dichloromethane and allowed to rapidly evaporate in a fume-hood, utilizing a rotary evaporator. XRPD data was collected for the resulting solid material.

Example 6

Preparation of Form VI, Hydrochloride Salt

Form VI was obtained upon rapid cooling of an aqueous solution of Anavex2-73 to 5° C. Specific example of Form VI preparation follows:

(i) Example 1.

Approximately 100 mg of Anavex2-73 was weighed into a sample vial, to which 0.5 mL of water was added. To this vial additional Anavex2-73 was added to ensure a mobile slurry was observed. The slurry was agitated for ca. 72 hours using an incubator shaker with temperature cycling employed between ambient temperature and 40° C. (2 hours at each temperature). After ca. 72 hours of temperature cycling the saturated solution was separated from the slurries using a 0.45 μm syringe filter. Approximately ¼th of the filtrate was placed in a 5° C. refrigerator and stored until solid precipitate was observed. XRPD data was collected for the damp precipitate to prevent potential desolvation.

Example 7

Preparation of Form VII, Hydrochloride Salt

Form VII was obtained via air evaporation of Anavex2-73 from methanol. Specific example of Form VII preparation follows:

(i) Example 1.

Approximately 100 mg of Anavex2-73 was weighed into a sample vial, to which 0.5 mL of methanol was added. To this vial additional Anavex2-73 was added to ensure a mobile slurry was observed. The slurry was agitated for ca. 72 hours using an incubator shaker with temperature cycling employed between ambient temperature and 40° C. (2 hours at each temperature). After ca. 72 hours of temperature cycling the saturated solution was separated from the slurry using a 0.45 μm syringe filter. Approximately $\frac{1}{4}^{th}$ of the filtrate was allowed to evaporate at ambient temperature (ca. 20° C.). XRPD data was collected for solid residue.

Example 8

Preparation of Form VIII, Hydrochloride Salt

Form VIII is obtained by slurrying Anavex2-73 in water at 20° C. Specific examples of Form VIII preparation follow:

(i) Example 1.

Anavex2-73 was added to ca. 1.5 mL of water at 20° C. until a slurry was obtained, with the suspended material analyzed using XRPD after slurrying for 20 hrs.

(ii) Example 2.

Anavex2-73 is completely dissolved in water and allowed to air evaporate at 20° C. until precipitation is observed. The resulting Form VIII is isolated while still wet with water, as once dried, it converts to Form I. XRPD patterns were collected pre/post-drying.

Example 9

Preparation of Form I, Freebase

Into a 250 mL separating funnel, 150 mL of EtOAc and 500 mg of A2-73 (hydrochloride salt) were added, followed by 100 mL of concentrated $NaHCO_3$. The resulting mixture was shaken and the aqueous layer was removed. Two additional 100 mL aliquots of concentrated $NaHCO_3$ were added, and each time, the mixtures were shaken, and the aqueous layer removed.

The organic layer was washed with 100 mL of deionized water, and then the organic layer was dried using magnesium sulphate, then filtered. The filtrate was collected and the EtOAc was removed using a rotary evaporator. A clear oil was obtained post-evaporation, which was dried under a stream of nitrogen, yielding a white solid. The resulting solid was weighed and analyzed by XRPD.

Data show A2-73 freebase is (i) crystalline, (ii) not highly water soluble (unlike the HCl salt), and (iii) non-hygroscopic. Its molecular weight (MW) of 280 is below the accepted general transdermal cutoff MW of about 400, and its calculated Log P is 3.5. Additionally, as A2-73 freebase only has 2 hydrogen bond donor/acceptor sites, it is under the general rule-of-thumb limit of about 5 hydrogen bond donor/acceptor sites, which would potentially restrict transdermal delivery.

Therefore, A2-73 freebase is a useful active pharmaceutical ingredient in a transdermal extended-release formulation. Reference is made to an oral dose of 20 mg of A2-73. Transdermal dosing 2× per week at a significantly lower administration dose based in, it is believed, avoiding first-pass liver or hepatic first pass effect is a useful result of the present invention. Transdermal patch matrix layer may usefully contain, by way of non-limiting example, oleyl oleate, povidone K90, levulinic acid, crosslinked poly [acrylic acid-co-butylacrylate-co-(2-ethylhexyl)acrylate-co-vinylacetate]. Also noted are absorption enhancers (penetration enhancers) in the matrix formulation to generate a high flux of the active compounds when the system is applied to the skin. Typical known enhancers are ethanol, glycerolmonolaurate, DMF, polyethylenglycole monolaurate, etc.

Example 10

Preparation of Sulfate Form I

A2-73 sulfate Form I was obtained via addition of sulfuric acid (in THF) to A2-73 freebase in ethanol, THF, acetone, 2-propanol or 2-ethoxyethanol. Specific examples of A2-73 sulfate Form I preparation follow:

(i) Example 1.

Approximately 200 mg of A2-73 freebase was weighted into a 20 mL scintillation vial, after which, 4 mL of ethanol was added to the vial. The apparent pH of the resulting solution was determined using a pH meter. Sulfuric acid stock solution (1119.4 μL of a solution containing 4.1 μL of 98% sulfuric acid per 74.6 μL of THF) was added to the vial, followed by agitation. The apparent pH of the solution was once again measured. The sample was then temperature-cycled between ambient and 40° C. for ca. 24 hours. As no solid was observed at the end of ca. 24 hours, the sample was left uncapped in a fume hood and allowed to air-evaporate for ca. 72 hours, followed by drying under a nitrogen stream. As no solid was observed, the sample was placed in a vacuum oven for one hour, resulting in a colorless, sticky solid. The sample was further dried in a vacuum oven for ca. 4 hours, and a white solid was obtained, which was characterized by XRPD.

(ii) Example 2.

A stock solution of sulfuric acid was prepared in THF (272.0 μL of sulfuric acid in 4728.0 μL THF). Separately, 20 mg of the A2-73 freebase was weighed into 1.5 mL HPLC vials, and to each vial, 300 μL of the appropriate solvent (THF, ethanol, acetone, 2-propanol or 2-ethoxyethanol) was added, along with 74.6 μL of acid stock solution (1.05 equivalents of acid). The samples were temperature-cycled between ambient and 40° C. in 4-hour cycles for 72 hours. XRPD data was collected for the isolated precipitate.

Example 11

Preparation of Sulfate Form II

A2-73 sulfate Form II was obtained via addition of sulfuric acid (in THF) to A2-73 freebase in acetonitrile. Specific example of A2-73 sulfate Form II preparation follows:

(i) Example 1.

A stock solution of sulfuric acid was prepared in THF (272.0 μL of sulfuric acid in 4728.0 μL THF). Separately, 20 mg of the A2-73 freebase was weighed into a 1.5 mL HPLC vial, and 300 μL of acetonitrile was added, along with 74.6 μL of acid stock solution (1.05 equivalents of acid). The sample was temperature-cycled between ambient and 40° C. in 4-hour cycles for 72 hours, and the resulting precipitate was analyzed by XRPD.

Example 12

Preparation of Mesylate Form I

A2-73 mesylate Form I was obtained via addition of methane sulfonic acid (in THF) to A2-73 freebase in ethanol, acetonitrile, acetone, 2-propanol or 2-ethoxyethanol. Specific example of A2-73 mesylate Form I preparation follows:

(i) Example 1.

A stock solution of methane sulfonic acid was prepared in THF (324.4 μL of methane sulfonic acid in 4675.6 μL THF). Separately, 20 mg of the A2-73 freebase was weighed into 1.5 mL HPLC vials, to which 300 μL of the appropriate solvent (ethanol, acetonitrile, acetone, 2-propanol or 2-ethoxyethanol) was added, along with 74.6 μL of acid stock solution (1.05 equivalents of acid). The sample was temperature-cycled between ambient and 40° C. in 4-hour cycles for 72 hours. The samples were filtered, and approximately 100 μL of the mother liquor from each salt formation reaction was added to 2 mL glass vials. The vials were left uncapped in a cupboard to allow evaporation. Observed solids post-evaporation were analyzed by XRPD.

Example 13

Preparation of Oxalate Form I

A2-73 oxalate Form I was obtained via addition of oxalic acid (in THF) to A2-73 freebase in THF. Specific example of A2-73 oxalate Form I preparation follows:

(i) Example 1.

A stock solution of oxalic acid was prepared in THF (450.2 μL of oxalic acid in 4549.8 μL THF). Separately, 20 mg of the A2-73 freebase was weighed into a 1.5 mL HPLC vial, to which 300 μL of THF was added, along with 74.6 μL of acid stock solution (1.05 equivalents of acid). The sample was temperature-cycled between ambient and 40° C. in 4-hour cycles for 72 hours, and the resulting precipitate was analyzed by XRPD.

Example 14

Preparation of Oxalate Form II

A2-73 oxalate Form II was obtained via addition of oxalic acid (in THF) to A2-73 freebase in acetone. Specific example of A2-73 oxalate Form II preparation follows:

(i) Example 1.

A stock solution of oxalic acid was prepared in THF (450.2 μL of oxalic acid in 4549.8 μL THF). Separately, 20 mg of the A2-73 freebase was weighed into a 1.5 mL HPLC vial, to which 300 μL of acetone was added, along with 74.6 μL of acid stock solution (1.05 equivalents of acid). The sample was temperature-cycled between ambient and 40° C. in 4-hour cycles for 72 hours, and the resulting precipitate was analyzed by XRPD.

Example 15

Preparation of Oxalate Form III

A2-73 oxalate Form III was obtained via addition of oxalic acid (in THF) to A2-73 freebase in ethanol. Specific examples of A2-73 oxalate Form III preparation follow:

(i) Example 1.

Approximately 200 mg of A2-73 freebase was weighted into a 20 mL scintillation vial, after which, 4 mL of ethanol was added to the vial. The apparent pH of the resulting solution was determined using a pH meter. Oxalic acid stock solution (1119.4 µL of a solution containing 6.72 mg of phosphoric acid per 74.6 µL of THF) was added (1.05 equivalents) to the vial, followed by agitation. The apparent pH of the solution was once again measured. The sample was then temperature-cycled between ambient and 40° C. for ca. 24 hours, with precipitated solid isolated at the end of ca. 24 hours and air-dried for ca. 72 hours, followed by characterization by XRPD.

(ii) Example 2.

A stock solution of oxalic acid was prepared in THF (450.2 µL of oxalic acid in 4549.8 µL THF). Separately, 20 mg of the A2-73 freebase was weighed into a 1.5 mL HPLC vial, to which 300 µL of ethanol was added, along with 74.6 µL of acid stock solution (1.05 equivalents of acid). The sample was temperature-cycled between ambient and 40° C. in 4-hour cycles for 72 hours, and the resulting precipitate was analyzed by XRPD.

(iii) Example 3.

A stock solution of oxalic acid was prepared in THF (450.2 µL of oxalic acid in 4549.8 µL THF). Separately, 20 mg of the A2-73 freebase was weighed into a 1.5 mL HPLC vial, to which 300 µL of ethanol was added, along with 74.6 µL of acid stock solution (1.05 equivalents of acid). The sample was temperature-cycled between ambient and 40° C. in 4-hour cycles for 72 hours. The sample was filtered and approximately 100 µL of the filtrate was added to a 2 mL glass vial. The vial was left uncapped in a cupboard to allow evaporation. Observed solid post-evaporation was analyzed by XRPD.

(iv) Example 4.

A stock solution of oxalic acid was prepared in THF (450.2 µL of oxalic acid in 4549.8 µL THF). Separately, 20 mg of the A2-73 freebase was weighed into a 1.5 mL HPLC vial, to which 300 µL of ethanol was added, along with 74.6 µL of acid stock solution (1.05 equivalents of acid). The sample was temperature-cycled between ambient and 40° C. in 4-hour cycles for 72 hours. The sample was filtered and approximately 100 µL of filtrate was measured into a 1.5 mL HPLC vial. The vial was capped and placed in a fridge at ca. 5° C. for ca. 24 hours. The sample was checked periodically and observed solid was analyzed by XRPD. If the sample remained a solution it was placed in a freezer at ca. −20° C. for ca. 24 hours. The sample was checked periodically and observed solid was analyzed by XRPD.

(v) Example 5.

A stock solution of oxalic acid was prepared in THF (450.2 µL of oxalic acid in 4549.8 µL THF). Separately, 20 mg of the A2-73 freebase was weighed into a 1.5 mL HPLC vial, to which 300 µL of ethanol was added, along with 74.6 µL of acid stock solution (1.05 equivalents of acid). The sample was temperature-cycled between ambient and 40° C. in 4-hour cycles for 72 hours. The sample was filtered and approximately 100 µL of the filtrate was transferred into a 1.5 mL HPLC vial. A 100 µL aliquot of tert-methyl ether was added until precipitation was observed. XRPD data was collected for the precipitate.

Example 16

Preparation of Dihydrogen Phosphate Form I

A2-73 dihydrogen phosphate Form I was obtained via addition of phosphoric acid (in THF) to a solution of A2-73 freebase in THF, ethanol, acetonitrile, acetone, 2-propanol or 2-ethoxyethanol.

Specific examples of A2-73 dihydrogen phosphate Form I preparation follow:

(i) Example 1.

Approximately 300 mg of A2-73 freebase was weighted into a 20 mL scintillation vial, after which, 4 mL of acetone was added to the vial. The apparent pH of the resulting solution was determined using a pH meter. Phosphoric acid stock solution (1119.4 µL of a solution containing 7.31 mg of phosphoric acid per 74.6 µL of acetone) was added (1.05 equivalents) to the vial, followed by agitation. The apparent pH of the solution was once again measured. The sample was then temperature-cycled between ambient and 40° C. for ca. 24 hours, with precipitated solid isolated at the end of ca. 24 hours and air dried for ca. 72 hours, followed by characterization by XRPD.

(ii) Example 2.

A stock solution of phosphoric acid was prepared in THF (490 µL of phosphoric acid in 4510 µL THF). Separately, 20 mg of the A2-73 freebase was weighed into 1.5 mL HPLC vials, to which 300 µL of the appropriate solvent (THF, ethanol, acetonitrile, acetone, 2-propanol or 2-ethoxyethanol) was added, along with 74.6 µL of acid stock solution (1.05 equivalents of acid). The sample was temperature-cycled between ambient and 40° C. in 4-hour cycles for 72 hours, and the resulting precipitate was analyzed by XRPD.

Example 17

Preparation of Edisylate Form I

A2-73 edisylate Form I was obtained via addition of 1,2-ethanedisulfonic acid (in THF) to A2-73 freebase in ethanol, acetonitrile, acetone, 2-propanol or 2-ethoxyethanol. Specific examples of A2-73 edisylate Form I preparation follow:

(i) Example 1.

A stock solution of 1,2-ethanedisulfonic was prepared in THF (1170.7 µL of 1,2-ethanedisulfonic acid in 3829.3 µL THF). Separately, 20 mg of the A2-73 freebase was weighed into 1.5 mL HPLC vials, to which 300 µL of the appropriate solvent (ethanol, acetonitrile, acetone, 2-propanol, or 2-ethoxyethanol) was added, along with 74.6 µL of acid stock solution (1.05 equivalents of acid). The samples were temperature-cycled between ambient and 40° C. in 4-hour cycles for 72 hours. The samples were filtered and approximately 100 µL of each filtrate was added to 2 mL glass vials. The vials were left uncapped in a cupboard to allow evaporation. Observed solid post-evaporation was analyzed by XRPD.

(ii) Example 2.

A stock solution of 1,2-ethanedisulfonic was prepared in THF (1170.7 µL of 1,2-ethanedisulfonic acid in 3829.3 µL THF). Separately, 20 mg of the A2-73 freebase was weighed into 1.5 mL HPLC vials, to which 300 µL of the appropriate solvent (ethanol, acetone or 2-propanol) was added, along with 74.6 μL of acid stock solution (1.05 equivalents of acid). The samples were temperature-cycled between ambient and 40° C. in 4-hour cycles for 72 hours. The samples were filtered and approximately 100 μL of each filtrate was measured into a 1.5 mL HPLC vials. The vials were capped and placed in a fridge at ca. 5° C. for ca. 24 hours. The samples were checked periodically and observed solids were analyzed by XRPD. Samples which appeared as solutions were placed in a freezer at ca. −20° C. for ca. 24 hours. The samples were checked periodically and observed solids were analyzed by XRPD.

Example 18

Preparation of Benzoate Form I

A2-73 benzoate Form I was obtained via addition of benzoic acid (in THF) to A2-73 freebase in THF, acetonitrile or acetone. Specific example of A2-73 benzoate Form I preparation follows:
(i) Example 1.
A stock solution of benzoic acid was prepared in THF (610.6 μL of benzoic acid in 4389.4 μL THF). Separately, 20 mg of the A2-73 freebase was weighed into 1.5 mL HPLC vials, to which 300 μL of the appropriate solvent (THF, acetonitrile or acetone) was added, along with 74.6 μL of acid stock solution (1.05 equivalents of acid). The samples were temperature-cycled between ambient and 40° C. in 4-hour cycles for 72 hours. The samples were filtered and approximately 100 μL of each filtrate was added to 2 mL glass vials. The vials were left uncapped in a cupboard to allow evaporation. Observed solid post-evaporation was analyzed by XRPD.

Example 19

Preparation of Hydrogen Fumarate Form I

A2-73 fumarate Form I was obtained via addition of fumaric acid (in THF) to A2-73 freebase in ethanol or THF. Specific example of A2-73 fumarate Form I preparation follows:
(i) Example 1.
Approximately 200 mg of A2-73 freebase was weighted into a 20 mL scintillation vial, after which, 4 mL of ethanol was added to the vial. The apparent pH of the resulting solution was determined using a pH meter. Fumaric acid stock solution (1119.4 μL of a solution containing 8.66 mg of fumaric acid per 74.6 μL of ethanol) was added (1.05 equivalents) to the vial, followed by agitation. The apparent pH of the solution was once again measured. The sample was then temperature-cycled between ambient and 40° C. for ca. 24 hours. As no solid was observed at the end of ca. 24 hours, the sample was left uncapped in a fume hood and allowed to air-evaporate for ca. 72 hours, followed by characterization by XRPD.

A stock solution of fumaric acid was prepared in THF (580.3 μL of fumaric acid in 4419.7 μL THF). Separately, 20 mg of the A2-73 freebase was weighed into a 1.5 mL HPLC vial, to which 300 μL of THF was added, along with 74.6 μL of acid stock solution (1.05 equivalents of acid). The sample was temperature-cycled between ambient and 40° C. in 4-hour cycles for 72 hours. The sample was filtered and approximately 100 μL was transferred to a 2 mL glass vial. The vial was left uncapped in a cupboard to allow evaporation. Observed solid post-evaporation was analyzed by XRPD.

A stock solution of fumaric acid was prepared in THF (580.3 μL of fumaric acid in 4419.7 μL THF). Separately, 20 mg of the A2-73 freebase was weighed into a 1.5 mL HPLC vial, to which 300 μL of THF was added, along with 74.6 μL of acid stock solution (1.05 equivalents of acid). The sample was temperature-cycled between ambient and 40° C. in 4-hour cycles for 72 hours. The sample was filtered and approximately 100 μL of the filtrate was transferred into a 1.5 mL HPLC vial. A 100 μL aliquot of tert-butyl methyl ether was added until precipitation was observed, and the resulting precipitate was analyzed by XRPD.

Example 20

Preparation of Fumarate Form II

A2-73 fumarate Form II was obtained via addition of fumaric acid (in THF) to A2-73 freebase in ethanol. Specific example of A2-73 fumarate Form II preparation follows:
(i) Example 1.
A stock solution of fumaric acid was prepared in THF (580.3 μL of fumaric acid in 4419.7 μL THF). Separately, 20 mg of the A2-73 freebase was weighed into a 1.5 mL HPLC vial, to which 300 μL of ethanol was added, along with 74.6 μL of acid stock solution (1.05 eq of acid). The sample was temperature-cycled between ambient and 40° C. in 4-hour cycles for 72 hours, and the resulting precipitate was analyzed by XRPD.

Example 21

Preparation of Hydrogen Fumarate Form III

A2-73 hydrogen fumarate Form III was obtained via addition of fumaric acid (in THF) to A2-73 freebase in IPA. Specific example of A2-73 hydrogen fumarate Form III preparation follows:
(i) Example 1.
Approximately 300 mg of A2-73 freebase was weighted into a 20 mL scintillation vial, after which, 4 mL of IPA was added to the vial. The apparent pH of the resulting solution was determined using a pH meter. Fumaric acid stock solution (1119.4 μL of a 1M fumaric acid stock solution in IPA) was added (1.05 equivalents) to the vial, followed by agitation. The apparent pH of the solution was once again measured. The sample was then temperature-cycled between ambient and 40° C. for ca. 24 hours, with precipitated solid isolated via centrifugation at the end of ca. 24 hours. The isolated solid was air-dried for ca. 72 hours, followed by characterization by XRPD.

A stock solution of fumaric acid was prepared in THF (580.3 μL of fumaric acid in 4419.7 μL THF). Separately, 20 mg of the A2-73 freebase was weighed into a 1.5 mL HPLC vial, to which 300 μL of IPA was added, along with 74.6 μL of acid stock solution (1.05 equivalents of acid). The sample was temperature-cycled between ambient and 40° C. in 4-hour cycles for 72 hours, and the resulting precipitate was analyzed by XRPD.

Example 22

Preparation of Fumarate Form IV

A2-73 fumarate Form IV was obtained via addition of fumaric acid (in THF) to A2-73 freebase in 2-ethoxyethanol. Specific example of A2-73 fumarate Form IV preparation follows:

(i) Example 1.

A stock solution of fumaric acid was prepared in THF (580.3 µL of fumaric acid in 4419.7 µL THF). Separately, 20 mg of the A2-73 freebase was weighed into a 1.5 mL HPLC vial, to which 300 µL of 2-ethoxyethanol was added, along with 74.6 µL of acid stock solution (1.05 equivalents of acid). The sample was temperature-cycled between ambient and 40° C. in 4-hour cycles for 72 hours. The sample was filtered and approximately 100 µL was transferred to a 2 mL glass vial. The vial was left uncapped in a cupboard to allow evaporation. Observed solid post-evaporation was analyzed by XRPD.

Example 23

Anavex2-73 Fumarate Form V

A2-73 fumarate Form V was obtained via addition of fumaric acid (in THF) to A2-73 freebase in IPA. Specific example of A2-73 fumarate Form V preparation follows:
(i) Example 1.
Approximately 300 mg of A2-73 freebase was weighted into a 20 mL scintillation vial, after which, 4 mL of IPA was added to the vial. The apparent pH of the resulting solution was determined using a pH meter. Fumaric acid stock solution (1119.4 µL of a 1M fumaric acid stock solution in IPA) was added (1.05 equivalents) to the vial, followed by agitation. The apparent pH of the solution was once again measured. The sample was then temperature-cycled between ambient and 40° C. for ca. 24 hours, with precipitated solid isolated via centrifugation at the end of ca. 24 hours. The isolated solid was air dried for ca. 72 hours, followed by characterization by XRPD.

Example 24

Transdermal Patch

A 63 year-old male presents with early signs of Alzheimer's disease. He is administered a pharmaceutical composition via transdermal patch containing 100 mg ANAVEX2-73 freebase with a 4 cm2 patch replaced approximately every three days administration for 120 days. Blood levels of about 10 ng/ml are being maintained. His cognitive function stabilizes during that period, with no additional loss detected.

Example 25

Transdermal Patch

A 57 year-old female presents with signs of early onset Alzheimer's disease. She is administered via a 9 cm2 transdermal patch containing a pharmaceutical composition containing 200 mg ANAVEX2-73 freebase with the patch replaced weekly for 180 days. Blood levels of about 12 ng/ml are being maintained. Her cognitive function stabilizes during that period with no additional loss detected.

Example 26

Extended Released Oral Dosage Form

An 84 year old male with unspecified progressive dementia is administered 30 mg of ANAVEX2-73 fumarate in an enteric coated tablet every other day for 180 days. Blood levels reveal about 25 mg per day are being administered. His cognitive function stabilizes during that period with no additional loss detected.

Example 27

Extended Released Oral Dosage Form

An 77 year old female with unspecified progressive dementia is administered 50 mg of ANAVEX2-73 freebase in an enteric coated tablet every other day for 180 days. Blood levels reveal about 20 mg per day are being administered. Hers cognitive function stabilizes during that period with no additional loss detected.

Example 28

Sig1-R Agonist ANAVEX2-73 Enhances Autophagic Activity

Figure 35A:
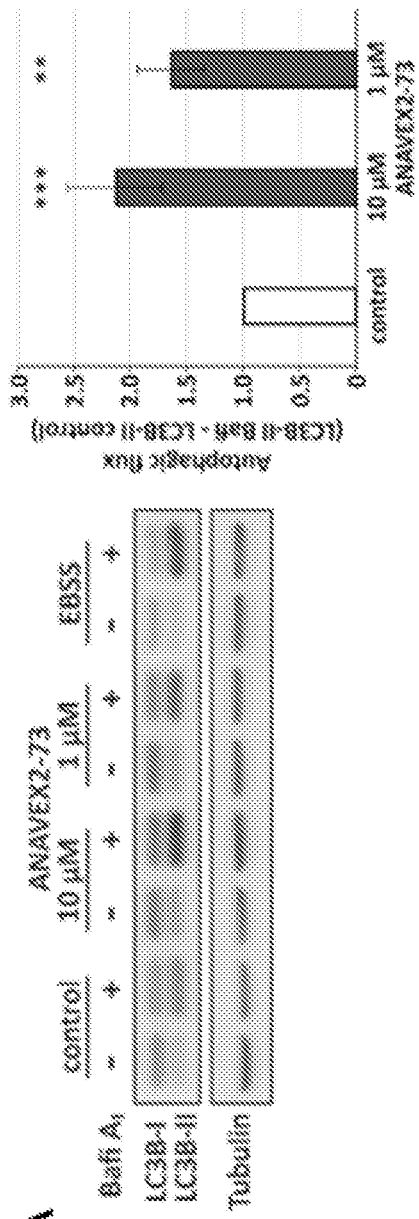
FIG. 35A shows Western blots and a plot quantifying the results of the Western blots of the autophagic flux upon addition of ANAVEX2-73.

To study the effect of ANAVEX2-73 on autophagy, human HeLa cells were treated with the compound and autophagic activity was analyzed by investigating the flux of LC3-II. LC3-II is the lipidated form of LC3, which (partially) stays attached to autophagosomes and thus, gets degraded by lysosomes. Therefore, the quantification of the LC3-II flux, using Bafilomycin $A_1$ (BafiA$_1$; 2 µM) for inhibition of lysosomal degradation, directly corresponds to cellular autophagic activity. As displayed in FIG. 35, ANAVEX2-73 significantly induced autophagic flux when compared to control conditions. There is a concentration-dependent and significant increase in the autophagic-flux following application of ANAVEX2-73: an increase of over 2-fold at 10 µM and over 1.5-fold at 1 µM ANAVEX2-73 (FIG. 35A). As standard positive control to provoke the induction of autophagy, HeLa cells were incubated with EBSS, which resembles nutrient deprivation as autophagy stimulus.

Figure 35B:
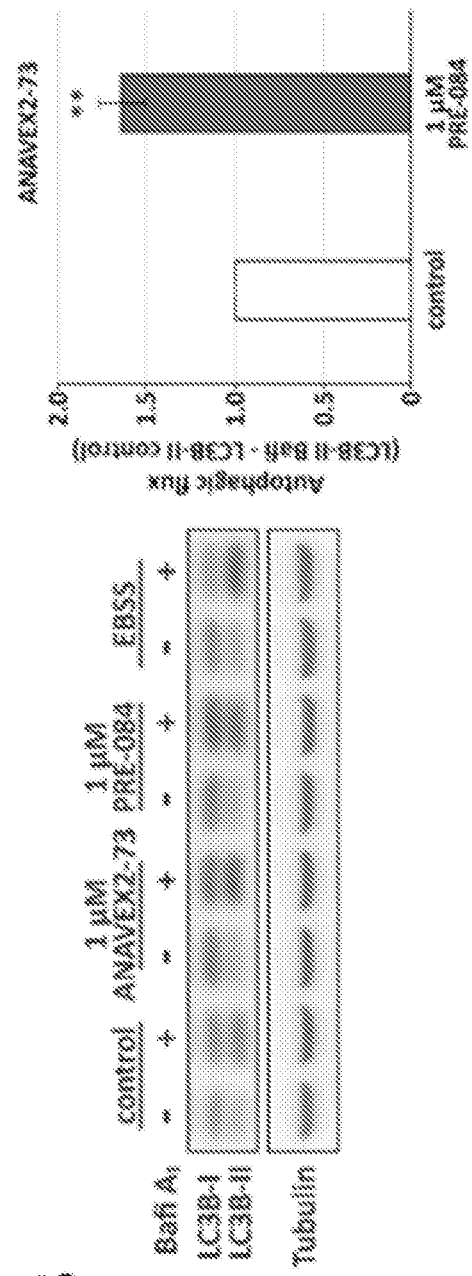
FIG. 35B are Western blots and a plot quantifying the results of the Western blots of the autophagic flux upon addition of PRE-084. Statistics are depicted as mean+/−SD. * $p<0.001$,  $p<0.01$, t-test, n=4.

ANAVEX2-73 and other known experimental Sig-1R agonists were used in the experiments. Such compounds include (+)-pentazocine, (+)-SKF10,047, SA4503 (14243, 4-dimethoxyphenyDethyl]-4-(3-phenylpropyl)piperazine), and PRE-084 (2-morpholin-4-ylethyl 1-phenylcyclohexane-1-carboxylate). In contrast to ANAVEX2-73, PRE-084 and the other experimental compounds are not applicable in clinical studies for various reasons. However, since the Sig-1R ligand PRE-084 exhibits activities in the central nervous system in animal models such as nootropic and antidepressant activities, this compound was included in some of the flux assays as control. It was found that PRE-084 also promotes autophagic flux in HeLa cells (FIG. 35B); PRE-084 induces the autophagic flux at over 1.5 fold at 1 µM, which was comparable with ANAVEX2-73 at the same concentration (FIG. 35B).

Next, the Western blot experiments were complemented by direct visualization of the extent of autophagosome appearance in HEK293 cells. To do so, ANAVEX2-73 (1 µM) was applied to HEK293 cells stably expressing a GFP-LC3B reporter construct. This cell model allows direct monitoring of the accumulation of LC3-II-positive autophagosomal structures upon BafiA$_1$ supplementation by confocal fluorescence microscopy. Indeed, ANAVEX2-73 treatment resulted in an overall increased number of LC3-II-positive puncta and autophagic flux (FIG. 35C).

Taken together, in both independent cell assays and in two different human cell lines, Sig-1R activation induced a significantly increased autophagic flux. Part of the effect of ANAVEX2-73 as Sig-1R ligand could potentially be ascribed to its effects at the muscarinic ACh-receptor. But not much is known about the impact of mACh receptors on autophagy. In fact, so far there is only one report in the literature showing that ACh-induced autophagy has cytoprotective effects through the muscarinic ACh-receptor activated-AMPK-mTOR pathway. On the other hand, our finding that also PRE-084, as an exclusive selective Sig-1R agonist, was inducing autophagic flux, strongly supports ANAVEX2-73's effects on autophagy as being mediated by Sig-1R activation. Moreover, no experimental data exist that an activation of the muscarinic ACh-receptor has beneficial effects on protein aggregation and proteostasis, as clearly ANAVEX2-73 has, as shown in Example 30 below.

Example 29

Figures 36A, 36B:
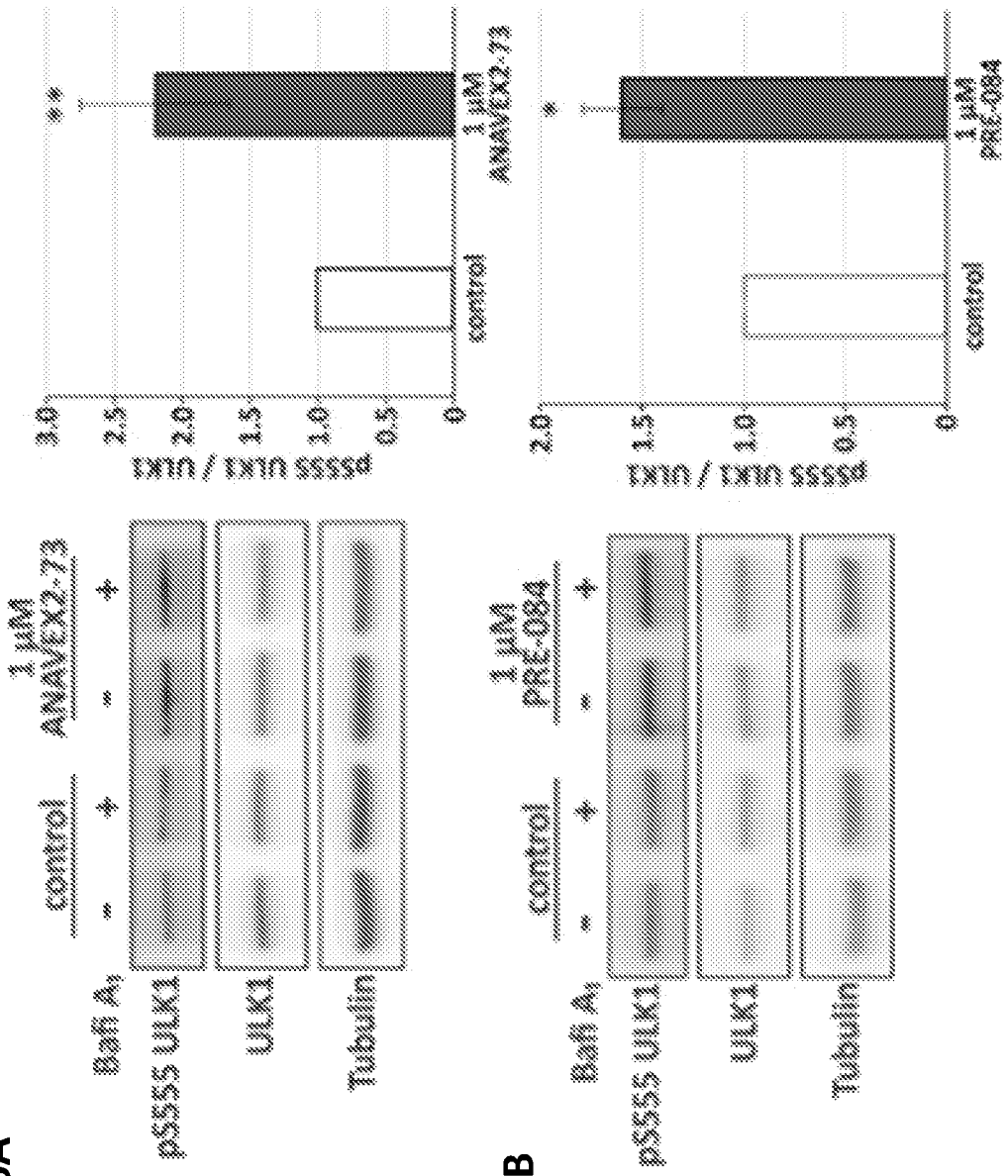
FIG. 36A shows Western blots of ULK1 phosphorylation at serine 555 (pS555) upon treatment of HeLa cells with ANAVEX2-73 and a plot quantifying the results of the Western blots. Statistics are depicted as mean±SD. ** $p<0.01$, t-test, n=4.
FIG. 36B shows Western blots of ULK1 phosphorylation at serine 555 (pS555) upon treatment of HeLa cells with PRE-084. Statistics are depicted as mean±SD. *$p<0.05$, t-test, n=4.

Sig-1R Activation Induces ULK1 Phosphorylation and Affects Expression Levels of Distinct Autophagy Network Factors Activation of the serine/threonine protein kinase ULK1 (unc-51-like kinase 1) via phosphorylation at serine 555 indicates stimulation of the canonical autophagy pathway. ANAVEX2-73 significantly induced ULK1 serine 555 phosphorylation (up to 2-fold at 1 µM; FIG. 36A). PRE-084 was also analyzed as Sig-1R agonist and it was found that it similarly promotes ULK1 serine 555 phosphorylation (up to 1.5 fold at 1 µM FIG. 36B). It has to be mentioned that this activating ULK1 phosphorylation can be inhibited by mTOR as well as stimulated via AMPK kinase. Both are basal physiological sensors of nutritional conditions and key signal transducers of canonical autophagy stimulation. ULK1 is in fact the signal mediating the induction of the formation of the phagophore during the autophagy process and, therefore, a central promoter of autophagy. ULK1 itself functions in a complex with at least three protein partners: FIP200 (focal adhesion kinase family interacting protein of 200 kDa), ATG (autophagy-related protein) 13 (ATG13), and ATG101. The fact that a complex pattern of upstream pathways (including mTOR and AMPK) converge on ULK1, suggests that this complex acts as a node, converting multiple signals into autophagosome formation.

Figure 36C:
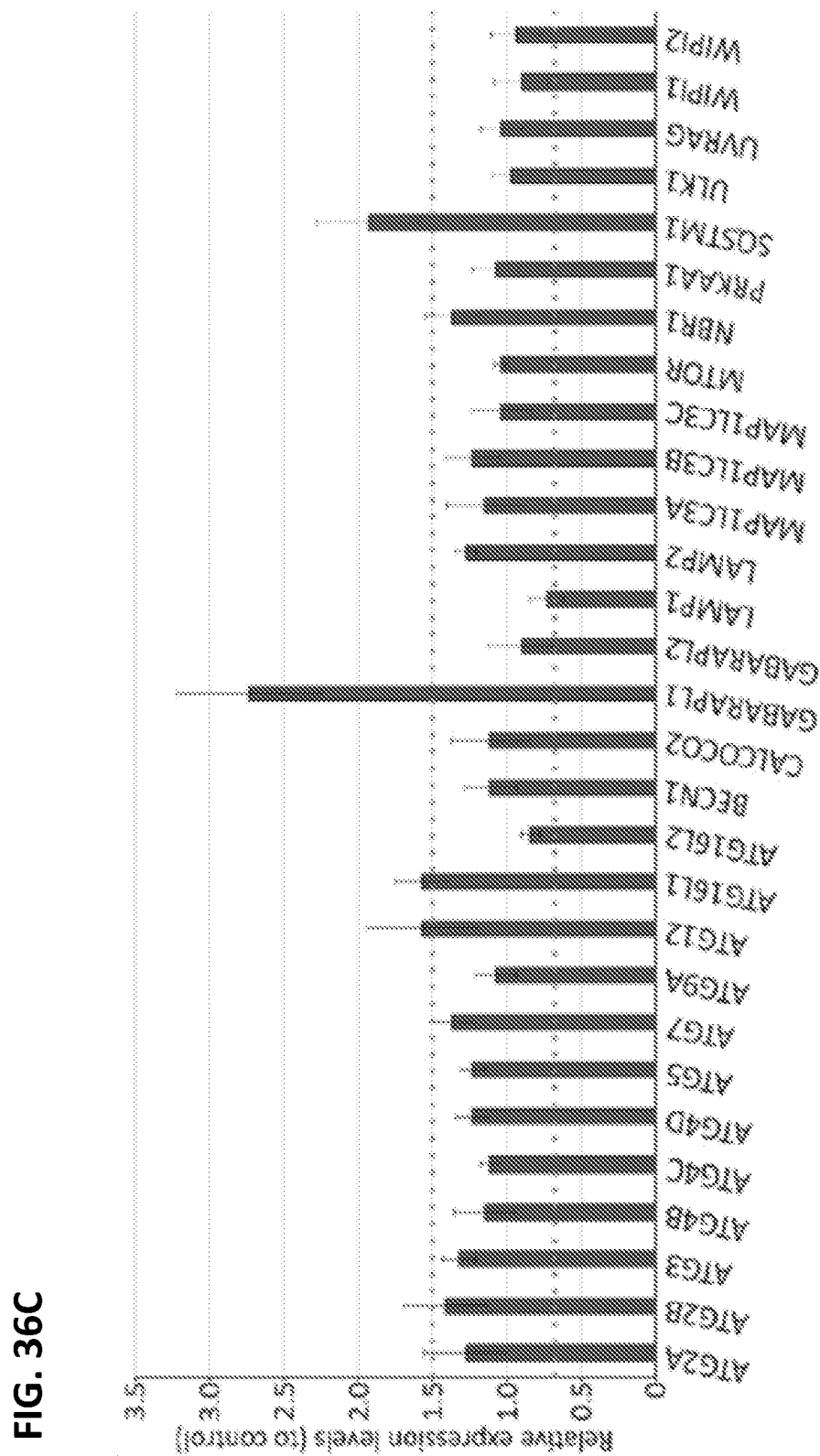
FIG. 36C is a plot depicting the relative expression levels of autophagy network factors analyzed employing the autophagy qPCR array. The expression of each gene is depicted in relation to control cells (set to 1) and the threshold for up- or down-regulation is defined as 1.5 and 0.67, respectively.

In view of the results found by the inventors that Sig-1R activation significantly induces ULK1 phosphorylation and autophagic flux, the relative expression levels of key autophagy network factors representing different set points in the autophagy process was next investigated after treatment of HeLa cells with ANAVEX2-73 employing a PCR autophagy array (FIG. 36C). Most prominently, an ANAVEX2-73-mediated induction of the mRNA expression of GABA Type A Receptor Associated Protein Like 1 (GABARAPL1; expression level of approx. 2.7; cut-off for induction was set at the expression level of 1.5) was found, which, like GABARAP, associates with autophagic vesicles and is involved in the autophagy process.

GABARAPL1 belongs to the human MAP1LC3 family consisting of six ATG8 orthologs, MAP1LC3A, MAP1LC3B, MAP1LC3C and three MAP1LC3 paralogs, the GABA receptor-associated proteins GABARAP1, GABARAPL1 and GABARAPL2 with partially redundant roles in autophagy. In addition, the expression of the ubiquitin and autophagy receptor SQSTM1/p62 involved in selective macroautophagy pathways was enhanced by ANAVEX2-73 (expression level of approx. 2.9). Moreover, there was also a clear tendency towards the induction of ATG12, which is conjugated to ATG5 and is building an autophagosomal protein complex that finally acts together with ATG16L1 in autophagosomal biogenesis. Consistently, the expression of ATG16L1 appeared also enhanced following treatment of the cells with ANAVEX2-73 (FIG. 36C). Moreover, it is clear that none of the autophagy network factors included in this PCR array was downregulated in its expression upon treatment with ANAVEX2-27, supporting the key finding that Sig-1R activation has a positive modulatory effect on autophagy.

Example 30

ANAVEX2-73 Positively Regulates Autophagy, Increases Proteostasis Capacity and Improves Protein Aggregation-Mediated Paralysis in *C. elegans*

Figure 37A:
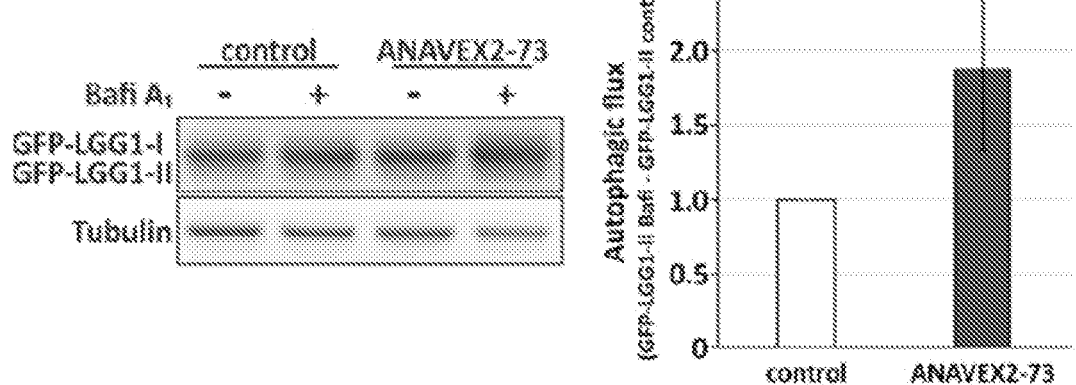
FIG. 37A shows a Western blot and a plot quantifying the results of the Western blots of GFP-LGG1 after treatment of worms with ANAVEX2-73. Statistics are depicted as mean±SD. * p<0.05, t-test, n=3.
Figure 37B:
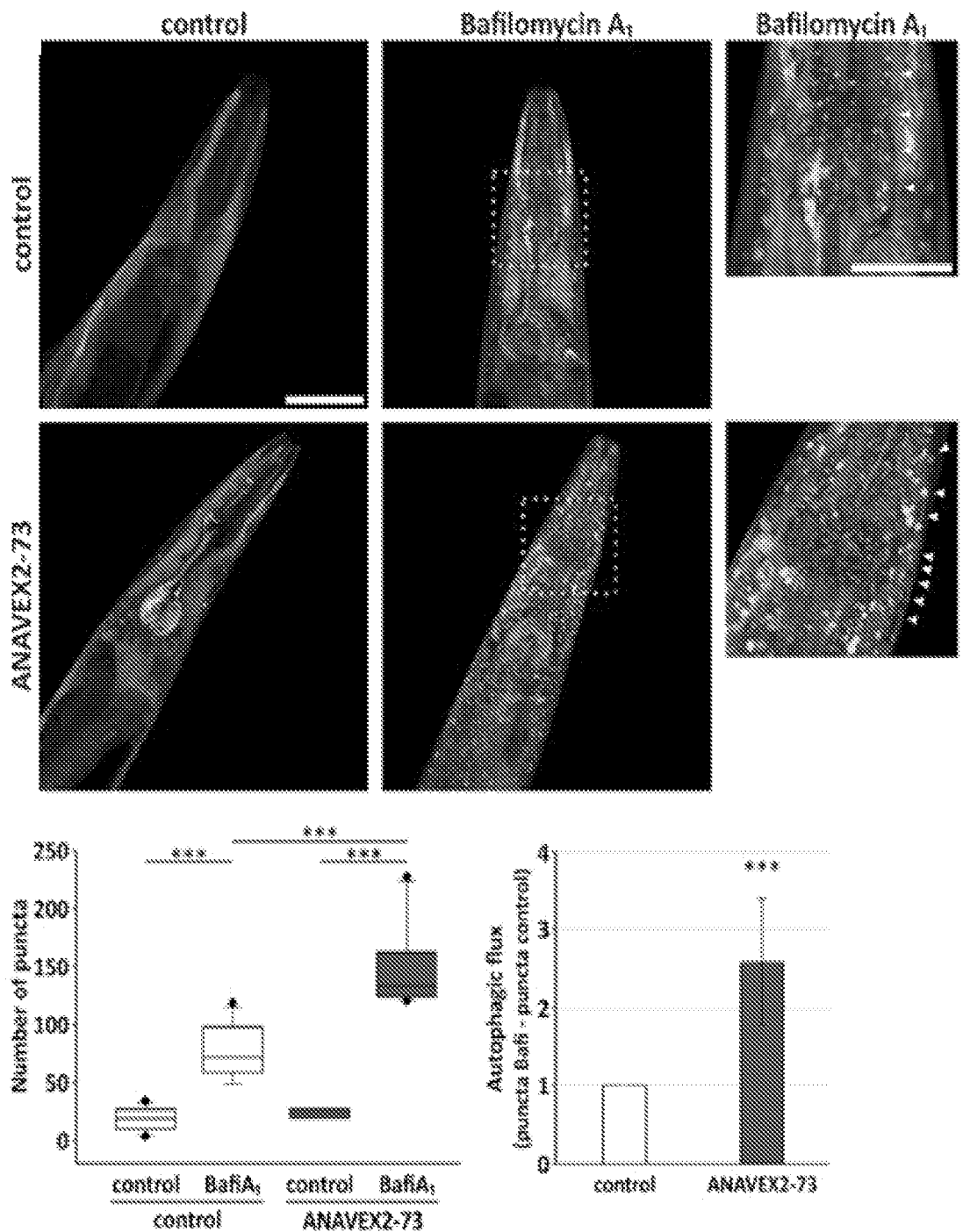
FIG. 37B are representative confocal fluorescence microscopic images of *C. elegans* treated with ANAVEX2-73 and BafiA$_1$ or DMSO, and plots quantifying the number of puncta in the microscopic images. Scale bar=50 and 25 gm. Arrowheads indicate autophagosomal structures. Autophagic flux was calculated as indicated, comparing GFP-positive puncta plus BafiA$_1$ with puncta in the controls *** p<0.001, t-test.

Autophagy modulation by ANAVEX2-73 in vitro and its impact on some key autophagy network factors prompted the inventors to further analyze the impact of Sig-1R activation by ANAVEX2-73 on autophagy and proteostasis also in vivo, employing the *C. elegans* model. The nematode ortholog of the human Sig-1R is W08F4.3 and is expressed in several tissues, including the muscular system. To monitor autophagic flux in vivo the inventors employed a GFP-LGG-1 reporter worm strain. LGG-1 is a nematode ortholog of the mammalian GABARAP, and the GFP-tagged protein can be used to evaluate autophagic activity by Western blotting as well as confocal fluorescence microscopy. Employing Western blotting, the levels of GFP-LGG-1-II plus BafiA$_1$ and without BafiA$_1$ were analyzed, analogously to the flux measurements in HeLa cells as shown in FIG. 37. Indeed, ANAVEX2-73 (80 µM) significantly enhanced autophagic flux in *C. elegans* almost 2-fold (Nematodes treated with BafiA$_1$ or DMSO for 6 h. FIG. 37A).

To further substantiate this finding we used confocal fluorescence microscopy to directly visualize autophagosomal structures, as indicated by GFP-LGG-1-positive puncta. ANAVEX2-73 supplementation (plus/minus BafiA1) significantly increased the number of GFP-LGG1 puncta, which is indicative of increased autophagic activity; treatment of worms with ANAVEX2-73 lead to a relative increase in numbers of puncta after BafiA1 treatment when compared to control worms. In fact, a significant increase was found; autophagic flux as observed in vivo is induced by ANAVEX2-73 by approx. 2.5-fold (FIG. 37B; The number of GFP-positive autophagosomal structures (indicated by arrowheads) were counted in three independent experiments and in each experiment in at least 8-11 respective head regions of worms), which is consistent with the Western blot analysis (FIG. 37A).

Figure 38A:
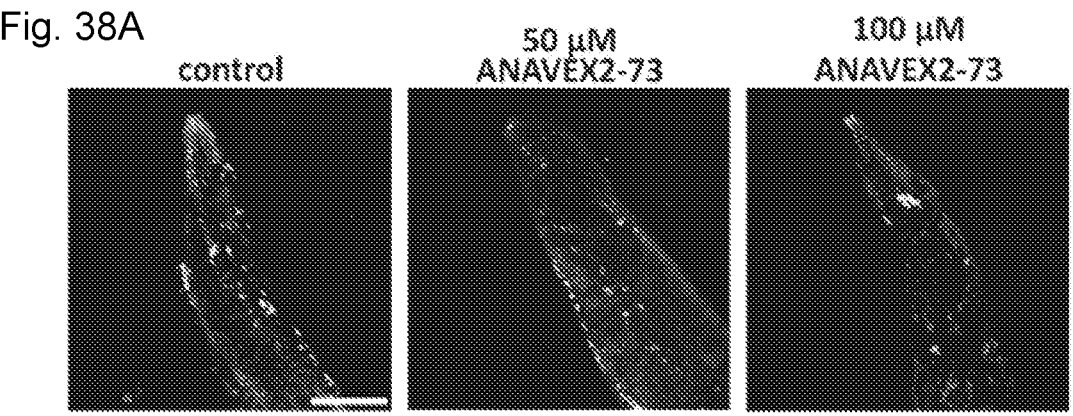
FIG. 38A shows representative confocal fluorescence microscopic images of Thioflavin S-positive Aβ42 aggregates in head regions of nematodes. Scale bar=50 μm.
Figure 38B:
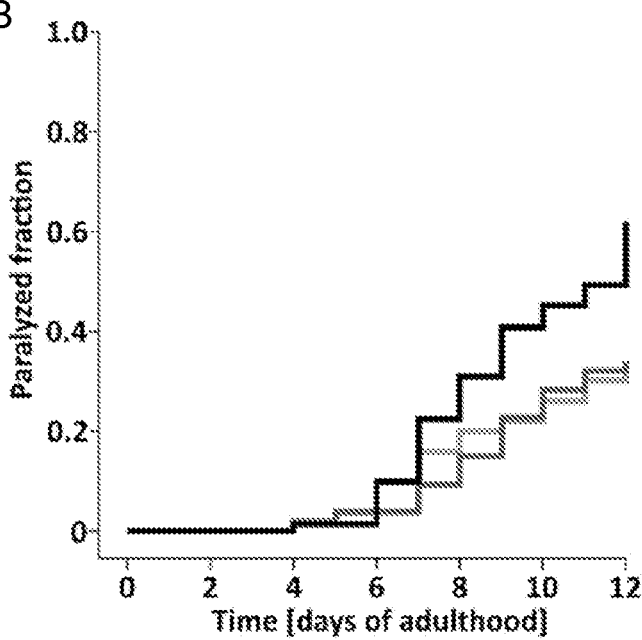
FIG. 38B is a plot of the analyses of Aβ42-induced paralysis. Statistics were conducted using the log-rank test. Three independent experiments with a total of approx. 70 worms per treatment. Black=control, light grey=50 μM ANAVEX2-73, dark grey=100 !AM ANAVEX2-73.

Taken together, the in vitro and in vivo data clearly show that the Sig-1R agonist ANAVEX2-73 induces autophagy, as indicated by autophagic flux measurements. This encouraged the inventors to further look into the functional consequences of autophagy induction, focusing on the impact of the degradative pathway on proteostasis in vivo. Therefore, human Aβ42-expressing worms characterized by a time-dependent paralysis were employed, due to the accumulation of Aβ42 oligomers and high molecular weight aggregates in body wall muscle cells; it is stressed here that Aβ42-expressing worms are not considered as a model for AD, but rather as an experimental model for general proteostasis stress and proteotoxicity, where protein aggregation in muscle cells leads do a clear-cut phenotype (here, paralysis). Aβ42 protein aggregates were stained in situ with thioflavine. Compared to control worms, treatment of Aβ42- worms with ANAVEX2-73 reduced the number of thioflavine-positive Aβ42 aggregates (FIG. 38A; worms were treated with 80 μM ANAVEX2-73 or M9 medium (control), for nine consecutive days), suggesting that the induction of autophagy impacts on proteostasis, presumably by an enhanced clearance of Aβ42 aggregates, resulting in a reduced tissue deposition of aggregates. The accumulation of Aβ42 aggregates in the muscle cells is known to lead to an enhanced paralysis of the worms over time. To analyze the impact of ANAVEX2-73-induced autophagy on the time-dependent movement behavior, the extent of this paralysis was investigated. C. elegans were treated with the compound (or M9 buffer as control) up to 12 days and paralysis was quantified daily. Employing two concentrations of ANAVEX2-73 (50 and 100 μM), we found a clear reduction in paralysis in the two ANAVEX2-73 treatment groups; these groups clearly separate from the controls with respect to the extent of paralysis (FIG. 38B; Worms were maintained in the presence of ANAVEX2-73 or M9 buffer and the paralysis phenotype was examined daily.) The paralyzed fraction is significantly different comparing ANAVEX2-73 treated and control worms. Therefore, ANAVEX2-73 clearly decelerates the paralysis rate and counteracts the time-dependent movement impairment in Aβ42-expressing worms.

The findings described herein, that autophagy induction via a Sig-1R agonist is directly impacting on proteostasis by reducing protein aggregation and proteotoxicity-induced behavioral impairment in worms demonstrates a role of Sig-1R activation in the prevention and treatment of neurodegeneration associated with an imbalanced protein homeostasis. Consistently with the ANAVEX2-73-induced increase in proteostasis capacity observed herein, the involvement of Sig-1R deficiency or dysfunction has been described in ALS, a disorder with a highly disturbed protein homeostasis and characteristic intracellular protein aggregation. For instance, it has been shown that (1) Sig-1R missense mutation can cause ALS, (2) the knock-out of Sig-1R accelerates disease in SOD1-mutant mice, and (3) an ALS-linked mutant Sig-1R causes accumulation of autophagic material and reduced autophagy. Furthermore, in support of a protective role of Sig-1R activity, it was previously described that (1) treatment with the experimental drug PRE-084 improves SOD1 mice pathology, (2) mutant Sig-1R expression induces cytosolic ALS-linked TDP43 and FUS accumulation in cells, and (3) PRE-084 improves motor function and motor neuron survival in ALS mice. Fully consistent with the finding herein, the overexpression of Sig-1A receptor increases the number of p62/SQSTM1 and LC3B puncta indicative of autophagy activation in human disease tissue.

Several steps of the autophagic processes are amenable to therapeutic modulation and different autophagy-activating compounds have already been studied at various experimental levels (in vitro and in vivo) and models of human diseases, including cancer and neurodegeneration. Regarding an effective intervention of neurodegenerative disorders, of course, for any compound planned to be studied in humans in the context of the central nervous system, besides toxicity and safety issues, also the permeability of the blood-brain barrier has to be secured. One example of a compound targeting autophagy is lithium, which is in use for the treatment of bipolar disorders and is also an activator of autophagy, by interfering with upstream steps in autophagy induction. Metformin and simvastatin have also been shown, experimentally, to promote autophagy, both supposedly via the activation of AMPK, and are used for the treatment of diabetes and obesity, respectively. Sig-1R agonists are under intense investigation for the treatment of different neurodegenerative diseases, including AD and ALS. Without being constrained by theory, it is the combination of receptor activities that may make ANAVEX2-73 an interesting compound for AD therapy.

Taken together, the results presented in Examples 28-30 herein show that Sig-1R activation (a) enhances the autophagic flux in human cells and in C. elegans, and (b) has positive effects on proteostasis. A novel activity of the compound ANAVEX2-73 having dual selective Sig-1R/muscarinic activities in neurons is described. The activity of this drug comprises a potent induction of autophagy, in vitro and in vivo, leading to an increased proteostasis capacity, and even to beneficial effects on the time-dependent paralysis phenotype in Aβ42-expressing C. elegans. A specific induction of the autophagy process and a subsequent stabilization of the proteostasis in neurons represents one important step towards the stabilization of neuronal survival and function, and can help to prevent age-associated neurodegeneration.

Introduction for Examples 28-30

The pathogenesis of neurodegenerative disorders, including Alzheimer's and Parkinson's disease (AD, PD) as well as Amyotrophic Lateral Sclerosis (ALS), has been linked to a disturbed protein homeostasis. Therefore, the control and maintenance of proteome integrity and proteostasis is of utmost importance. Cellular proteostasis includes protein folding, protein assembly, refolding of damaged proteins as well as protein degradation and is under the control of a fine tuned network of factors including chaperones such as heat shock protein 70 (HSP70) and distinct co-chaperones. For intact function and long-term survival of the cell, it is crucial to remove misfolded proteins via specialized processes; the two major cellular degradation pathways are ubiquitin proteasome system (UPS) and autophagy. The UPS is of particular importance for the physiological protein turnover but is limited in the degradation substrates and the autophagic-lysosomal pathway is responsible for the clearance of aggregated and disease-associated proteins, especially under pathogenic and aging conditions.

Autophagy is a highly dynamic vesicle-mediated cellular degradation pathway involving double-membraned vesicles, called autophagosomes, which sequester large protein complexes (protein aggregates), and even whole organelles and deliver them to lysosomes for degradation. Under low nutrition and energy conditions autophagy guarantees energy supply by generating amino acid building blocks via recycling. In addition, autophagy plays an important role as a stress and adaptive response and rescue mechanism to maintain cell survival and function. Canonical autophagy responds to environmental cues via a variety of factors that mainly belong to homologs of autophagy-related (atg) genes originally identified in yeast. The mammalian target of rapamycin (mTOR) complex 1 (mTORC1) negatively regulates autophagic activity via inhibitory phosphorylation of ULK1 and is the key initial regulator of canonical autophagy. More downstream membrane expansion is modulated by two ubiquitin-like conjugating systems (ATG12-ATG5 and ATG8/LC3) and the ATG18 protein family members of WD repeat domain phosphoinositide interacting 1-3 (WIPI1-3).

There is a great amount of data linking dysfunction and malfunction of autophagy to neurodegenerative disease and consistent with its role in proteostasis, to the accumulation of protein aggregates. Thus, the modulation of autophagy has become one key pharmacological target in neurodegeneration. In fact, there are multiple overlaps of autophagy and pathogenesis pathways in AD, PD and ALS. Recently different alternative views and new pharmacological targets towards AD prevention and treatment are evolving and include a strong focus on the autophagy process.

There are two subtypes of sigma receptors, sigma-1 and sigma-2, both highly expressed in the central nervous system. Sigma-1 receptor (Sig-1R) was cloned in 1996 and represents an integral membrane protein of 223 amino acids protein localized to the endoplasmic reticulum (ER) (and the ER-mitochondrial interface) suggesting a role as ER chaperone. Sig-1R was shown to promote cellular survival by (1) ensuring Ca2+ signaling from the ER into mitochondria, (2) enhancing the signaling of ER to the nucleus, and (3) attenuating free radical damage by modulation of the activity of Nrf2, a redox-responsive transcription factor. Structurally, Sig-1R ligand binding is characterized and the crystal structure of the human receptor is solved.

In general, deficits in Sig-1R expression or activity are linked to neurodegeneration and the activation of Sig-1R is associated with neuroprotection in different in vitro and in vivo models, employing different types of pharmacological Sig-1R activators with different pharmacological profiles. The pharmacological activation of Sig-1R leads to pluripotent modulatory downstream effects and incorrect function of Sig-1R is strongly suggested to be also involved in the pathogenesis of neurodegeneration. This is the basis of an effort to design novel and highly specific pharmacological Sig-1R activators for the therapy of neurodegenerative disease, including.

In this context a novel Sig-1R agonist, tetrahydro-N,N-dimethyl-2,2-diphenyl-3-furanmethanamine hydrochloride (ANAVEX2-73), was developed. Pharmacologically ANAVEX2-73 shows a mixed activity on Sig-1R as well as muscarinic receptor, acting with described affinities in the low micromolar range. Previously, pre-clinical studies in animal models demonstrated robust disease-modifying activities of ANAVEX2-73. Regarding AD, ANAVEX2-73 has undergone testing in Phase 2a trial of patients demonstrating a favorable safety profile and a concentration-dependent improvement against exploratory endpoints. A variety of neuromodulatory and neuroprotective effects are also already known for ANAVEX2-73 including mitochondrial protection in mouse models of AD, regulation of ERK activation and promotion of survival of astrocytes, as well as protection against oxidative stress.

First evidence for a possible link of Sig-1R, autophagy and neurodegeneration have been recently shown in the context of ALS. It was discovered that ALS-linked mutant Sig1-R causes an accumulation of autophagic material and actually reduced autophagy. In addition, it was found that a small-molecule Sig-1R modulator induces autophagic degradation of programmed-death ligand 1 (PD-L1) in cancer cells. These findings prompted us to study the potential of ANAVEX2-73 to effect autophagy in human HeLa and HEK293 cells (in vitro) as well as in C. elegans (in vivo), employing standard measures to analyze autophagic activity, which are well-established by the inventors. Moreover, the effects of ANAVEX2-73 on protein aggregation and subsequently the impact of protein aggregates on movement behavior in C. elegans were studied. Excitingly, ANAVEX2-73 is a potent inducer of autophagic flux in vitro and in vivo and ameliorates protein aggregate formation and paralysis in C. elegans.

Materials and Methods for Examples 28-30

Cell culture and microscopy. HeLa and HEK293A cells were cultured in DMEM (Invitrogen, Carlsbad, Calif., USA, 41965062) supplemented with active FBS (Life Technologies GmbH, Carlsbad, Calif., USA, 10270106), 1×ABAM (Invitrogen, 15240-062) and 1 mM sodium pyruvate (Invitrogen, 1136-088). After medium change, the cells were treated for 2 h with 10, 1, and 0.1 µM ANAVEX2-73 and PRE-084 (Tocris, Bristol, UK, 0589), respectively; ANAVEX2-73 was provided by ANAVEX Life Sciences Corp, New York, N.Y., USA. Afterwards Bafilomycin $A_1$ (Bafi.$A_1$; 2 µM) (Toronto Research Chemicals, North York, ON, Canada, B110000) or DMSO was added for a further 2 h and the cells were eventually harvested. Western blot analyses were performed as described previously [40, 41]. Briefly, cells were subjected to SDS-PAGE using precast NuPAGE 4%-12% Bis-Tris gels (Invitrogen, NP0322). Proteins were detected by chemiluminescence using the Amersham Imager 600 (GE).

Confocal fluorescence microscopical analyses of HEK293A cells stably expressing GFP-LC3B were performed with the laser scanning microscope LSM 710 (Zeiss, Oberkochen).

C. elegans strains, maintenance, methods. C. elegans were maintained according to standard procedures on nematode growth medium (NGM) plates seeded with HB101 E. coli. The following strains were employed in this study: GFP::LGG-1 (ex[PIggI::IggI::GFP]/pRF4; maintained at 20° C.; and the strain CL2006 (dvls2 [pCL12(unc-54/human Aβ peptide 1-42)+pRF4]), maintained at 15° C.

For analysis of paralysis rate, synchronous CL2006 nematodes were cultivated at 15° C. on plates seeded with HB101 E. coli re-suspended in M9 (control) or 100 µM and 50 µM ANAVEX2-73. Starting at first day of adulthood, worms were transferred to fresh plates daily and were tested for paralysis by tapping their nose with a platinum wire. Worms that moved their nose but failed to move their bodies were scored as paralyzed. Dead worms or worms showing other phenotypes were not included into the statistics. Staining of amyloid β42 aggregates using thioflavine S (Sigma T1892) were carried out as previously described. Worms were mounted on 2% agar pads on a glass slide and confocal fluorescence microscopical analyses were performed with the LSM 710 (Zeiss, Oberkochen) laser scanning microscope.

For analysis of autophagic activity, synchronous nematodes expressing GFP::LGG-1 were cultivated at 20° C. At first day of adulthood, worms were transferred to 80 µM ANAVEX2-73 or control M9 liquid culture medium for 2 h and subsequently were treated with Bafilomycin A1 or DMSO (control) for 4-6 h. Thereafter worms were lysed for Western blotting or analyzed by confocal fluorescence microscopy.

Western blot analyses were performed as described previously. Generally, 12 worms were subjected to SDS-PAGE using precast NuPAGE 4-12% Bis-Tris gels (Invitrogen, NP0322). Proteins were detected by chemiluminescence using the Fuji LAS-3000 dark box (Fujifilm, Dusseldorf).

The invention claimed is:

1. A crystalline form of tetrahydro-N,N-dimethyl-2,2-diphenyl-3-furanmethanamine (A2-73), wherein the crystalline form is a fumarate salt or a free base, wherein:
 the fumarate salt is characterized by the XRPD pattern shown in FIG. 29, FIG. 30, FIG. 33, or FIG. 34, and
 the free base is characterized by the XRPD pattern shown in FIG. 16.

2. The crystalline form of claim 1, wherein the fumarate salt characterized by the XRPD pattern shown in FIG. 29 is further characterized by the particle shapes depicted in FIG.

28, and the fumarate salt characterized by the XRPD pattern shown in FIG. 32 is further characterized by the particle shapes depicted in FIG. 31.

3. The crystalline form of claim 1, wherein the free base characterized by the XRPD pattern shown in FIG. 16 is further characterized by the particle shapes depicted in FIG. 15.

4. A dosage form comprising a therapeutically effective amount of a crystalline form of A2-73 fumarate salt or A2-73 freebase according to claim 1.

5. The dosage form of claim 4, wherein the dosage form comprises from about 1 mg to about 50 g, from about 1 mg to about 500 mg, or about 1 mg to about 100 mg of A2-73 freebase or A2-73 fumarate salt.

6. The dosage form of claim 4, wherein the dosage form is formulated for extended release of crystalline freebase or fumarate salt of A2-73.

7. The dosage form of claim 6, wherein the dosage form comprises from about 1 mg to about 500 mg of A2-73 freebase.

8. The dosage form of claim 6, wherein the dosage form is a transdermal patch.

9. The dosage form of claim 8, wherein the transdermal patch comprises from about 40 mg to about 60 mg, from about 80 mg to about 120 mg, or from about 180 mg to about 220 mg of A2-73 freebase.

10. The dosage form of claim 6, wherein the dosage form is an enteric coated oral formulation.

11. The dosage form of claim 10, wherein the enteric coated oral formulation comprises from about 1 mg to about 50 mg A2-73 freebase.

12. The dosage form of claim 6, wherein the dosage form is a transdermal patch.

13. The dosage form of claim 12, wherein the transdermal patch comprises from about 1 mg to about 55 mg of A2-73 fumarate salt.

14. The dosage form of claim 6, wherein the dosage form is an enteric coated oral formulation.

15. The dosage form of claim 14, wherein the enteric coated oral formulation comprises from about 10 mg to about 50 mg, from about 20 mg to about 30 mg, or from about 15 mg to about 25 mg of A2-73 fumarate salt.

16. A pharmaceutical formulation for delivery of A2-73, the formulation comprising a therapeutically effective amount of a crystalline form of A2-73 fumarate salt or A2-73 freebase according to claim 1, wherein the formulation further comprises one or more pharmaceutically acceptable excipients.

17. The formulation of claim 16, wherein the one or more pharmaceutically acceptable excipients is selected from the group consisting of chemical enhancers, humectants, pressure sensitive adhesives, antioxidants, solubilizers, thickening agents, plasticizers, adjuvants, carriers, vehicles, and any combinations thereof.

18. The formulation of claim 16, wherein the one or more pharmaceutically acceptable excipients are selected for oral, transdermal, parenteral, intraperitoneal, intravascular, subcutaneous, by inhalation spray, rectal, or intrapulmonary administration.

19. The formulation of claim 16, wherein the formulation is an oral formulation comprising from about 1% to about 100% by weight crystalline freebase or fumarate salt of A2-73.

20. The formulation of claim 16, wherein the formulation is for extended delivery of crystalline freebase or fumarate salt of A2-73.

21. The formulation of claim 20, wherein the formulation comprises from about 1 mg to about 50 g of crystalline freebase or fumarate salt of A2-73.

22. The formulation of claim 20, wherein the formulation is a subcutaneous injectable dosage formulation comprising from about 0.5 g to about 3 g of crystalline freebase or fumarate salt of A2-73.

23. The formulation of claim 16, wherein the formulation is a transdermal patch.

24. The formulation of claim 23, wherein the patch comprises from about 40 mg to about 60 mg, from about 80 mg to about 120 mg, or about 180 mg to about 220 mg of A2-73 freebase.

25. The formulation of claim 23, wherein the patch comprises from about 1 mg to about 55 mg of A2-73 fumarate salt.

26. The formulation of claim 16, wherein the formulation is an oral formulation.

27. The formulation of claim 26, wherein the oral formulation comprises from about 1 mg to about 50 mg A2-73 freebase.

28. The formulation of claim 26, wherein the oral formulation comprises from about 10 mg to about 50 mg, from about 20 mg to about 30 mg, or from about 15 mg to about 25 mg of A2-73 fumarate salt.

29. The formulation of claim 16, wherein the formulation is a subcutaneous dosage form comprises from about 0.1 to about 5 g of crystalline freebase or fumarate salt of A2-73.

* * * * *

UNITED STATES PATENT AND TRADEMARK OFFICE
CERTIFICATE OF CORRECTION

PATENT NO. : 11,498,908 B2
APPLICATION NO. : 17/046929
DATED : November 15, 2022
INVENTOR(S) : Christopher U. Missling and Alani Selvey It is certified that error appears in the above-identified patent and that said Letters Patent is hereby corrected as shown below:

In the Claims

Replace Claim 1 presented at Column 52, Lines 56-64 with the following:
1. A crystalline form of tetrahydro-N,N-dimethyl-2,2-diphenyl-3-furanmethanamine (A2-73), wherein the crystalline form is a fumarate salt or a free base, wherein:
    the fumarate salt is characterized by the XRPD pattern shown in FIG. 29, FIG. 30, FIG. 32, FIG. 33, or FIG. 34, and
    the free base is characterized by the XRPD pattern shown in FIG. 16.

Signed and Sealed this
Twelfth Day of November, 2024

Katherine Kelly Vidal
*Director of the United States Patent and Trademark Office*